US008551469B2

(12) United States Patent  
Wei

(10) Patent No.: US 8,551,469 B2
(45) Date of Patent: *Oct. 8, 2013

(54) TREATMENT OF TUMORS AND VIRAL DISEASES WITH RECOMBINANT INTERFERON ALPHA

(75) Inventor: Guangwen Wei, Sichuan (CN)

(73) Assignee: Superlab Far East Limited, Road Town, Tortola (VG)

( * ) Notice: Subject to any disclaimer, the term of this patent is extended or adjusted under 35 U.S.C. 154(b) by 0 days.

This patent is subject to a terminal disclaimer.

(21) Appl. No.: 12/246,153

(22) Filed: Oct. 6, 2008

(65) Prior Publication Data

US 2009/0123417 A1 May 14, 2009

Related U.S. Application Data

(63) Continuation of application No. 11/077,813, filed on Mar. 10, 2005, now abandoned, which is a continuation-in-part of application No. 10/927,975, filed on Aug. 26, 2004, now abandoned, which is a continuation-in-part of application No. 10/650,365, filed on Aug. 28, 2003, now Pat. No. 7,364,724, which is a continuation-in-part of application No. PCT/CN02/00128, filed on Feb. 28, 2002.

(30) Foreign Application Priority Data

| Feb. 28, 2001 | (CN) | ................................. 01 1 04367 |
| Feb. 28, 2002 | (WO) | ....................... PCT/CN02/00128 |
| Mar. 5, 2004 | (IN) | ............................ 279/MUM/2004 |
| Mar. 5, 2004 | (IN) | ............................ 280/MUM/2004 |

(51) Int. Cl.
*A61K 38/21* (2006.01)
*A61K 38/00* (2006.01)
*C07K 14/56* (2006.01)

(52) U.S. Cl.
USPC ......... 424/85.7; 530/351; 514/1.1; 435/69.51

(58) Field of Classification Search
None
See application file for complete search history.

(56) References Cited

U.S. PATENT DOCUMENTS

| 4,672,108 | A |   | 6/1987 | Kung et al. | |
| 4,681,930 | A |   | 7/1987 | Kung et al. | |
| 4,695,623 | A | * | 9/1987 | Stabinsky | ..................... 530/351 |
| 4,897,471 | A | * | 1/1990 | Stabinsky | ..................... 536/23.1 |
| 5,372,808 | A | * | 12/1994 | Blatt et al. | ..................... 424/85.4 |
| 5,441,734 | A |   | 8/1995 | Reichert et al. | |
| 5,602,232 | A |   | 2/1997 | Reichert et al. | |
| 5,972,331 | A |   | 10/1999 | Reichert et al. | |
| 5,980,884 | A |   | 11/1999 | Blatt et al. | |
| 6,114,145 | A |   | 9/2000 | Olsen et al. | |
| 2004/0014722 | A1 |   | 1/2004 | Babu et al. | |
| 2004/0202641 | A1 |   | 10/2004 | Wei et al. | |

FOREIGN PATENT DOCUMENTS

| WO | WO 93/21229 | 10/1993 |
| WO | WO 97/27866 | 8/1997 |
| WO | WO 01/35987 A1 | 5/2001 |
| WO | WO 02/10411 A2 | 2/2002 |
| WO | WO 02/36627 | 5/2002 |
| WO | WO 02/080958 A1 | 10/2002 |
| WO | WO 2005/034853 A2 | 4/2005 |
| WO | WO 2005/067963 | 7/2005 |
| WO | WO 2006/134497 A2 | 12/2006 |

OTHER PUBLICATIONS

Li, F., et al. Antiviral effects of rhIFN-alpha 1 against seven influenza viruses. Acta. Pharmacol. Sin., 1999, vol. 20, No. 8., p. 709-714.*
Moore, D.H., et al. A phase I study of intraperitoneal interferon-alpha 2b and intravenous cis-platinum plus cyclophosphamide chemotherapy in patients with untreated state III epithelial ovarian cancer: A gynecologic oncology group pilot study. Gynecologic Oncology, 1995, vol. 59, p. 267-272.*
Goldstein D., et al. The role of interferon in cancer therapy: A current perspective. CA Cancer J Clin., 1998, vol. 38, p. 258-277.*
Notification of Transmittal of international Preliminary Report on Patentability (Chapter II of the Patent Cooperation Treaty) for PCT/US04/28067 for Huiyangtech (USA), Inc., Dated Mar. 5, 2007.
International Search Report, Application No. PCT/US2004/028067 for Huiyangtech, Inc., "Uses of interferons with altered spatial structure,"Filed Aug. 26, 2004, Dated Feb. 27, 2006, Date of Completion of the Search: Nov. 2, 2005.
International Search Report, Application No. PCT/CN02/00128 for Sichuan Biotechnology Research Center, "Recombination Super Compound Interferon Used as Hepatitis B Surface Antigen and E Antigen Inhibitor," Filed Feb. 28, 2002, Dated Aug. 8, 2002, Date of Completion of the Search: Jul. 23, 2002.
International Preliminary Examination Report, Application No. PCT/CN02/00128 for Sichuan Biotechnology Research Center, "Recombination Super Compound Interferon Used as Hepatitis B Surface Antigen and E Antigen Inhibitor," Filed Feb. 28, 2002, Dated Feb. 15, 2004.
Notification Concerning Transmittal of International Preliminary Report on Patentability (Chapter I of the Patent Cooperation Treaty) for PCT/IB2006/002340 for Guangwen Wei, Dated Sep. 20, 2007.
Notification of Transmittal of the International Search Report and the Written Opinion of the International Searching Authority for Guangwen Wei (International Search Report and Written Opinion included), Application No. PCT/IB2006/002340, Filed Mar. 9, 2006, Dated May 10, 2007.

(Continued)

*Primary Examiner* — Robert Landsman
*Assistant Examiner* — Bruce D Hissong
(74) *Attorney, Agent, or Firm* — Law Offices of Albert Wai-Kit Chan, PLLC

(57) ABSTRACT

This invention provides a recombinant interferon (rSIFN-co) and its equivalent with changed spatial configuration, high efficacy and low side effects. Therefore, high dose of rSIFN-co may be used. The cytotoxic effect of rSIFN-co is only one-eighth (⅛) of currently clinically available interferons but its anti-viral effect is approximately five to twenty (5-20) times higher, and when used in vivo it has a broader spectrum of clinical applications and longer biofeedback response. This invention further provides methods of using the recombinant interferon to treat proliferative disorders such as cancer or viral diseases.

15 Claims, 34 Drawing Sheets

(56) References Cited

OTHER PUBLICATIONS

Figure 3:
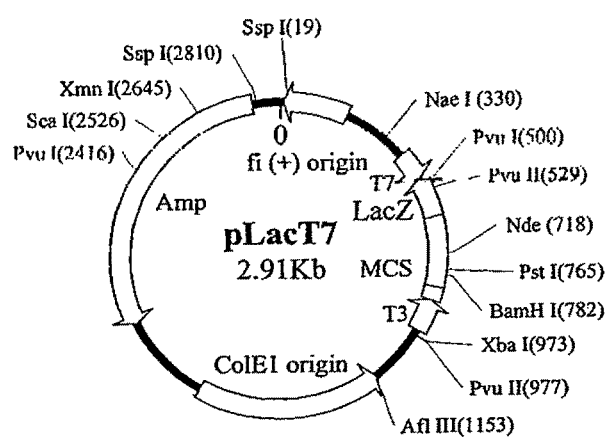

Written Opinion of the International Searching Authority for PCT/US2004/028067, Filed Aug. 26, 2004 for Huiyangtech (USA) Inc., Dated Feb. 27, 2006.
Austrian Written Opinion, Jun. 29, 2009, Singapore Application No. 200706014-8, Guangwen Wei, filed Mar. 9, 2006.
Chinese Patent No. CN 1375502A for Yao et al., Oct. 23, 2002, "Polyglycol Modified Recombinant Human Interferon".
Chinese Patent No. CN 1478545A for Gao et al., Mar. 3, 2004, "Use of Compound Interferon in the Treating of SARS Disease".
Chinese Patent No. CN 1099799A, Mar. 8, 1995, Hauptmann et al., "Method of Preparation and Purification of IFN."
Chinese Patent No. CN 1120846A, Apr. 17, 1996, Reichert et al., "Metal-Interferon-Crystal."
Chinese Patent No. CN 1217660A, May 26, 1999, Larry Blatt, and Michael Klein, "Method of Using Consensus Interferon to Retreat Patient with Hepatitis."
Chinese Patent No. CN 1256148A, Jun. 14, 2000, Lei Zhang, "A Stable Interferon Solution."
Chinese Patent No. CN 1384116A, Dec. 11, 2002, Chun Lei Jiang, and Yun Xia Wang, "A New Type of Interferon."
Chinese Patent No. CN 1098103C, Jan. 8, 2003, Lawrence M. Blatt and Milton W. Taylor, "Pharmaceutical Application of Sympathetic Human Leucocyte Interferon."
Chinese Patent No. CN 1062565C, Feb. 28, 2001, Zhao, et al., "Preparation Method and Application of Recombinant Human Consensus Interferon."
European Patent Publication No. EP 0083734 B1, Dec. 3, 1982, Kung et al., "Crystalline Human Leukocyte Interferon."
European Patent Publication No. EP 0736303 B1, Oct. 9, 1996, Gross et al., "Interferon Solution."
International Publication No. WO 1996/11018, Apr. 18, 1996, Pui-Ho Yuen and Douglas Kline, "Stable Aquous Alfa Interferon Solution Formulations."
European Patent Publication No. EP 1371373 A1, Dec. 17, 2003, Sichuan Biotechnology Research Center, "Recombination Super Compound Interferon Used as Hepatitis B Surface Antigen and E Antigen Inhibitor."
Supplementary European Search Report for Sichuan Biotechnology Research Center, Application No. EP 02702211, Filed Feb. 28, 2002, Date of Completing of the Search: Feb. 23, 2005.
European Supplemental Search Report for Huiyangtech (USA), Inc., Application No. EP 04809634.1, Filed Mar. 26, 2006, Dated Jun. 17, 2008, Date of Completing of the Search: Jun. 10, 2008.
German Patent No. DE 4329756, Mar. 9, 1995, Hauptmann et al., "Method of Preparation and Purification of IFN-α." (English abstract).
Australian Examiner's Report for Sichuan Biotechnology Research Center, Australian Application No. 2003248419, Filed Sep. 26, 2003, Dated Dec. 12, 2005.
Australian Examiner's Report for Sichuan Biotechnology Research Center, Australian Application No. 2003248419, Filed Sep. 26, 2003, Dated Jun. 1, 2006.
Australian Notice of Acceptance for Sichuan Biotechnology Research Center, Australian Application No. 2003248419, Filed Sep. 26, 2003, Dated Dec. 18, 2008.
Canadian Office Action, Apr. 21, 2008, for Sichuan Biotechnolgy Research Center, Canadian Application No. 2,439,503, Filed Aug. 27, 2003.
Canadian Office Action, Jun. 1, 2009, for Sichuan Biotechnolgy Research Center, Canadian Application No. 2,439,503, Filed Aug. 27, 2003.
Chinese Second Notification of Examination, Oct. 17, 2003, for Sichuan Biological Research Center, Chinese Application No. 01104367.9, Filed Feb. 28, 2001. [with full English translation].
Chinese Third Notification of Examination, Jan. 2, 2004, for Sichuan Biological Research Center, Chinese Application No. 01104367.9, Filed Feb. 28, 2001. [with full English translation].
Chinese Fourth Notification of Examination, Jun. 4, 2004, for Sichuan Biological Research Center, Chinese Application No. 01104367.9, Filed Feb. 28, 2001. [with full English translation].
Chinese Decision About Rejection, Nov. 12, 2004, for Sichuan Biological Research Center, Chinese Application No. 01104367.9, Filed Feb. 28, 2001. [with full English translation].
Chinese Decision About the Reexamination, Oct. 26, 2005, for Sichuan Biological Research Center, Chinese Application No. 01104367.9, Filed Feb. 28, 2001. [with full English translation].
Chinese First Notification of Examination, Apr. 18, 2003, for Sichuan Biological Research Center, Chinese Application No. 01104367.9, Filed Feb. 28, 2001. [with full English translation].
Chinese First Office Action, Nov. 20, 2009, for Huiyangtech (USA), Inc., Chinese Application No. 200480031910.0, Filed Apr. 28, 2006.
Chinese First Office Action, Mar. 27, 2009, for Huiyangtech (USA), Inc., Chinese Application No. 200480031910.0, Filed Apr. 28, 2006.
Chinese First Office Action, May 22, 2009, for Guangwen Wei, Chinese Application No. 200680007733.1, Filed Sep. 10, 2007.
European Communication Under Rule 71(3) EPC, Jun. 19, 2009 for Sichuan Biotechnology Research Center, European Application No. 02702211.0, Filed Sep. 25, 2003.
European Communication for Sichuan Biotechnology Research Center, European Application No. 02702211.0, Filed Sep. 25, 2003, Dated Dec. 14, 2006.
Japanese Notification of Reasons of Refusal, Jun. 17, 2008, for Sichuan Biotechnology Research Center, Japanese Application No. 2002-578997, Filed Aug. 28, 2003. [with full English translation].
Malaysian Examiner's Report, Mar. 8, 2007, Sichuan Biotechnology Research Center, Malaysian Application No. PI 20033246, Filed Aug. 28, 2003.
Malaysian Office Action, Aug. 11, 2008, for Sichuan Biological Research Center, Malaysian Patent Application No. PI 20033246, Filed Aug. 28, 2003.
Malaysian Office Action, Jan. 16, 2009, for Sichuan Biological Research Center, Malaysian Patent Application No. PI 20033246, Filed Aug. 28, 2003.
Malaysian Office Action, Jul. 13, 2009, for Sichuan Biological Research Center, Malaysian Patent Application No. PI 20061015, Filed Mar. 9, 2006.
Singapore Certificate of Grant of Patent, Nov. 30, 2005, for Sichuan Biotechnology Research Center, Singapore Application No. 2003-04969, Filed Aug. 28, 2003.
Singapore Patent No. 200601209, Oct. 31, 2008, Huiyangtech(USA), Inc., "Uses of Interferons with altered spatial structure". Filed Feb. 23, 2006.
Examiner's Written Opinion, Jan. 8, 2008, Huiyangtech (USA), Inc., Singaporean App'l No. 200601209-0, Filed Feb. 23, 2006. (Australian Patent Office Written Opinion issued Dec. 4, 2007).
Taiwanese Office Action, Sep. 21, 2006, Sichuan Biotechnology Research Center, Taiwanese Application No. 92,123,846, Filed Aug. 28, 2003.
Taiwanese Formal Rejection, Dec. 11, 2006, Sichuan Biotechnology Research Center, Taiwanese Application No. 92,123,846, Filed Aug. 28, 2003.
Taiwanese Examination Report, Dec. 12, 2008, for Guangwen Wei, Taiwanese Application No. 95107930, Filed Mar. 9, 2006. [with full English translation].
Taiwanese Examination Report, May 25, 2009, for Guangwen Wei, Taiwanese Application No. 95107930, Filed Mar. 9, 2006. [with full English translation].
U.S. Notice of Allowance and Fee(s) Due, Jul. 26, 2007, Wei et al., U.S. Appl. No. 10/650,365, filed Aug. 28, 2003.
U.S. Office Action for Wei et al., Aug. 23, 2005, U.S. Appl. No. 10/650,365, filed Aug. 28, 2003.
U.S. Office Action, Sep. 20, 2006, Wei et al., U.S. Appl. No. 10/650,365, filed Aug. 28, 2003.
U.S. Office Action, Mar. 7, 2007, Wei et al., U.S. Appl. No. 10/650,365, filed Aug. 28, 2003.
U.S. Office Action, Mar. 20, 2006, Wei et al., U.S. Appl. No. 10/650,365, filed Aug. 28, 2003.
U.S. Office Action, Jun. 14, 2007, Guangwen Wei, U.S. Appl. No. 10/928,956, filed Aug. 26, 2004.

(56) References Cited

OTHER PUBLICATIONS

U.S. Office Action, Dec. 15, 2006, Guangwen Wei, U.S. Appl. No. 10/928,956, filed Aug. 26, 2004.
U.S Office Action, Aug. 1, 2007, Guangwen Wei, U.S. Appl. No. 11/077,813, filed Mar. 10, 2005.
U.S. Office Action, Nov. 27, 2006, Guangwen Wei, U.S. Appl. No. 11/077,813, filed Mar. 10, 2005.
U.S. Office Action, Aug. 8, 2006, Guangwen Wei, U.S. Appl. No. 11/077,813, filed Mar. 10, 2005.
U.S. Advisory Action Before the Filing of an Appeal Brief, May 22, 2007, Guangwen Wei, U.S. Appl. No. 10/928,474, filed Aug. 26, 2004.
U.S. Office Action, Aug. 9, 2007, Guangwen Wei, U.S. Appl. No. 10/928,474, filed Aug. 26, 2004.
U.S. Office Action, Feb. 9, 2007, Guangwen Wei, U.S. Appl. No. 10/928,474, filed Aug. 26, 2004.
U.S. Office Action, Jan. 4, 2008, Guangwen Wei, U.S. Appl. No. 10/928,474, filed Aug. 26, 2004.
U.S. Advisory Action before the Filing of an Appeal Brief, Mar. 18, 2008, U.S. Appl. No. 10/928,474, filed Aug. 28, 2003.
U.S. Office Action, Feb. 6, 2008, Guangwen Wei, U.S. Appl. No. 11/077,813, filed Mar. 10, 2005.
U.S. Office Action, Feb. 23, 2009, for Guangwen Wei, U.S. Appl. No. 11/817,926, filed Sep. 6, 2007.
U.S. Office Action, Sep. 29, 2009, for Guangwen Wei, U.S. Appl. No. 11/817,926, filed Sep. 6, 2007.
U.S. Advisory Action Before the Filing of an Appeal Brief, Jul. 17, 2008, for Guangwen Wei, U.S. Appl. No. 11/077,813, filed Mar. 10, 2005.
U.S. Office Action, Apr. 29, 2005, for Guangwen Wei, U.S. Appl. No. 10/650,365, Patent No. 7,364,724, Filed Aug. 28, 2003.
U.S. Office Action, Aug. 8, 2006, for Guangwen Wei, U.S. Appl. No. 10/928,956, filed Aug. 26, 2004.
U.S. Office Action, Aug. 22, 2006, for Guangwen Wei, U.S. Appl. No. 10/928,474, filed Aug. 26, 2004.
U.S. Office Action, Jul. 18, 2008, Guangwen Wei, U.S. Appl. No. 11/817,926, filed Sep. 6, 2007.
U.S. Examiner's Answer to Appeal Brief, Dec. 9, 2008, for Guangwen Wei, U.S. Appl. No. 10/928,474, filed Aug. 26, 2004.
Infergen (Interferon alfacon-1) Product Sheet, Amgen, Inc., Issue Date: Nov. 30, 1998.
Alton, K. et al., 1983, "Production, characterization and biological effects of recombinant DNA derived human IFN-α and IFN-γ analogs." In: De Maeger E, Schellekens H. eds. The Biology of Interferon System 2nd ed. Amsterdam: Elsevier Science Publishers, p. 119-128.
Amato, Ivan, Jan. 22, 2007, "Silent No Longer: Researchers Unearth another Stratum of Meaning in the Genetic Code," Chemical and Engineering News, 85(4):38-40.
Ausubel et al., Eds., 1999, Chapter Ten, "Analysis of Proteins," from Short Protocols in Molecular Biology, 4th ed., p. 10-1 to 10-8.
Blatt, L.M. et al., 1996, "The biological activity and molecular characterization of a novel synthetic interferon-alpha species, consensus interferon," Journal of Interferon and Cytokine Research, 16(7):489-499.
Cinatl et al., 2003, "Treatment of SARS with Human Interferons," The Lancet, 362:293-294.
Duan et al., 2003, "Anti-SARS virus activities of different recombinant human interferons in cell culture system," Chinese J. Clin. Virol., 17(3):205-208.
Fei et al., 1999, "Clinical Observation of Effect on Treatment of Chronic Hepatitis B by a Combination of Interferon and Lamividine," Shandong Medical Journal, 39(11):3-4.
Gao et al., 1999, "Treatment of Hepatitis Virus Related Pediatric Nephritis With IFN," Academic Journal of Jinlin Hospital, 12(1):155-157.
Heathcote, E.J.L. et al., 1998, "Re-treatment of chronic hepatitis C with consensus interferon," Hepatology 27(4):1136-1143.

Higgins et al., 1983, "Intranasal Interferon as Protection against Experimental Respiratory Coronavirus Infection in Volunteers," Antimicrobial Agents and Chemotherapy 24(5):713-715.
Holland, C.C. and T.L. Wright, 1994, "New approaches to treatment of chronic viral hepatitis," Pathology (Phila.), 3(1).
Klein, M.L. et al., 1998, "Structural character-ization of recombinant consensus interferon-alpha," Journal of Chromatography, 454:205-215.
Lang et al., 2002, "Observation on Serology and Histology of Patients With Chronic Hepatitis B After Interferon Treatment," Chin. J. Infect. Dis., 20(2): 97-100.
Lei et al., 1995, "Observation on Clinical Treatment of Chronic Hepatitis B by Purified Human Leucocyte Interferon," Chinese Journal of Practical Internal Medicine, 15(3):155-157.
Nackley, A.G. et al., Dec. 22, 2006, "Human Catechol-O-Methyltransferase Haplotypes Modulate Protein Expression by Altering mRNA Secondary Structure," Science, 314:1930-1932.
Ozes, O.N. et al., 1992, "A comparison of interferon-con1 with natural recombinant interferons: antiviral, antiproliferative, and natural killer-inducing activities." J. Interferon Res., 12:55-59.
Pfeffer, L.M., 1997, "Biologic activity of natural and synthetic type 1 interferons," Seminars in Oncology, 24(3 suppl. 9):S9-63-S9-69.
Pyrc, K et al., 2007, "Antiviral strategies against human coronaviruses," Infectious Disorders—Drug Targets, (7):59-66.
Schulte-Frohlinde, et al., Feb. 21, 2002, "Different Activities of Type I interferons on Hepatitis B virus core promoter regulated transcription." Cytokine, 17(4): 214-220. [Cited by Examiner in Advisory Action of Mar. 18, 2008.]
Wang, Xiangye, and Li, Xuegang, 1994, "Comparing Effect of Three Drugs on Turning HBEAG to Negative," Qienwei Medical Journal, 11(4):197-198.
Wang, C. et al., 2006, "Refolding Recombinant Human Granulocyte Colony Stimulating Factor Expressed by E. coli: A Case Study Using the Unit of Simultaneous Renaturation and Purification of Proteins," BioProcess International, 48-53.
Yasuda, et al., 2000, "Spectrum of virus inhibition by consensus interferon YM643." Antiviral Chemistry & Chemotherapy, 11:337-341.
Zeng, Zheng et al., 2000, "Transfer and expression of human interferon-α and its effect on HBV inhibition," Chinese Journal of Infectious Disease, 18(4):221-224. [English abstract only].
Zheng, B. et al., Jul. 2004, "Potent inhibition of SARS-associated coronavirus (SCOV) infection and replication by type I interferons (IFN-alpha/beta) but not by type II interferon (IFN-gamma)," J. Interferon Cytokine Res., 24(7):288-90. [Abstract only].
Japanese Examiner's Report, Dec. 2, 2009, Sichuan Biotechnology Research Center, Japanese Patent Application No. 2002-578997, Filed Aug. 28, 2003.
Greenberg et al., Sep. 2, 1976, "Effect of human leukocyte interferon on hepatitis B virus infection in patients with chronic active hepatitis", 295(10):517-522.
U.S. Office Action, Dec. 29, 2009 Wei et al., U.S. Appl. No. 12/102,455, filed Apr. 18, 2008.
Chinese Examination Report, Nov. 27, 2009, Huiyangtech(USA), Inc., Chinese Application No. 200680007733.1, Filed Sep. 10, 2007.
Taiwanese Examiner's Report, Mar. 2010, Huiyangtech(USA), Inc., Taiwanese Appl No. 92,123,846, filed Aug. 28, 2003.
Australian Examiner's Report for Sichuan Biotechnology Research Center, Australian Application No. 2004279350, Filed Aug. 26, 2004, Dated Mar. 1, 2010.
Australian Examiner's Report, Mar. 1, 2010 for Sichuan Biotechnology Research Center, Australian Application No. 2004279350.
Indian Examiner's Report. May 4, 2010, Indian Application No. 00311/MUMNP/2006, Huiyangtech (USA) Inc., Filed Mar. 24, 2006.
U.S Office Action, Sep. 30, 2009, Guangwen Wei, U.S. Appl. No, 12/369,005, filed Feb. 11, 2009.
U.S. Office Action, Apr. 15, 2010, for Guangwen Wei, U.S. Appl. No. 12/369,005, filed Feb. 11, 2009.
Canadian Office Action, May 18, 2010, Sichuan Biotechnolgy Research Center, Canadian Application No. 2,439,503, Filed Aug. 27, 2003.

(56) References Cited

OTHER PUBLICATIONS

Indian Examiner's Report, May 10, 2010, Indian Application No. 1214/MUMNP/2007, Guangwen Wei, Filed Aug. 13, 2007.
Japanese Examiner's Report, Jul. 26, 2010, Huiyangtech (USA), Inc., Japanese Patent Application No. 2006-524916, Filed Feb. 27, 2006 (with English summary).
Singapore Written Opinion, Mar. 26, 2010, Guangwen Wei, Singapore Application No. 200706014-8, Filed Aug. 15, 2007.
Wong, Samson S. Y. and Yuen, Kwok-Yung, 2008, "The management of coronavirus infections with particular reference to SARS", Journal of Antimicrobial Chemotherapy, 62:437-441.
U.S. Office Action, Aug. 2, 2010, Guangwen Wei, U.S. Appl. No. 12/369,005, filed Feb. 11, 2009.
U.S. Notice of Allowance and Fee(s) Due, Jul. 29, 2010, for Guangwen Wei, U.S. Appl. No. 12/105,455, filed Apr. 18, 2008.
Chinese Office Action, Aug. 25, 2010, for Guangwen Wei, Chinese Application No. 200680007733.1, Filed Sep. 10, 2007.
Chinese Examination Report, Aug. 25, 2010, Guangwen Wei, Chinese Application No. 200680007733.1, Filed Sep. 10, 2007.
Japanese Examiners Report, Dec. 28, 2010, Sichuan Biotechnology Research Center, Japanese Patent Application No. 2006-524916, Filed Feb. 27, 2006.
U.S. Office Action, Dec. 22, 2010, for Guangwen Wei, U.S. Appl. No. 12/554,297, filed Sep. 4, 2009.
Jia, Liu Yun-peng, et al., 2007, "Meta-analysis of induction chemotherapy combined with interferon in small lung cancer", Chinese Journal of Practical Internal Medicine, 613-616.
Jin Bo et al., 2006, "Meta-analysis of induction chemotherapy combined with interferon in Advanced Non-small Cell Lung Cancer", Department of Medical Oncology, the First Affiliated Hospital of China Medical University, Shenyang 110001, China, pp. 370-375.
Hu Xue-jun et al., 2006, "Meta-analysis of Maintenance Therapy With Interferon for Small Cell Lung Cancer", Chin J Evid-based Med, 6(11):809-814.
Australian Office Action, Mar. 28, 2011, Guangwen Wei, Australian Application No. 2006257286, Filed Aug. 8, 2007.
European Search Report for Huiyangtech (USA), Inc., Apr. 26, 2011, Application No. EP 10 19 3126.
European Examiners Report, Jan. 14, 2011, Sichuan Biotechnology Research Center, European Patent Application No. EP 04809634.1, Filed Mar. 23, 2006.
Gao Zhan-Cheng et al., 2003, "Clinical investigation of outbreak of nosocomial severe acute respiratory syndrome", Database Medline, Database accession No. NLM12837162.
Loufty et al., 2003, "Interferon Alfacon-1 Plus Corticosteroids in Severe Acute Respiratory Syndrome—A preliminary Study", JAMA, 290(24):3222-3228.
Spada S., 2004, "Infergen", Directory of Approved Biopharmaceutic. Prod., 116-117.
Canadian Office Action, Mar. 8, 2011, Sichuan Biotechnolgy Research Center, Canadian Applicathon No. 2,439,503, Filed Aug. 27, 2003.
Krogsgaard et al., 1996, "Relation between efficacy and cumulative dose of alpha in interferon in chronic hepatitis B. European Concerted Action on Viral Hepatitis (Eurohep)", J Hepatology, 25(6):795-802.
Canadian Office Action, May 10, 2011, Huiyangtech (USA), Inc, Canadian Application No. 2,535,982, Filed Feb. 15, 2006, corresponding to Intl App'l No. PCT/US2004/028067, Filed Aug. 26, 2004.
Japanese Office Action, Sep. 27, 2011, Guangwen Wei, Japanese Patent Application No. 2008-500294, Filed Mar. 9, 2006.
U.S. Office Action, Sep. 27, 2011, Guangwen Wei, U.S. Appl. No. 12/369,005, filed Aug. 26, 2004.
U.S. Office Action, Jan. 25, 2011, Guangwen Wei, U.S. Appl. No. 10/928,474, filed Aug. 26, 2004.
U.S. Office Action, Oct. 5, 2011, Wei et. al., U.S. Appl. No. 13/019,044, filed Feb. 1, 2011.
Australian Office Action, Oct. 3,2011, Guangwen Wei, Australia Application No. 2006257286, Filed Aug. 8, 2007.
U.S. Office Action, Oct. 11,2011, Guangwen Wei, U.S. Appl. No. 12/105,455, Filed Apr. 18, 2008.
EPO Office Action, Oct. 25,2011, Huiyangtech (USA), Inc., Application No. EP 04809634, Filed Aug. 26, 2004.
Indian Office Action, Oct. 25,2011, Guangwen Wei, Indian Application No. 1214/MUMNP/2007, Filed Aug. 13, 2007.
Chinese Decision About the Reexamination, Nov. 10, 2011, Guangwen Wei, Chinese Application No. 200680007733.1, Filed Mar. 9, 2006.
Korean Office Action, Oct. 28,2011, Guangwen Wei, Korean Application No. 10-2006-7003699, Filed Feb. 23,2006.
Japanese Decision of Rejection, Feb. 1, 2012, Guangwen Wei, Japanese Application No. 2006-524916, Filed Apr. 18, 2008.
CAS No. 118390-30-0 (Jan. 13, 1989, STN entry date).
Supplementary European Search report, Feb. 23, 2012, Guangwen Wei, European Application No. 06795349.7, Filed Oct. 4, 2007.
Overexpression of a synthetic gene encoding human alpha interferon in *Escherichia cdi*, Protein Expression & purification 35(2004) 353-359.
Improvement of human interferon HUIFNα2 and HCV core protein expression levels in *Escherichia coli* but not of HUIFNα8 by using the tRNA AGA/AGG, BBRC, 296(2002) 1303-1309.
Expression of synthetic human interferon-α1 gene with modified nucleotide sequence in mammalian cells, Gene, 46(1986) 89-95.
Chinese Office Action, Notification of Grant, Mar. 2, 2012, Chinese Application No. 200680007733.1, Filed Mar. 9,2006.
Indian Office Action, Abandons application due to not meeting requirements, Mar. 20,2012, Indian Application No. 1214/MUMNP/ 2007, Filed Aug. 13, 2007.
U.S.A. Office Action, Notice of Allowance and Fees, Mar. 30,2012, U.S. Appl. No. 12/554,297, filed Sep. 4,2009).
TaiPei Office Action, Notification of Opinion on Examination, Apr. 27, 2012, TW Application No. 95107930, Filed Mar. 9,2006.
Malaysia Office Action, Substantive Examination, May 17, 2012, MY Application No. 20061015, Filed Mar. 9,2006.
U.S.A. Office Action (Restriction Requirement), Jul. 13, 2012, Guangwen Wei, U.S. Appl. No. 12/905,149, filed Oct. 15, 2010.
Canadian Examiners Report, Aug. 9,2012, Guangwen Wei, Canadian Application No. 2597317, Filed Aug. 9,2007.
U.S.A. Office Action, Aug. 13,2012, Guangwen Wei, U.S. Appl. No. 11/817,926, filed Sep. 6, 2007.
U.S.A. Office Action (Final), Aug. 29, 2012, Guangwen Wei, U.S. Appl. No. 13/019,044, filed Feb. 1, 2011.
Japanese Decision of Rejection, Sep. 5, 2012, Guangwen Wei, Japanese Application No. 2008-500294, Filed Sep. 6, 2007.
Canadian Examiner's Report, Oct. 17, 2012, Guangwen Wei, Canadian Application No. 2535982, Filed Feb. 15, 2006.
Boshoff et al, 2002, AIDS-related Malignancies. Nature Reviews Cancer. 2 373-382.
The extended European search report, Jan. 13,2013, Guangwen Wei, European Application No. 12184773.5, Filed Sep. 18, 2012.
Experimental therapy of filovirus infections, Apr. 1, 2002, Mike Bray et al., Antiviral Research, vol. 54, No. 1, pp. 1-17.
Chinese Office Action, Jan. 23,2013, Guangwen Wei, Chinese Application No. 201110206828.9, Filed Jul. 22, 2011.
Korean Office Action, Feb. 15,2013, Guangwen Wei, Korean Application No. 10-2007-7020614, Filed Sep. 7, 2007.

* cited by examiner

Figure 1

```
5'              11         21         31         41         51
 +1   M  C  D   L  P  Q  T   H  S  L   G  N  R   R  A  L  I   L  L  A
  1  ATGTGCGACC TGCCGCAGAC CCACTCCCTG GGTAACCGTC GTGCTCTGAT CCTGCTGGCT
     TACACGCTGG ACGGCGTCTG GGTGAGGGAC CCATTGGCAG CACGAGACTA GGACGACCGA

5'              71         81         91        101        111
 +1   Q  M  R   R  I  S  P   F  S  C   L  K  D   R  H  D  F   G  F  P
 61  CAGATGCGTC GTATCTCCCC GTTCTCCTGC CTGAAAGACC GTCACGACTT CGGTTTCCCG
     GTCTACGCAG CATAGAGGGG CAAGAGGACG GACTTTCTGG CAGTGCTGAA GCCAAAGGGC

5'             131        141        151        161        171
 +1      Q  E  E   F  D  G  N   Q  F  Q   K  A  Q   A  I  S  V   L  H  E
121  CAGGAAGAAT TCGACGGTAA CCAGTTCCAG AAAGCTCAGG CTATCTCCGT TCTGCACGAA
     GTCCTTCTTA AGCTGCCATT GGTCAAGGTC TTTCGAGTCC GATAGAGGCA AGACGTGCTT

5'             191        201        211        221        231
 +1   M  I  Q   Q  T  F  N   L  F  S   T  K  D   S  S  A  A   W  D  E
181  ATGATCCAGC AGACCTTCAA CCTGTTCTCC ACCAAAGACT CCTCCGCTGC TTGGGACGAA
     TACTAGGTCG TCTGGAAGTT GGACAAGAGG TGGTTTCTGA GGAGGCGACG AACCCTGCTT

5'             251        261        271        281        291
 +1   S  L  L   E  K  F  Y   T  E  L   Y  Q  Q   L  N  D  L   E  A  C
241  TCCCTGCTGG AAAAATTCTA CACCGAACTG TACCAGCAGC TGAACGACCT GGAAGCTTGC
     AGGGACGACC TTTTTAAGAT GTGGCTTGAC ATGGTCGTCG ACTTGCTGGA CCTTCGAACG

5'             311        321        331        341        351
 +1   V  I  Q   E  V  G  V   E  E  T   P  L  M   N  V  D  S   I  L  A
301  GTTATCCAGG AAGTTGGTGT TGAAGAAACC CCGCTGATGA ACGTTGACTC CATCCTGGCT
     CAATAGGTCC TTCAACCACA ACTTCTTTGG GGCGACTACT TGCAACTGAG GTAGGACCGA

5'             371        381        391        401        411
 +1   V  K  K   Y  F  Q  R   I  T  L   Y  L  T   E  K  K  Y   S  P  C
361  GTTAAAAAAT ACTTCCAGCG TATCACCCTG TACCTGACCG AAAAAAAATA CTCCCCGTGC
     CAATTTTTTA TGAAGGTCGC ATAGTGGGAC ATGGACTGGC TTTTTTTTAT GAGGGGCACG

5'             431        441        451        461        471
 +1   A  W  E   V  V  R  A   E  I  M   R  S  F   S  L  S  T   N  L  Q
421  GCTTGGGAAG TTGTTCGTGC TGAAATCATG CGTTCCTTCT CCCTGTCCAC CAACCTGCAG
     CGAACCCTTC AACAAGCACG ACTTTAGTAC GCAAGGAAGA GGGACAGGTG GTTGGACGTC

5'             491        501
 +1   E  R  L   R  R  K  E  #     (SEQ ID NO.1)
481  GAACGTCTGC GTCGTAAAGA ATAA    (SEQ ID NO.2)
     CTTGCAGACG CAGCATTTCT TATT    (SEQ ID NO.3)
```

Figure 2A

```
     5'          11          21          31          41          51
+1    M  C  D  L  P  Q  T  H  S  L  G  N  R  R  A  L  I  L  L  A
  1  ATGTGTGATT TACCTCAAAC TCATTCTCTT GGTAACCGTC GCGCTCTGAT TCTGCTGGCA
     TACACACTAA ATGGAGTTTG AGTAAGAGAA CCATTGGCAG CGCGAGACTA AGACGACCGT

5'          71          81          91         101         111
+1    Q  M  R  R  I  S  P  F  S  C  L  K  D  R  H  D  F  G  F  P
 61  CAGATGCGTC GTATTTCCCC GTTTAGCTGC CTGAAAGACC GTCACGACTT CGGCTTTCCG
     GTCTACGCAG CATAAAGGGG CAAATCGACG GACTTTCTGG CAGTGCTGAA GCCGAAAGGC

5'         131         141         151         161         171
+1    Q  E  E  F  D  G  N  Q  F  Q  K  A  Q  A  I  S  V  L  H  E
121  CAAGAAGAGT TCGATGGCAA CCAATTCCAG AAAGCTCAGG CAATCTCTGT ACTGCACGAA
     GTTCTTCTCA AGCTACCGTT GGTTAAGGTC TTTCGAGTCC GTTAGAGACA TGACGTGCTT

5'         191         201         211         221         231
+1    M  I  Q  Q  T  F  N  L  F  S  T  K  D  S  S  A  A  W  D  E
181  ATGATCCAAC AGACCTTCAA CCTGTTTTCC ACTAAAGACA GCTCTGCTGC TTGGGACGAA
     TACTAGGTTG TCTGGAAGTT GGACAAAAGG TGATTTCTGT CGAGACGACG AACCCTGCTT

5'         251         261         271         281         291
+1    S  L  L  E  K  F  Y  T  E  L  Y  Q  Q  L  N  D  L  E  A  C
241  AGCTTGCTGG AGAAGTTCTA CACTGAACTG TATCAGCAGC TGAACGACCT GGAAGCATGC
     TCGAACGACC TCTTCAAGAT GTGACTTGAC ATAGTCGTCG ACTTGCTGGA CCTTCGTACG

5'         311         321         331         341         351
+1    V  I  Q  E  V  G  V  E  E  T  P  L  M  N  V  D  S  I  L  A (SEQ ID NO.4)
301  GTAATCCAGG AAGTTGGTGT AGAAGAGACT CCGCTGATGA ACGTCGACTC TATTCTGGCA (SEQ ID NO.5)
     CATTAGGTCC TTCAACCACA TCTTCTCTGA GGCGACTACT TGCAGCTGAG ATAAGACCGT (SEQ ID NO.6)
```

Figure 2B

```
5'            11          21          31          41          51
+1  M  C  D    L  P  Q  T    H  S  L    G  N  R    R  A  L  I    L  L  A
 1  ATGTGTGATT TACCTCAAAC TCATTCTCTT GGTAACCGTC GCGCTCTGAT TCTGCTGGCA
    TACACACTAA ATGGAGTTTG AGTAAGAGAA CCATTGGCAG CGCGAGACTA AGACGACCGT

5'            71          81          91         101         111
+1  Q  M  R    R  I  S  P    F  S  C    L  K  D    R  H  D  F    G  F  P
61  CAGATGCGTC GTATTTCCCC GTTTAGCTGC CTGAAAGACC GTCACGACTT CGGCTTTCCG
    GTCTACGCAG CATAAAGGGG CAAATCGACG GACTTTCTGG CAGTGCTGAA GCCGAAAGGC

5'           131         141         151         161         171
+1   Q  E  E    F  D  G  N    Q  F  Q    K  A  Q    A  I  S  V    L  H  E
121 CAAGAAGAGT TCGATGGCAA CCAATTCCAG AAAGCTCAGG CAATCTCTGT ACTGCACGAA
    GTTCTTCTCA AGCTACCGTT GGTTAAGGTC TTTCGAGTCC GTTAGAGACA TGACGTGCTT

5'           191         201         211         221         231
+1  M  I  Q    Q  T  F  N    L  F  S    T  K  D    S  S  A  A    W  D  E
181 ATGATCCAAC AGACCTTCAA CCTGTTTTCC ACTAAAGACA GCTCTGCTGC TTGGGACGAA
    TACTAGGTTG TCTGGAAGTT GGACAAAAGG TGATTTCTGT CGAGACGACG AACCCTGCTT

5'           251         261         271         281         291
+1   S  L  L    E  K  F  Y    T  E  L    Y  Q  Q    L  N  D  L    E  A  C
241 AGCTTGCTGG AGAAGTTCTA CACTGAACTG TATCAGCAGC TGAACGACCT GGAAGCATGC
    TCGAACGACC TCTTCAAGAT GTGACTTGAC ATAGTCGTCG ACTTGCTGGA CCTTCGTACG

5'           311         321         331         341         351
+1  V  I  Q    E  V  G  V    E  E  T    P  L  M    N  V  D  S    I  L  A
301 GTAATCCAGG AAGTTGGTGT AGAAGAGACT CCGCTGATGA ACGTCGACTC TATTCTGGCA
    CATTAGGTCC TTCAACCACA TCTTCTCTGA GGCGACTACT TGCAGCTGAG ATAAGACCGT

5'           371         381         391         401         411
+1  V  K  K    Y  F  Q  R    I  T  L    Y  L  T    E  K  K  Y    S  P  C
361 GTTAAAAAGT ACTTCCAGCG TATCACTCTG TACCTGACCG AAAAGAAATA TTCTCCGTGC
    CAATTTTTCA TGAAGGTCGC ATAGTGAGAC ATGGACTGGC TTTTCTTTAT AAGAGGCACG

5'           431         441         451         461         471
+1   A  W  E    V  V  R  A    E  I  M    R  S  F    S  L  S  T    N  L  Q
421 GCTTGGGAAG TAGTTCGCGC TGAAATTATG CGTTCTTTCT CTCTGTCTAC TAACCTGCAG
    CGAACCCTTC ATCAAGCGCG ACTTTAATAC GCAAGAAAGA GAGACAGATG ATTGGACGTC

5'           491         501
+1   E  R  L    R  R  K  E    #       (SEQ ID NO.7)
481 GAGCGTCTGC GCCGTAAAGA ATAATAG     (SEQ ID NO.8)
    CTCGCAGACG CGGCATTTCT TATTATC    (SEQ ID NO.9)
```

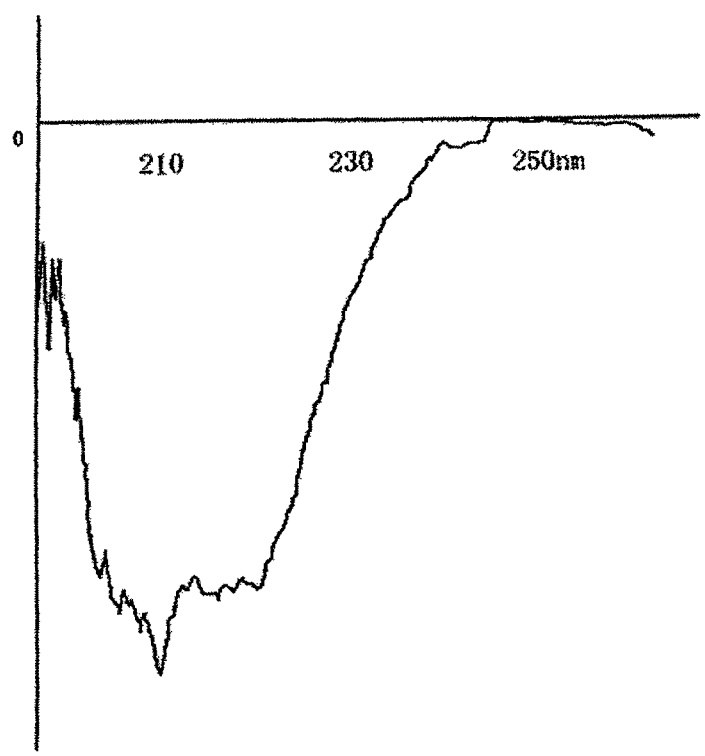
Figure 6-A

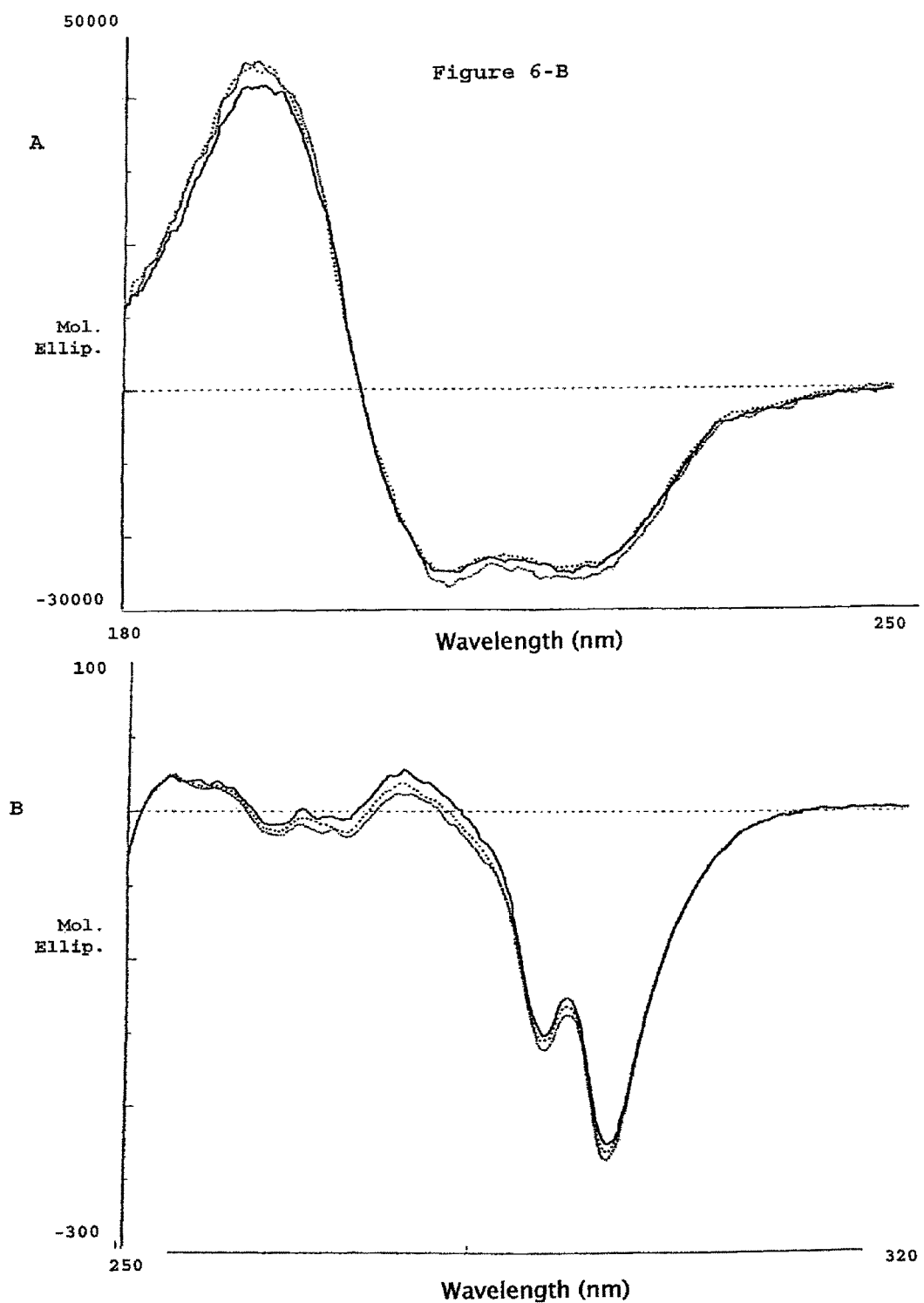

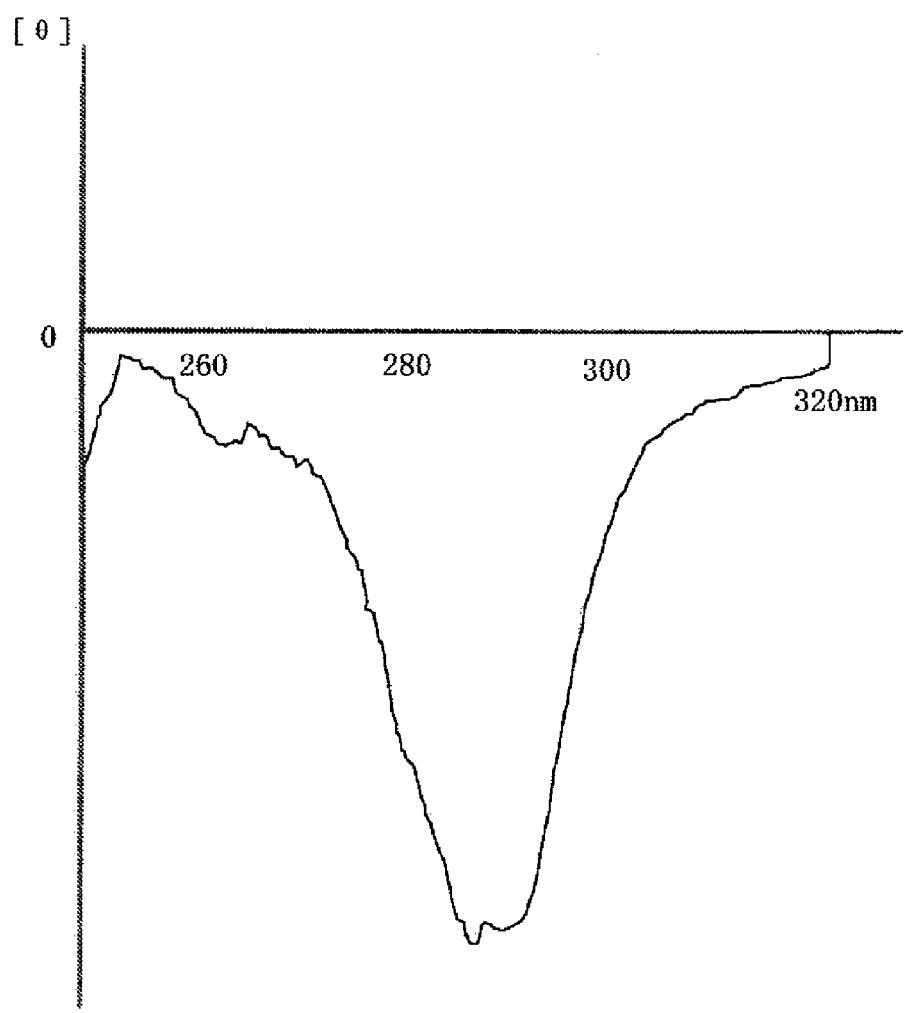
Figure 6-C

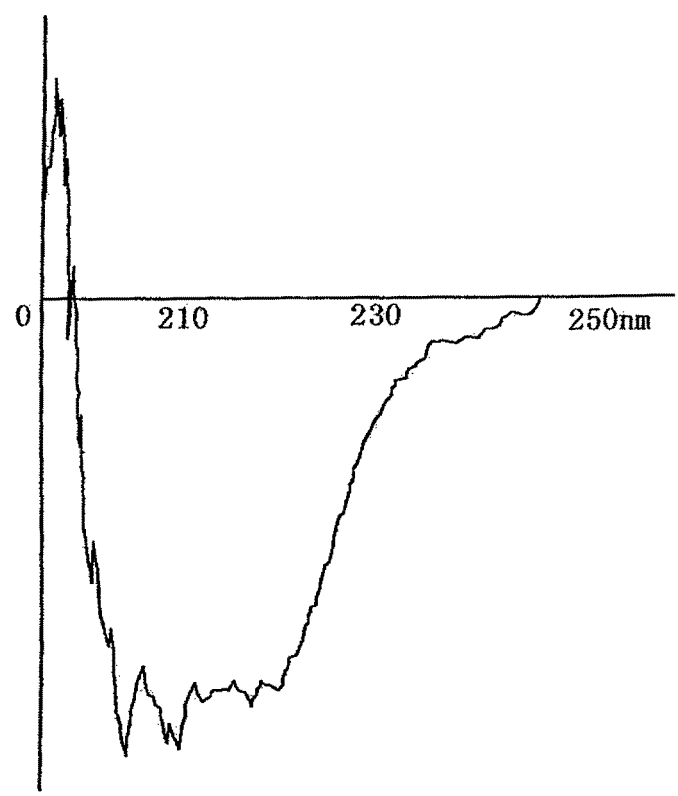
Figure 6-D

Figure 11A:
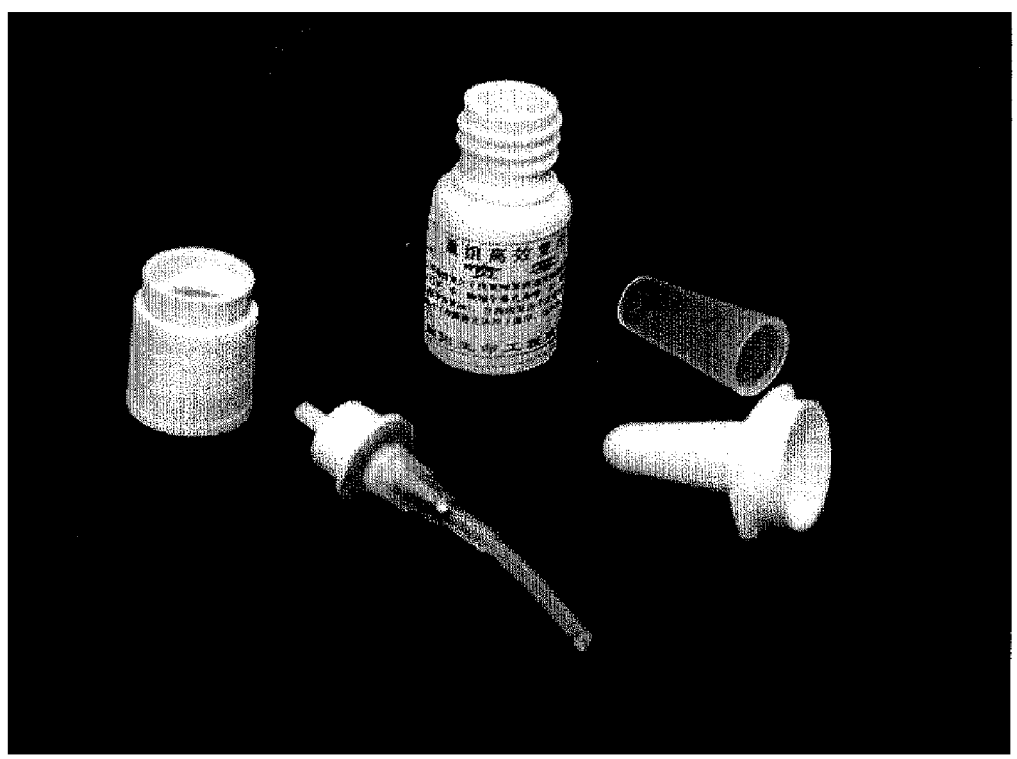
Figures 1, 13A:
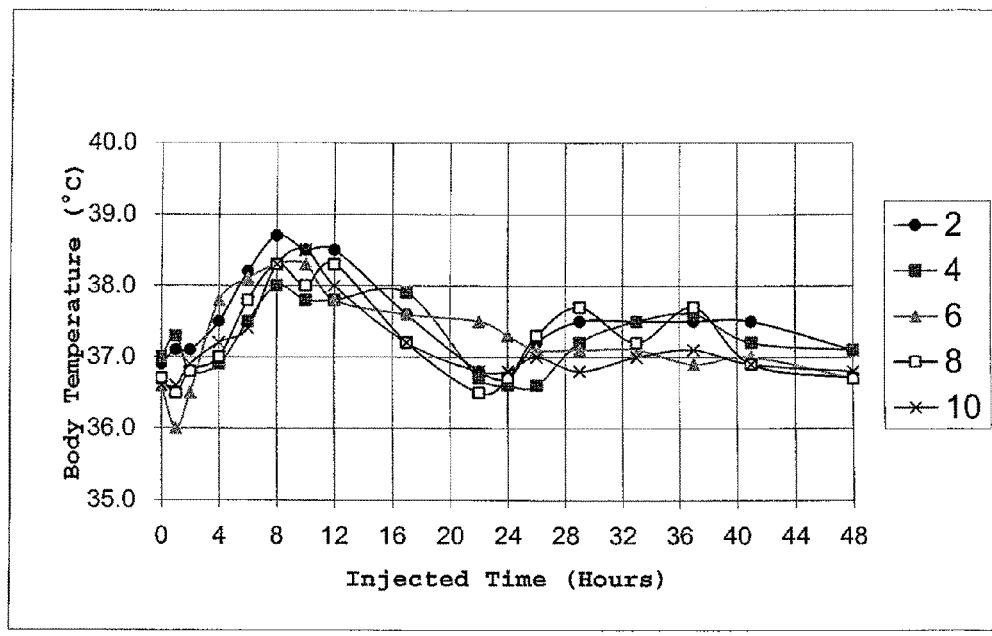

Figure 11D
1. Pre-spray
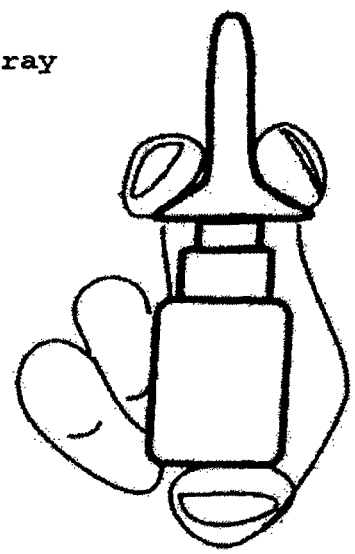
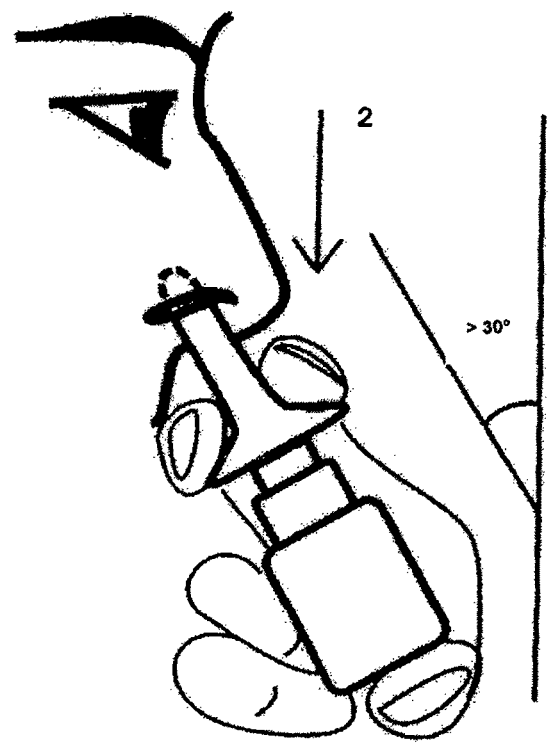

Anti-SARS Activity of Interferons

Figure 16
Inhibition of Influenza Infection (24 Hours)
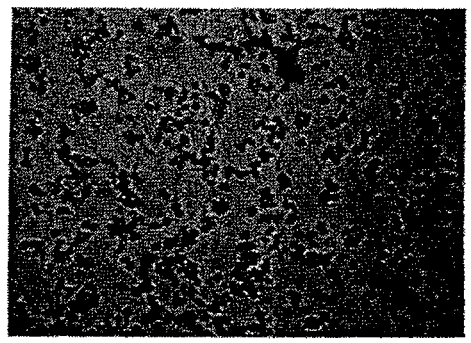 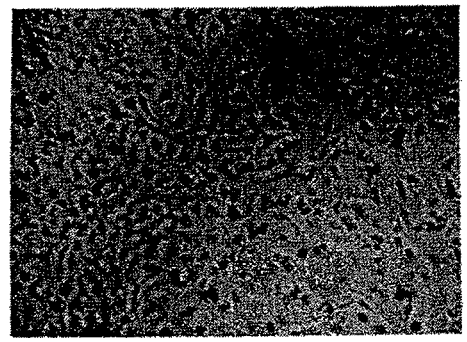
Untreated — 10 ng/ml

Figure 17-A

Experimental center of west china second university hospital
The report of tumor examination

NO. :   200407140156

| Name | | Sex  female | Age  42 | Section office: Gynecology | Bed No  8-+9 | Code in hospital  162528 |
|---|---|---|---|---|---|---|
| Clinical diagnosis: Ovarian cancer? | | | | | Sample type | serum |

| AxSYM full automic immuno-device MEIA method | | | Tumor examination | |
|---|---|---|---|---|
| Item | Result | Unit | Normal data negative | |
| AFP |  | ng/ml | < 10.9 | ng/ml |
| CEA |  | ng/ml | < 10.0 | ng/ml |
| CA-125 | >600 | U/ml | < 35 | U/ml |
| CA-199 | 1 | U/ml | < 37 | U/ml |
| hCG |  | U/ml | < 10 | U/ml |
| CA-153 | >250 | U/ml | < 28 | U/ml |
| T-PSA |  | ng/ml | <4.0 | ng/ml |

Remark:

Examine date: 14th Jul, 2004       Signatory: Hebing

Report date: 14th Jul, 2004        Check:

TEL:85558649

Figure 17-B

Uterus:
Uterus anteposition, anteroposterior diameter:4.3cm, endometrium thickness:0.5cm, the echo of muscular wall was equality
Uterine adnexa:
There was 5.6×4.5×6.6cm disjunctive-shaped hybridism occupation in left Uterine adnexa, with cystic echo
Right ovary 4.1×2.5×3.4cm,the 1.9cm entity echo was observed in right ovary
5.4cm Fluidity area opaca was observed among intestine Examination prompt hybridism occupation in left Uterine adnexa(be suspicious of ovary tumor )
right ovary enlarged
ascetic fluid Medicine channel Please keep this report carefully and carry while return visit Tel:

Shijinshi Soft ware            Type date: 12:16 PM in 14ᵗʰ Jul 2004

Figure 17-C

West china university hospital Pathological diagnosis report

Name ..................... Age ...42........ Sex ....female..... NoC20040321/T20040836....
Hospital Second hospital.. Section office ..Gynecology... Bed No .....8-18.... Code in hospital .....162528........

C: <ascetic fluid>malignant tumor cells were observed, be inclined to low-degree differentiation adenocarcinoma cells T: < ascetic fluid > low-degree differentiation adenocarcinoma cells were observed Doctor: _____                                   Report date: 16th Jul, 2004

Figure 17-D

Pathological department of hospital of Si-chuan province
fine needle aspiration cytology report
No: N2320-04

Name ............  Sex ...female...  Age ...42...
Hospital name ............  Department ............  Bed No ............  Code in hospital ............

Cyropathology

Fine needle aspiration by left breast: breast cancer (suggested that freeze in course of operation)

The diagnosis is refered to examined specimen only

Diagnostic Doctor: Daxue Hu 
Report date: 16th Jul, 2004

Return visit doctor:

Figure 17-E

West china second university hospital
Pathological diagnosis report

Receive date: 3rd Aug 2004      No: B200407224

| Name | | Sex | female | Age | 42 |
|------|---|-----|--------|-----|-----|
| Hospital | Second hospital | Section office | Gynecology | Bed.No | 8-8 |
| Code in hospital | 162528 | Specimen: the enclosed, caul, lymph node of pelvic cavity | | | |

Clinical diagnosis: ovarian carcinoma, breast cancer

Main affection:

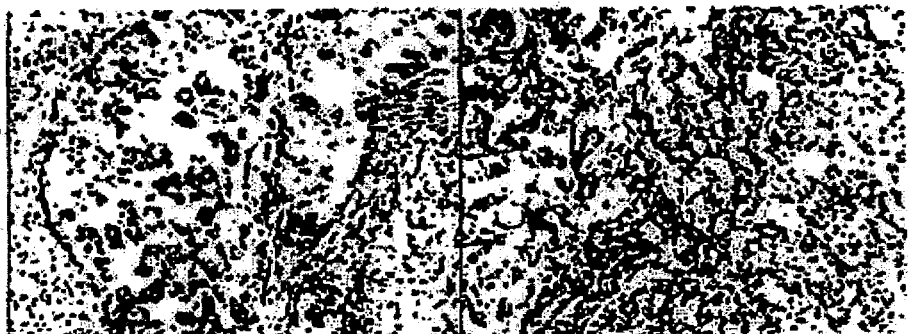

Pathological diagnosis:

1. Lower differentiation nipple-shaped adenocarcinoma of ovary (both lateral), accompany by secretion. Mostly metastasis(metastasize from breast cancer, consider the result combined with clinical situation). Carcinoma was found in the wall of oviduct(both lateral), muscular layer of uterus, and interstial muscular layer of cervix (carcinoma embolus was observed in tube, as found in freezing-microtomyF20041773), the wall of bilateral pelvic cavity, (the front wall of rectum), (caul), (left sacrum ligaments); metastasize to lymph nodes as below:(right femoral deep)2/4, (left obrurator)5/10, (right internal and external iliac )6/6,(left femoral deep)4/5, (abdominal aorta)15/15,(left common iliac)7/7, (right common iliac)4/4,(right obruuator)6/8.
2. uterus multiple leimyoma
3. proliferative endometrium
4. chronic cervicitis ,cervix endometritis attending by retention cyst
5. there were no remarkable lesion around bilateral uterus
6. bilateral chronic salpingitis after freezingF20041773:there were cancer embolus of internal vessel in muscular layer of uterus, and interstial muscular layer of cervix after freezingF20041771:<bilateral ovary and left sacrum ligament node> were attacked by low-degree differentiation adenocarcinoma, accompany by necrosis.

(according to the description in medical history that a little carcinoma cells and sphacelus were observed in fluid sucked by left breast, confirming whether the left breast is the primary region of carcinoma is important.)

Doctor: Yi-tang Li   Section maker: Shi-ying long   typist: Qian li   Report date: 5th Aug. 2005

Figure 17-F

West china university hospital
Pathological diagnosis report

PACS号 0417693

| Name | | Age 42岁 | Sex female | No 0417693 |
|---|---|---|---|---|
| Hospital | Second hospital | Section office | Bed No | Code in hospital |

Diagnosis :

<ovarian> serosity cystadenocarinoma

Doctor: Xian-liang zhang                                Report date: 4th Aug 2004

The diagnosis is refered to examined specimen only          Type date: 4th Aug 2004 14:46:39

Address: pathological department of West china university hospital, No 37 Guo-xue street , Chengdu Postal code:610041

Reception number:028-85422698

Rogatory number:028-85422700

Outpatient cyto-pathological department:028-85422705

Doctor on duty:028-85422701

Pathological technical office:028-85422643

Figure 17-G

Experimental center of west china second university Hospital
The report of tumor examination

NO: 201712250013

| Name: | Sex | female | Age | 42 | Section office: | Bed No | Code in hospital |
|---|---|---|---|---|---|---|---|
| Clinical diagnosis | | | | | | Sample type | serum |

| AxSYM full automic immuno-device MEIA method | | | Tumor examination | |
|---|---|---|---|---|
| Item | Result | Unit | Normal data negative | |
| AFP | | ng/ml | < 10.9 | ng/ml |
| CEA | | ng/ml | < 10.0 | ng/ml |
| CA-125 | 5 | U/ml | < 35 | U/ml |
| CA-199 | | U/ml | < 37 | U/ml |
| hCG | | U/ml | < 10 | U/ml |
| CA-153 | 13 | U/ml | < 28 | U/ml |
| T-PSA | | ng/ml | <4.0 | ng/ml |

Remark:

Examine date: 25th Dec 2004        Signatory: Hebing

Report date: 27th Dec 2004          Check:

TEL:85558649

Figure 17-H

PET center of daping hospital of third Military Medical University
PET(Positron emission tomography) report

| Examine date: 25th Feb 2005 | Examine NO: P713 |

Name:  Sex: 女  Age:43
Hospital:  Section office:  Hospital No:

Clinical diagnose: postoperative of left ovarian carcinoma   Examine item: system and brain Developer: 18F-FDG   Dosage: 14.8 mCi   Administration: intravenous injection Result:
After fasting, 18F-FDG(14.8mCi) was injected. Besides lying and relaxing, avoiding-illumination was needed. Developed the brain after 50 minutes, clear image was acquired. Both raise and reduce of radioactivity were not found in both pallium, cerebellum and basal ganglia.

Developed the whole body after 60 minutes, clear image was acquired. Both raise and reduce of radioactivity were not found in cervix,bilateral lung, mediastinum, liver, adrenal gland, lymph node of abdominal cavity, pelvic cavity and bones. Cardiac muscle was developed equably.

Diagnosis:
postoperative of left ovarian carcinoma, there were no abnormal FDG metabolism in whole body and brain Doctor: 
Date: 25th Feb 2005

This report for clinician use only

SEQUENCE LISTING

```
<160> NUMBER OF SEQ ID NOS: 17

<210> SEQ ID NO 1
<211> LENGTH: 167
<212> TYPE: PRT
<213> ORGANISM: Artificial Sequence
<220> FEATURE:
<223> OTHER INFORMATION: sequence for a recombinant human interferon

<400> SEQUENCE: 1

Met Cys Asp Leu Pro Gln Thr His Ser Leu Gly Asn Arg Arg Ala
1               5                   10                  15

Leu Ile Leu Leu Ala Gln Met Arg Arg Ile Ser Pro Phe Ser Cys
                20                  25                  30

Leu Lys Asp Arg His Asp Phe Gly Phe Pro Gln Glu Glu Phe Asp
                35                  40                  45

Gly Asn Gln Phe Gln Lys Ala Gln Ala Ile Ser Val Leu His Glu
                50                  55                  60

Met Ile Gln Gln Thr Phe Asn Leu Phe Ser Thr Lys Asp Ser Ser
                65                  70                  75

Ala Ala Trp Asp Glu Ser Leu Leu Glu Lys Phe Tyr Thr Glu Leu
                80                  85                  90

Tyr Gln Gln Leu Asn Asp Leu Glu Ala Cys Val Ile Gln Glu Val
                95                  100                 105

Gly Val Glu Glu Thr Pro Leu Met Asn Val Asp Ser Ile Leu Ala
                110                 115                 120

Val Lys Lys Tyr Phe Gln Arg Ile Thr Leu Tyr Leu Thr Glu Lys
                125                 130                 135

Lys Tyr Ser Pro Cys Ala Trp Glu Val Val Arg Ala Glu Ile Met
```

```
                    140                 145                 150
Arg Ser Phe Ser Leu Ser Thr Asn Leu Gln Glu Arg Leu Arg Arg
                155                 160                 165

Lys Glu

<210> SEQ ID NO 2
<211> LENGTH: 504
<212> TYPE: DNA
<213> ORGANISM: Artificial Sequence
<220> FEATURE:
<223> OTHER INFORMATION: coding for a recombinant human interferon

<400> SEQUENCE: 2
atgtgcgacc tgccgcagac ccactccctg ggtaaccgtc gtgctctgat cctgctggct      60
cagatgcgtc gtatctcccc gttctcctgc ctgaaagacc gtcacgactt cggtttcccg     120
caggaagaat tcgacggtaa ccagttccag aaagctcagg ctatctccgt tctgcacgaa     180
atgatccagc agaccttcaa cctgttctcc accaaagact cctccgctgc ttgggacgaa     240
tccctgctgg aaaaattcta caccgaactg taccagcagc tgaacgacct ggaagcttgc     300
gttatccagg aagttggtgt tgaagaaacc ccgctgatga cgttgactc catcctggct      360 gttaaaaaat acttccagcg tatcaccctg tacctgaccg aaaaaaaata ctccccgtgc     420
gcttgggaag ttgttcgtgc tgaaatcatg cgttccttct ccctgtccac caacctgcag     480
gaacgtctgc gtcgtaaaga ataa                                           504

<210> SEQ ID NO 3
<211> LENGTH: 504
<212> TYPE: DNA
<213> ORGANISM: Artificial Sequence
<220> FEATURE:
<223> OTHER INFORMATION: coding for a recombinant human interferon

<400> SEQUENCE: 3
tacacgctgg acggcgtctg ggtgagggac ccattggcag cacgagacta ggacgaccga      60
gtctacgcag catagagggg caagaggacg gactttctgg cagtgctgaa gccaaagggc     120
gtccttctta agctgccatt ggtcaaggtc tttcgagtcc gatagaggca agacgtgctt     180
tactaggtcg tctggaagtt ggacaagagg tggtttctga ggaggcgacg aaccctgctt     240
agggacgacc tttttaagat gtggcttgac atggtcgtcg acttgctgga ccttcgaacg     300
caataggtcc ttcaaccaca acttctttgg ggcgactact tgcaactgag gtaggaccga     360
caatttttta tgaaggtcgc atagtgggac atggactggc tttttttttat gagggggcacg     420 cgaacccttc aacaagcacg actttagtac gcaaggaaga gggacaggtg gttggacgtc     480
cttgcagacg cagcatttct tatt                                           504

<210> SEQ ID NO 4
<211> LENGTH: 120
<212> TYPE: PRT
<213> ORGANISM: Artificial Sequence
<220> FEATURE:
<223> OTHER INFORMATION: sequence for a recombinant human interferon

<400> SEQUENCE: 4

Met Cys Asp Leu Pro Gln Thr His Ser Leu Gly Asn Arg Arg Ala
1               5                   10                  15

Leu Ile Leu Leu Ala Gln Met Arg Arg Ile Ser Pro Phe Ser Cys
                20                  25                  30

Leu Lys Asp Arg His Asp Phe Gly Phe Pro Gln Glu Glu Phe Asp
```

```
                35                  40                  45

Gly Asn Gln Phe Gln Lys Ala Gln Ala Ile Ser Val Leu His Glu
            50                  55                  60

Met Ile Gln Gln Thr Phe Asn Leu Phe Ser Thr Lys Asp Ser Ser
        65                  70                  75

Ala Ala Trp Asp Glu Ser Leu Leu Glu Lys Phe Tyr Thr Glu Leu
            80                  85                  90

Tyr Gln Gln Leu Asn Asp Leu Glu Ala Cys Val Ile Gln Glu Val
                95                 100                 105

Gly Val Glu Glu Thr Pro Leu Met Asn Val Asp Ser Ile Leu Ala
            110                 115                 120

<210> SEQ ID NO 5
<211> LENGTH: 360
<212> TYPE: DNA
<213> ORGANISM: Artificial Sequence
<220> FEATURE:
<223> OTHER INFORMATION: coding for a recombinant human interferon

<400> SEQUENCE: 5
atgtgtgatt tacctcaaac tcattctctt ggtaaccgtc gcgctctgat tctgctggca      60
cagatgcgtc gtatttcccc gtttagctgc ctgaaagacc gtcacgactt cggctttccg     120
caagaagagt tcgatggcaa ccaattccag aaagctcagg caatctctgt actgcacgaa     180
atgatccaac agaccttcaa cctgttttcc actaaagaca gctctgctgc ttgggacgaa     240
agcttgctgg agaagttcta cactgaactg tatcagcagc tgaacgacct ggaagcatgc     300
gtaatccagg aagttggtgt agaagagact ccgctgatga acgtcgactc tattctggca     360

<210> SEQ ID NO 6
<211> LENGTH: 360
<212> TYPE: DNA
<213> ORGANISM: Artificial Sequence
<220> FEATURE:
<223> OTHER INFORMATION: coding for a recombinant human interferon

<400> SEQUENCE: 6
tacacactaa atggagtttg agtaagagaa ccattggcag cgcgagacta agacgaccgt      60
gtctacgcag cataaagggg caaatcgacg gactttctgg cagtgctgaa gccgaaaggc     120
gttcttctca agctaccgtt ggttaaggtc tttcgagtcc gttagagaca tgacgtgctt     180
tactaggttg tctggaagtt ggacaaaagg tgatttctgt cgagacgacg aaccctgctt     240
tcgaacgacc tcttcaagat gtgacttgac atagtcgtcg acttgctgga ccttcgtacg     300
cattaggtcc ttcaaccaca tcttctctga ggcgactact tgcagctgag ataagaccgt     360

<210> SEQ ID NO 7
<211> LENGTH: 167
<212> TYPE: PRT
<213> ORGANISM: Artificial Sequence
<220> FEATURE:
<223> OTHER INFORMATION: sequence for a recombinant human interferon

<400> SEQUENCE: 7

Met Cys Asp Leu Pro Gln Thr His Ser Leu Gly Asn Arg Arg Ala
1               5                  10                  15

Leu Ile Leu Leu Ala Gln Met Arg Arg Ile Ser Pro Phe Ser Cys
            20                  25                  30

Leu Lys Asp Arg His Asp Phe Gly Phe Pro Gln Glu Glu Phe Asp
        35                  40                  45
```

```
Gly Asn Gln Phe Gln Lys Ala Gln Ala Ile Ser Val Leu His Glu
                 50                  55                  60

Met Ile Gln Gln Thr Phe Asn Leu Phe Ser Thr Lys Asp Ser Ser
             65                  70                  75

Ala Ala Trp Asp Glu Ser Leu Leu Glu Lys Phe Tyr Thr Glu Leu
         80                  85                  90

Tyr Gln Gln Leu Asn Asp Leu Glu Ala Cys Val Ile Gln Glu Val
     95                 100                 105

Gly Val Glu Glu Thr Pro Leu Met Asn Val Asp Ser Ile Leu Ala
                110                 115                 120

Val Lys Lys Tyr Phe Gln Arg Ile Thr Leu Tyr Leu Thr Glu Lys
            125                 130                 135

Lys Tyr Ser Pro Cys Ala Trp Glu Val Val Arg Ala Glu Ile Met
        140                 145                 150

Arg Ser Phe Ser Leu Ser Thr Asn Leu Gln Glu Arg Leu Arg Arg
    155                 160                 165

Lys Glu

<210> SEQ ID NO 8
<211> LENGTH: 507
<212> TYPE: DNA
<213> ORGANISM: Artificial Sequence
<220> FEATURE:
<223> OTHER INFORMATION: coding for a recombinant human interferon

<400> SEQUENCE: 8
atgtgtgatt tacctcaaac tcattctctt ggtaaccgtc gcgctctgat tctgctggca      60
cagatgcgtc gtatttcccc gtttagctgc ctgaaagacc gtcacgactt cggctttccg     120
caagaagagt tcgatggcaa ccaattccag aaagctcagg caatctctgt actgcacgaa     180
atgatccaac agaccttcaa cctgtttttcc actaaagaca gctctgctgc ttgggacgaa     240
agcttgctgg agaagttcta cactgaactg tatcagcagc tgaacgacct ggaagcatgc     300
gtaatccagg aagttggtgt agaagagact ccgctgatga acgtcgactc tattctggca     360
gttaaaaagt acttccagcg tatcactctg tacctgaccg aaaagaaata ttctccgtgc     420
gcttgggaag tagttcgcgc tgaaattatg cgttctttct ctctgtctac taacctgcag     480
gagcgtctgc gccgtaaaga ataatag                                         507

<210> SEQ ID NO 9
<211> LENGTH: 507
<212> TYPE: DNA
<213> ORGANISM: Artificial Sequence
<220> FEATURE:
<223> OTHER INFORMATION: coding for a recombinant human interferon

<400> SEQUENCE: 9
tacacactaa atggagtttg agtaagagaa ccattggcag cgcgagacta agacgaccgt      60
gtctacgcag cataaagggg caaatcgacg gactttctgg cagtgctgaa gccgaaaggc     120
gttcttctca agctaccgtt ggttaaggtc tttcgagtcc gttagagaca tgacgtgctt     180
tactaggttg tctggaagtt ggacaaaagg tgatttctgt cgagacgacg aaccctgctt     240
tcgaacgacc tcttcaagat gtgacttgac atagtcgtcg acttgctgga ccttcgtacg     300
cattaggtcc ttcaaccaca tcttctctga ggcgactact tgcagctgag ataagaccgt     360 caattttttca tgaaggtcgc atagtgagac atggactggc ttttcttttat aagaggcacg     420 cgaacccttc atcaagcgcg actttaatac gcaagaaaga gagacagatg attggacgtc     480
```
ctcgcagacg cggcatttct tattatc                                       507

<210> SEQ ID NO 10
<211> LENGTH: 108
<212> TYPE: DNA
<213> ORGANISM: Artificial Sequence
<220> FEATURE:
<223> OTHER INFORMATION: Synthetic oligomer

<400> SEQUENCE: 10
atgtgcgacc tgccgcagac ccactccctg ggtaaccgtc gtgctctgat cctgctggct    60
cagatgcgtc gtatctcccc gttctcctgc ctgaaagacc gtcacgac                108

<210> SEQ ID NO 11
<211> LENGTH: 108
<212> TYPE: DNA
<213> ORGANISM: Artificial Sequence
<220> FEATURE:
<223> OTHER INFORMATION: Synthetic oligomer

<400> SEQUENCE: 11
ctgaaagacc gtcacgactt cggtttcccg caggaagaat cgacggtaa ccagttccag     60 aaagctcagg ctatctccgt tctgcacgaa atgatccagc agccttc                 108

<210> SEQ ID NO 12
<211> LENGTH: 103
<212> TYPE: DNA
<213> ORGANISM: Artificial Sequence
<220> FEATURE:
<223> OTHER INFORMATION: Synthetic oligomer

<400> SEQUENCE: 12
gctgctggta cagttcggtg tagaattttt ccagcaggga ttcgtcccaa gcagcggagg    60
agtctttggt ggagaacagg ttgaaggtct gctggatcat ttc                     103

<210> SEQ ID NO 13
<211> LENGTH: 103
<212> TYPE: DNA
<213> ORGANISM: Artificial Sequence
<220> FEATURE:
<223> OTHER INFORMATION: Synthetic oligomer

<400> SEQUENCE: 13
atccctgctg gaaaaattct acaccgaact gtaccagcag ctgaacgacc tggaagcttg    60
cgttatccag gaagttggtg ttgaagaaac cccgctgatg aac                     103

<210> SEQ ID NO 14
<211> LENGTH: 106
<212> TYPE: DNA
<213> ORGANISM: Artificial Sequence
<220> FEATURE:
<223> OTHER INFORMATION: Synthetic oligomer

<400> SEQUENCE: 14
gaagaaaccc cgctgatgaa cgttgactcc atcctggctg ttaaaaaata cttccagcgt    60 atcacccctgt acctgaccga aaaaaaatac tccccgtgcg cttggg                 106

<210> SEQ ID NO 15
<211> LENGTH: 112
<212> TYPE: DNA
<213> ORGANISM: Artificial Sequence
<220> FEATURE:
<223> OTHER INFORMATION: Synthetic oligomer

```
<400> SEQUENCE: 15
ttattcttta cgacgcagac gttcctgcag gttggtggac agggagaagg aacgcatgat      60
ttcagcacga acaacttccc aagcgcacgg ggagtatttt ttttcggtca gg             112

<210> SEQ ID NO 16
<211> LENGTH: 31
<212> TYPE: DNA
<213> ORGANISM: Artificial Sequence
<220> FEATURE:
<223> OTHER INFORMATION: Synthetic oligomer

<400> SEQUENCE: 16
atcggccata tgtgcgacct gccgcagacc c                                     31

<210> SEQ ID NO 17
<211> LENGTH: 40
<212> TYPE: DNA
<213> ORGANISM: Artificial Sequence
<220> FEATURE:
<223> OTHER INFORMATION: Synthetic oligomer

<400> SEQUENCE: 17
actgccaggc tgcagttatt ctttacgacg cagacgttcc                            40
```

TREATMENT OF TUMORS AND VIRAL DISEASES WITH RECOMBINANT INTERFERON ALPHA

The application is a continuation application of U.S. Ser. No. 11/077,813, filed Mar. 10, 2005, now abandoned, which is a continuation-in-part application of U.S. Ser. No. 10/927,975, filed Aug. 26, 2004, now abandoned, which is a continuation-in-part application of U.S. Ser. No. 10/650,365, filed Aug. 28, 2003, now issued as U.S. Pat. No. 7,364,724, which is a continuation-in-part of International Application No. PCT/CN02/00128, filed Feb. 28, 2002, which claims priority of Chinese Application No. 01104367.9, filed Feb. 28, 2001. The contents of the above applications are hereby incorporated in their entireties by reference into this application.

Throughout this application, various publications are referenced. Disclosures of these publications in their entireties are hereby incorporated by reference into this application in order to more fully describe the state of the art to which this invention pertains.

FIELD OF THE INVENTION

This invention is related to a field of bioengineering. Specifically this invention relates to a recombinant super-compound interferon (rSIFN-co) or its equivalent with changed spatial configuration, high efficacy and low side effects. Therefore, high dose of rSIFN-co may be used. This invention also relates to a process to produce said super-compound interferon (rSIFN-co) or a pharmaceutical composition comprising said super-compound interferon (rSIFN-co) or its equivalent, and uses of said interferon or composition for anti-viral and anti-tumor therapy.

BACKGROUND OF THE INVENTION

IFN-con is a new interferon molecule constructed with the most popular conservative amino acid found in natural human IFN-α subtypes using genetic engineering methods. U.S. Pat. Nos. 4,695,623 and 4,897,471 have described it. IFN-con had been proven to have broad-spectrum IFN activity and virus- and tumor-inhibition and natural killer cell activity. U.S. Pat. No. 5,372,808 by Amgen, Inc. addresses treatment Infergen® (interferon alfacon-1). Chinese Patent No. 97193506.8 by Amgen, Inc. addresses re-treatment of Infergen® (interferon alfacon-1) on hepatitis C. Chinese Patent No. 98114663.5 by Shenzhen Jiusheng Bio-engineering Ltd. addresses recombinant human consensus interferon-α treatment for hepatitis B and hepatitis C.

The United States Food and Drug Administration (FDA) authorized Amgen to produce Infergen® (interferon alfacon-1) with $E.\ Coli.$ for clinical hepatitis C treatment at the end of 1997.

Hepatitis B patients can be identified when detecting HBsAg and the HBeAg. IFN-α is commonly used in clinics to treat hepatitis B. IFN-α binds superficial cell membrane receptors, thus inhibiting DNA and RNA (ribonucleic acid) duplication and inducing some enzymes to prevent duplication of the virus in hepatitis-infected cells. All IFNs can inhibit DNA duplication of viruses, but they cannot inhibit the e and s antigen expression.

An outbreak of atypical pneumonia, referred to as severe acute respiratory syndrome (SARS) and first identified in Guangdong Province, China, has spread to several countries. Similar cases were detected in patients in Hong Kong, Vietnam, and Canada from February and March 2003. The World Health Organization (WHO) issued a global alert for the illness. In mid-March 2003, SARS was documented in health care workers and household members who had cared for patients with severe respiratory illness in the Far East. Many of these cases could be traced through multiple chains of transmission to one health care worker from Guangdong Province who visited Hong Kong, where he was hospitalized with pneumonia and died. By late April 2003, thousands of SARS cases and hundreds of SARS-related deaths from over 25 countries around the world were reported to WHO. Most of these cases occurred through exposure to SARS patients in household or health care settings. This invention provides a method to prevent and/or treat SARS. This disclosure describes recombinant super-compound interferon (rSIFN-co), method to produce the same and uses thereof. Particularly, the super-compound interferon disclosed herein is capable of inhibiting, preventing and/or treating the hepatitis viruses, SARS virus, or virus-induced upper respiratory diseases, the Influenza virus, for example Avian Influenza virus and Ebola virus.

In addition, rSIFN-co is effective in preventing and/or treating viral diseases and tumors with less side effects as compared to other available interferons.

SUMMARY OF THE INVENTION

This invention provides a recombinant super-compound interferon (rSIFN-co) and its equivalent with changed spatial configuration, high efficacy and low side effects. Therefore, high dose of rSIFN-co may be used.

This invention also provides artificial gene encoding for the super-compound interferon or its equivalent.

This invention provides a vector comprising the gene which codes for the super-compound interferon or its equivalent.

This invention provides an expression system comprising the vector comprising the gene which codes for the super-compound interferon or its equivalent. This invention also provides a host cell comprising the vector comprising the gene which codes for the recombinant super-compound interferon (rSIFN-co) or its equivalent. Said host cell may be eukaryotic or prokaryotic, such as $E.\ Coli.$ This invention provides a method for producing a recombinant super-compound interferon (rSIFN-co) with changed spatial configuration and enhanced antiviral activity comprising steps of:
(a) Introducing nucleic acid molecule which codes for said interferon with preferred codons for expression to an appropriate host; and
(b) Placing the introduced host in conditions allowing expression of said interferon.

This invention provides the method for producing recombinant super-compound interferon (rSIFN-co), further comprising recovery of the expressed interferon.

This invention provides a method for inhibiting, preventing or treating viral diseases, or for inhibiting or treating tumors in a subject comprising administering to the subject an effective amount of the super-compound interferon or its equivalent.

This invention provides the above-described method wherein super-compound interferon is administered orally, via vein injection, muscle injection, peritoneal injection, subcutaneous injection, nasal or mucosal administration, or by inhalation via a respirator.

This invention provides the method to prevent or treat viral diseases wherein the viral diseases is hepatitis A, hepatitis B, hepatitis C, other types of hepatitis, infections of viruses caused by Epstein-Barr virus, Human Immunodeficiency Virus (HIV), Ebola virus, Severe Acute Respiratory Syndrome Virus (SARS), Influenza virus, Cytomegalovirus, herpes simplex viruses, or other types of herpes viruses, papovaviruses, poxviruses, picornaviruses, adenoviruses, rhinoviruses, human T-cell leukemia viruses I, or human T-cell leukemia viruses II, or human T-cell leukemia virus III.

This invention provides the method to prevent or treat viral diseases wherein the viral diseases are Human Immunodeficiency Virus (HIV) and Ebola virus.

This invention provides a method for anti-hepatitis activities. It can inhibit HBV-DNA replication, HBsAg and HBeAg production.

This invention provides a method to prevent or treat upper respiratory infection diseases.

This invention provides a method to prevent or treat tumors or cancers wherein the tumor is skin cancer, basal cell carcinoma and malignant melanoma, renal cell carcinoma, liver cancer, thyroid cancer, rhinopharyngeal cancer, solid carcinoma, prostate cancer, stomach/abdominal cancer, esophageal cancer, rectal cancer, pancreatic cancer, breast cancer, ovarian cancer, and superficial bladder cancer, hemangioma, epidermoid carcinoma, cervical cancer, non-small-cell lung cancer, small-cell lung cancer, glioma, leucocythemia, acute leucocythemia and chronic leucocythemia, chronica myelocytic leukemia, hairy cell leukemia, lymphadenoma, multiple myeloma, polycythemia vera, or Kaposi's sarcoma.

This invention provides a method for preventing or treating virus-induced diseases in a subject comprising administering to the subject an effective amount of recombinant super-compound interferon or a functional equivalent thereof.

The super-compound interferon (rSIFN-co) may be administered orally, via vein injection, muscle injection, peritoneal injection, subcutaneous injection, nasal or mucosal administration, or by inhalation via a respirator.

This invention provides a method for inhibiting the causative agent of virus-induced diseases, comprising contacting the causative agent with an effective amount of super-compound interferon or its equivalent.

This invention also provides a method for inhibiting virus-induced diseases, comprising contacting an effective amount of the super-compound interferon with said virus or cells. This contact could be direct or indirect.

This invention provides a composition comprising an effective amount of the super-compound interferon capable of inhibiting, preventing or treating virus-induced diseases, and a suitable carrier.

This invention provides a pharmaceutical composition comprising an effective amount of the recombinant super-compound interferon capable of inhibiting, preventing or treating virus-induced diseases in a subject, and a pharmaceutically acceptable carrier.

This invention provides a method for preventing or treating tumors in a subject comprising administering to the subject an effective amount of recombinant super-compound interferon or a functional equivalent thereof.

This invention provides a method for inhibiting tumors, comprising contacting the causative agent with an effective amount of super-compound interferon or its equivalent.

This invention also provides a method for inhibiting tumors, comprising contacting an effective amount of the super-compound interferon with said virus or cells. This contact could be direct or indirect.

This invention provides a composition comprising an effective amount of the super-compound interferon capable of inhibiting, preventing or treating tumors, and a suitable carrier.

This invention provides a pharmaceutical composition comprising an effective amount of the recombinant super-compound interferon capable of inhibiting, preventing or treating tumors in a subject, and a pharmaceutically acceptable carrier.

DETAILED DESCRIPTION OF THE FIGURES

Figure 4:
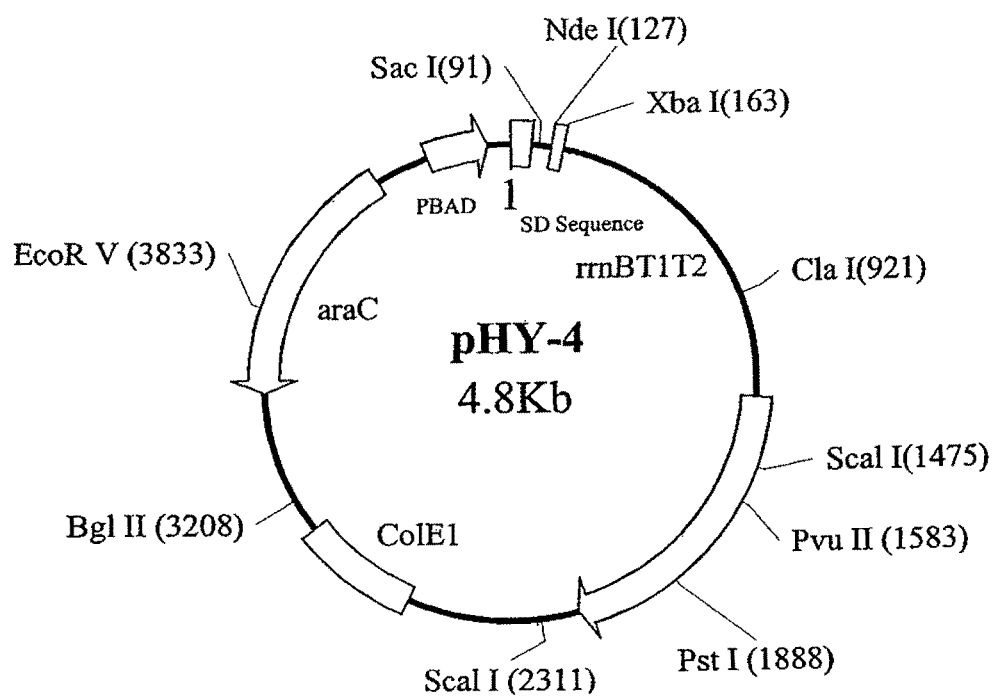
Figure 5:
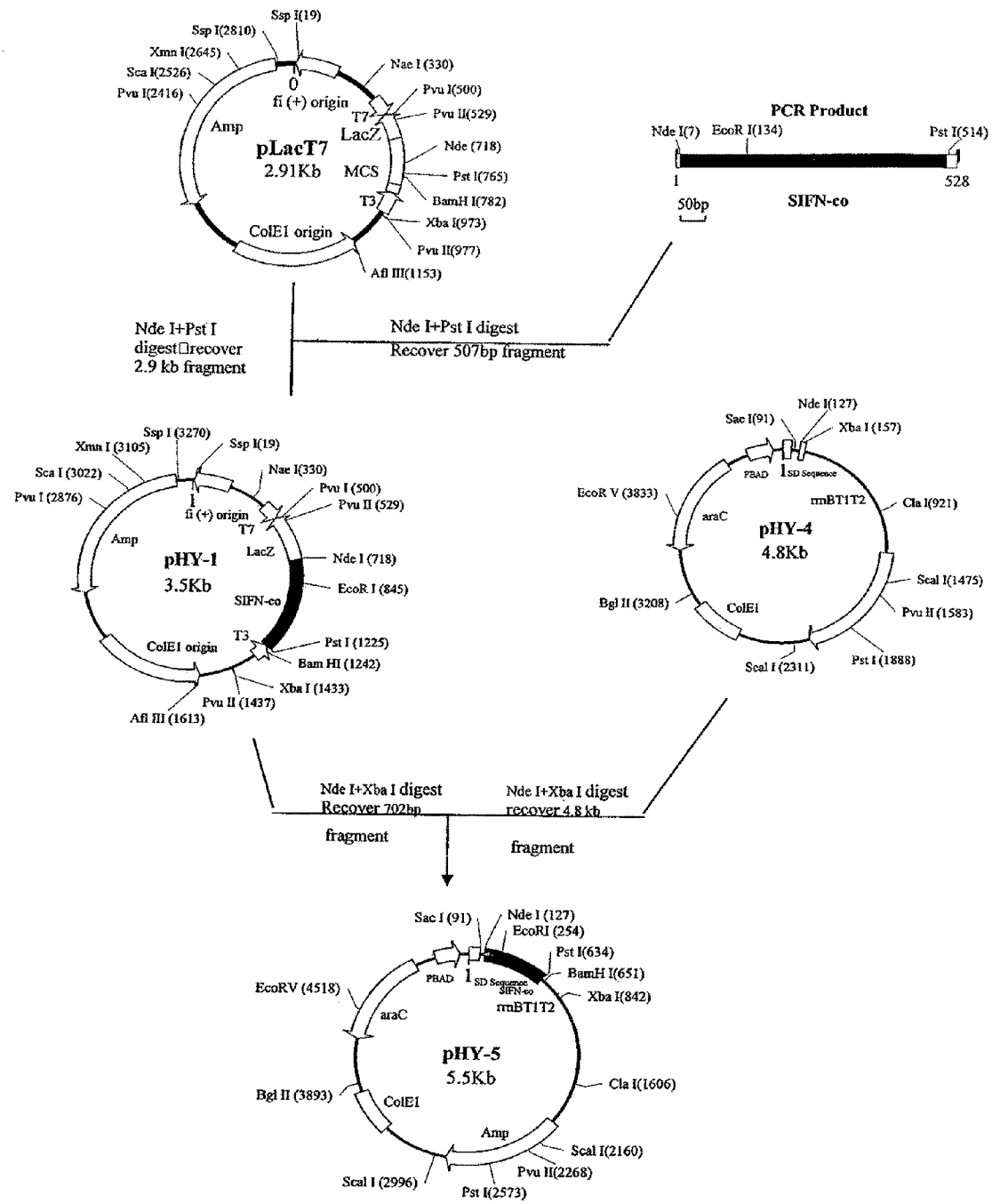

FIG. 1. rSIFN-co cDNA sequence designed according to *E. Coli.* codon usage and deduced rSIFN-co amino acid sequence FIGS. 2A-B. Sequence of another super-compound interferon FIG. 3. Diagram of pLac T7 cloning vector plasmid FIG. 4. Diagram of pHY-4 expression vector plasmid FIG. 5. Construction process of expression plasmid pHY-5

FIG. 6-A. Circular Dichroism spectrum of Infergen®

(Tested by Analysis and Measurement Center of Sichuan University)

Spectrum range: 250 nm-190 nm

Sensitivity: 2 m°/cm

Light path: 0.20 cm

Equipment: Circular Dichroism J-500C

Samples: contains 30 µg/ml IFN-con1, 5.9 mg/ml of NaCl and 3.8 mg/ml of $Na_2PO_4$, pH7.0.

Infergen® (interferon alfacon-1), made by Amgen Inc., also known as consensus interferon, is marketed for the treatment of adults with chronic hepatitis C virus (HCV) infections. It is currently the only FDA-approved, bio-optimized interferon developed through rational drug design and the only interferon with data on the label specifically for non-responding or refractory patients. InterMune's sales force re-launched Infergen® in January 2002 with an active campaign to educate U.S. hepatologists about the safe and appropriate use of Infergen®, which represents new hope for the more than 50 percent of HCV patients who fail other currently available therapies. See http://www.intermune.com/wt/itmn/infergen, Aug. 27, 2003

FIG. 6-B. Circular Dichroism spectrum of Infergen® From Reference [Journal of Interferon and Cytokine Research. 16:489-499 (1996)]

Circular dichroism spectra of concensus interferon subforms. Concensus interferon was fractionated using an anion exchange column. Samples were dialyzed into 10 mM sodium phosphate, pH 7.4. Measurements were made on Jasco J-170 spectopolarimeter, in a cell thermostat at 15° C. (———), acylated form; (- -) cis terminal form; ( · · · ), met terminal form. A. Far UV Spectrum. B. Near UV Spectrum.

FIG. 6-C. Circular Dichroism spectrum of rSIFN-co

Spectrum range: 320 nm-250 nm

Sensitivity: 2 m°/cm

Light path: 2 cm

Equipment: Circular Dichroism J-500C

Samples: contains 0.5 mg/ml rSIFN-co, 5.9 mg/ml of NaCl and 3.8 mg/ml of $Na_2PO_4$, pH7.0.

FIG. 6-D. Circular Dichroism spectrum of rSIFN-co

Spectrum range: 250 nm-190 nm

Sensitivity: 2 m°/cm

Light path: 0.20 cm

Equipment: Circular Dichroism J-500C

Samples: contains 30 µg/ml rSIFN-co, 5.9 mg/ml of NaCl and 3.8 mg/ml of $Na_2PO_4$, pH7.0.

Clearly, as evidenced by the above spectra, the secondary or even tertiary structure of rSIFN-co is different from Infergen®.

Figure 7:
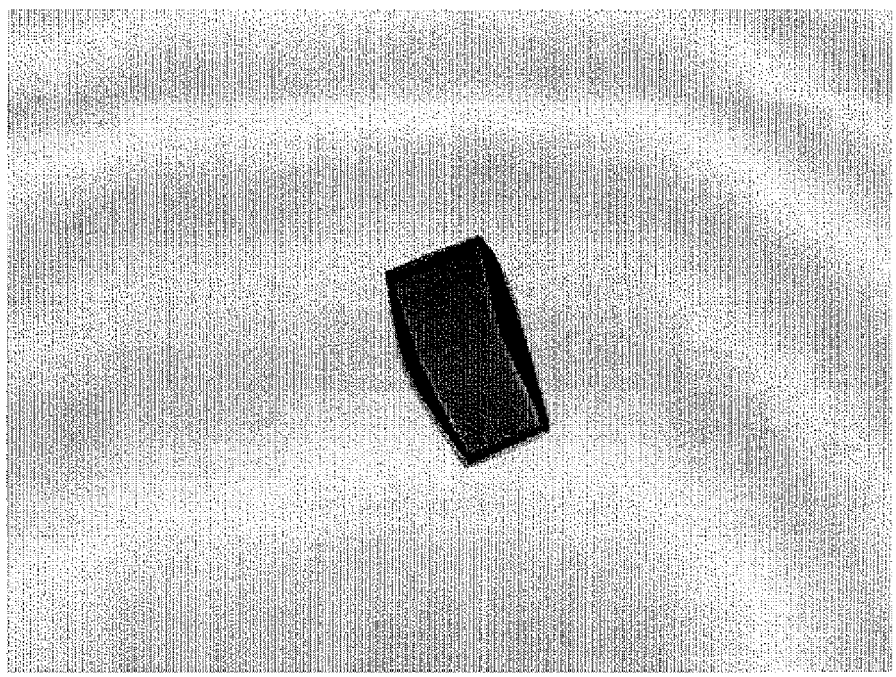

FIG. 7. rSIFN-co Crystal I

Figure 8:
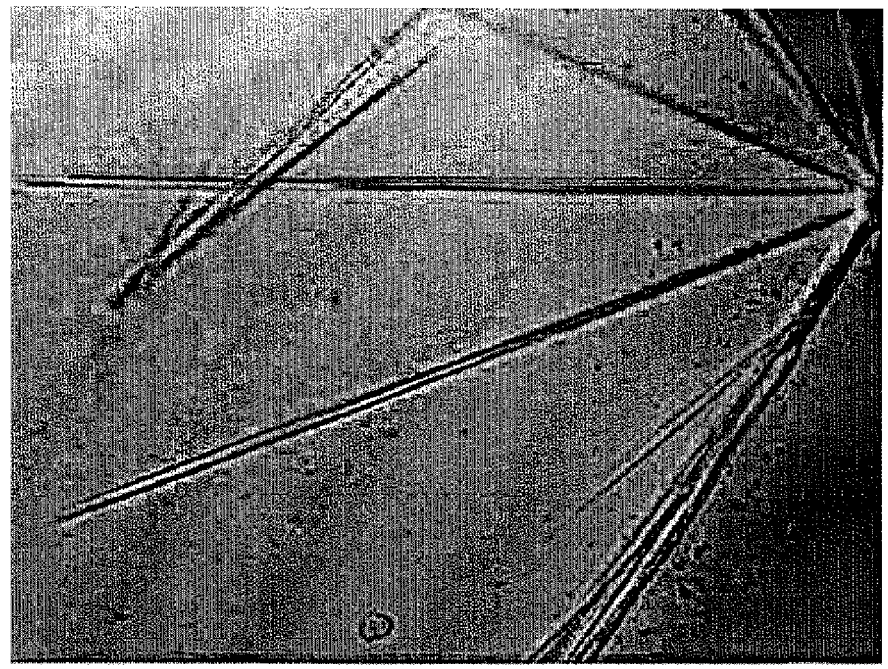

FIG. 8. rSIFN-co Crystal II

Figure 9:
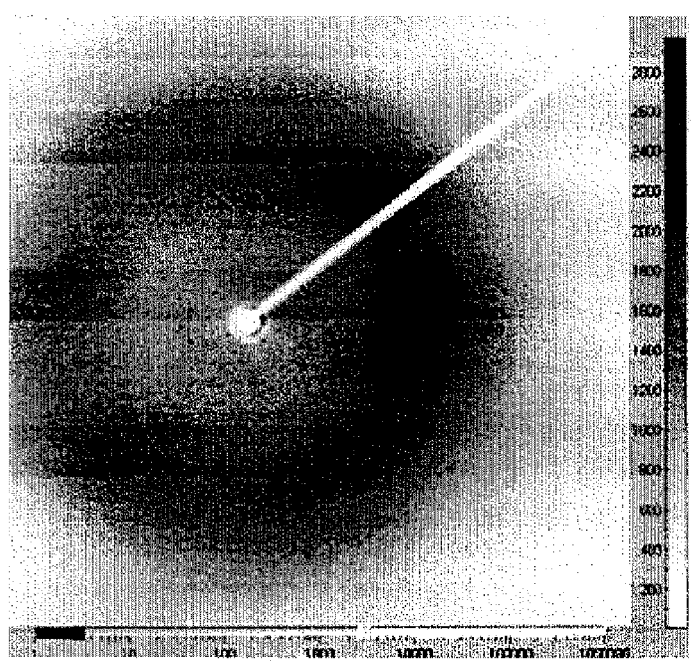

FIG. 9. The X-ray Diffraction of rSIFN-co Crystal

Figure 10:
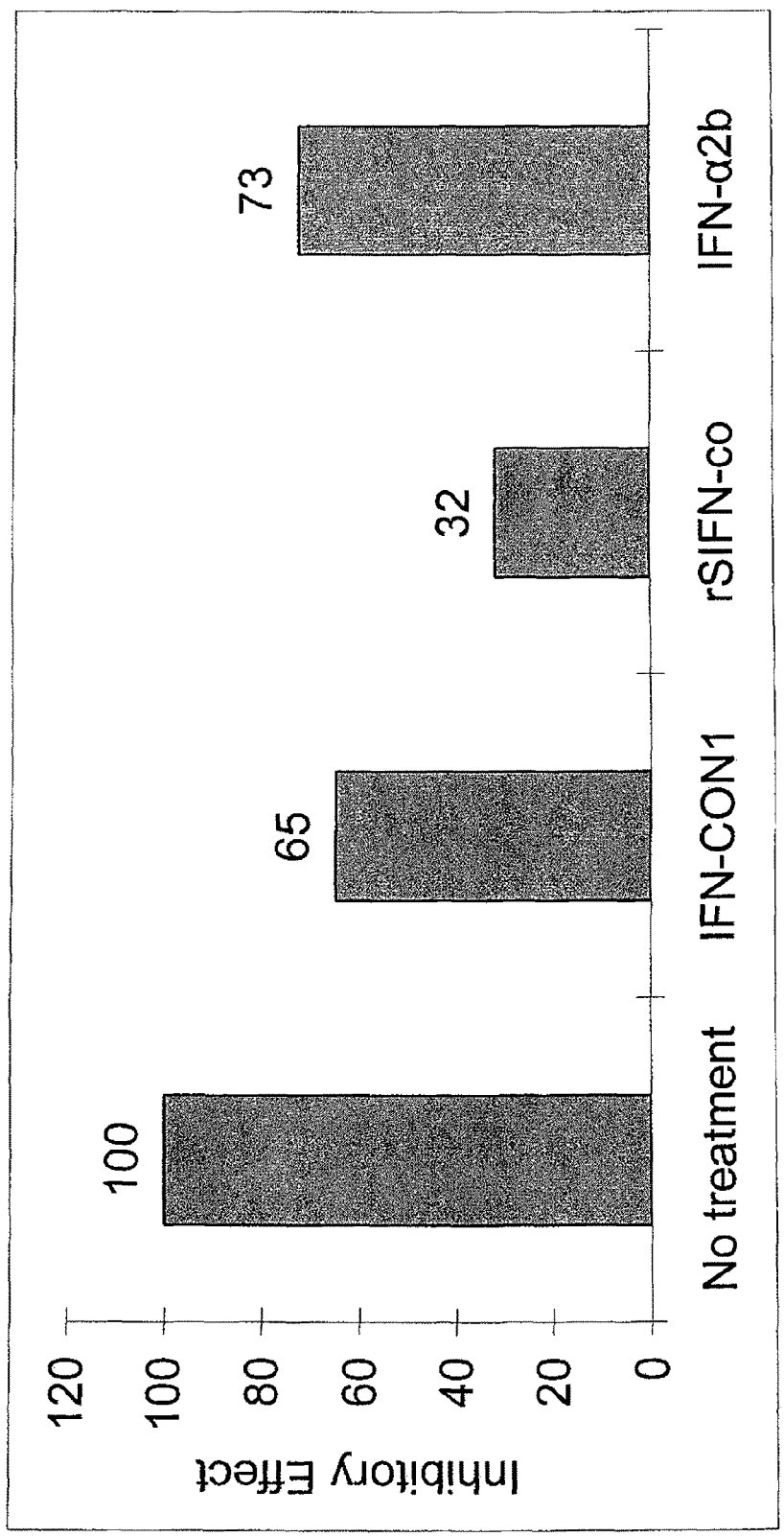
Figure 11B:
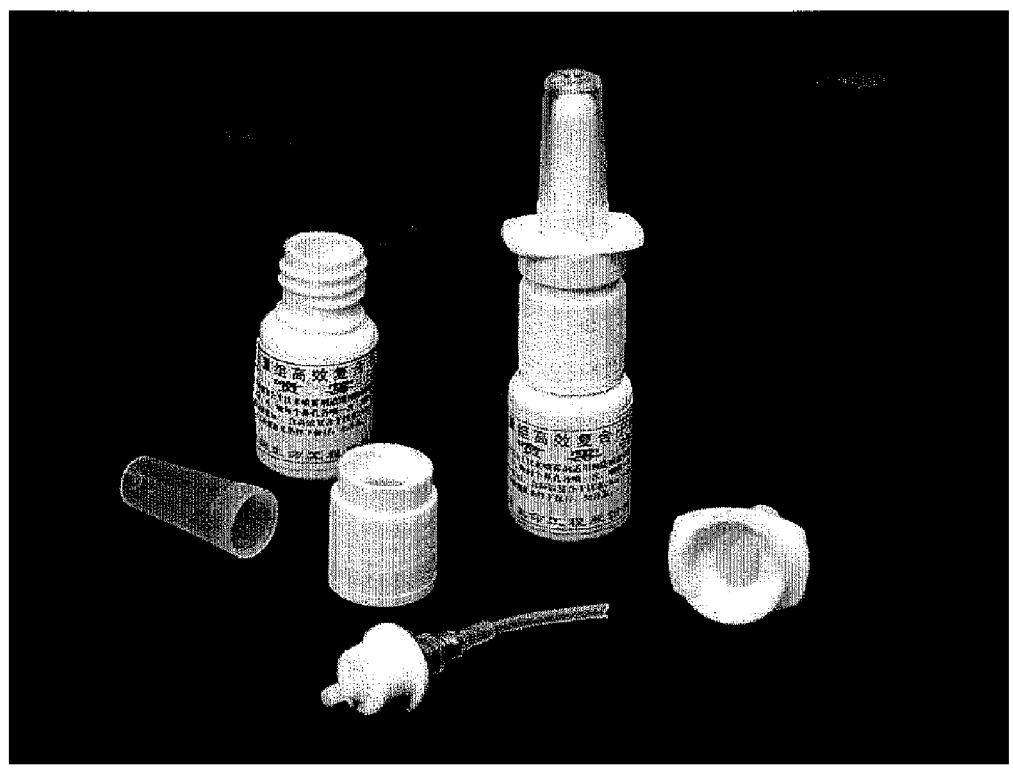
Figure 11C:
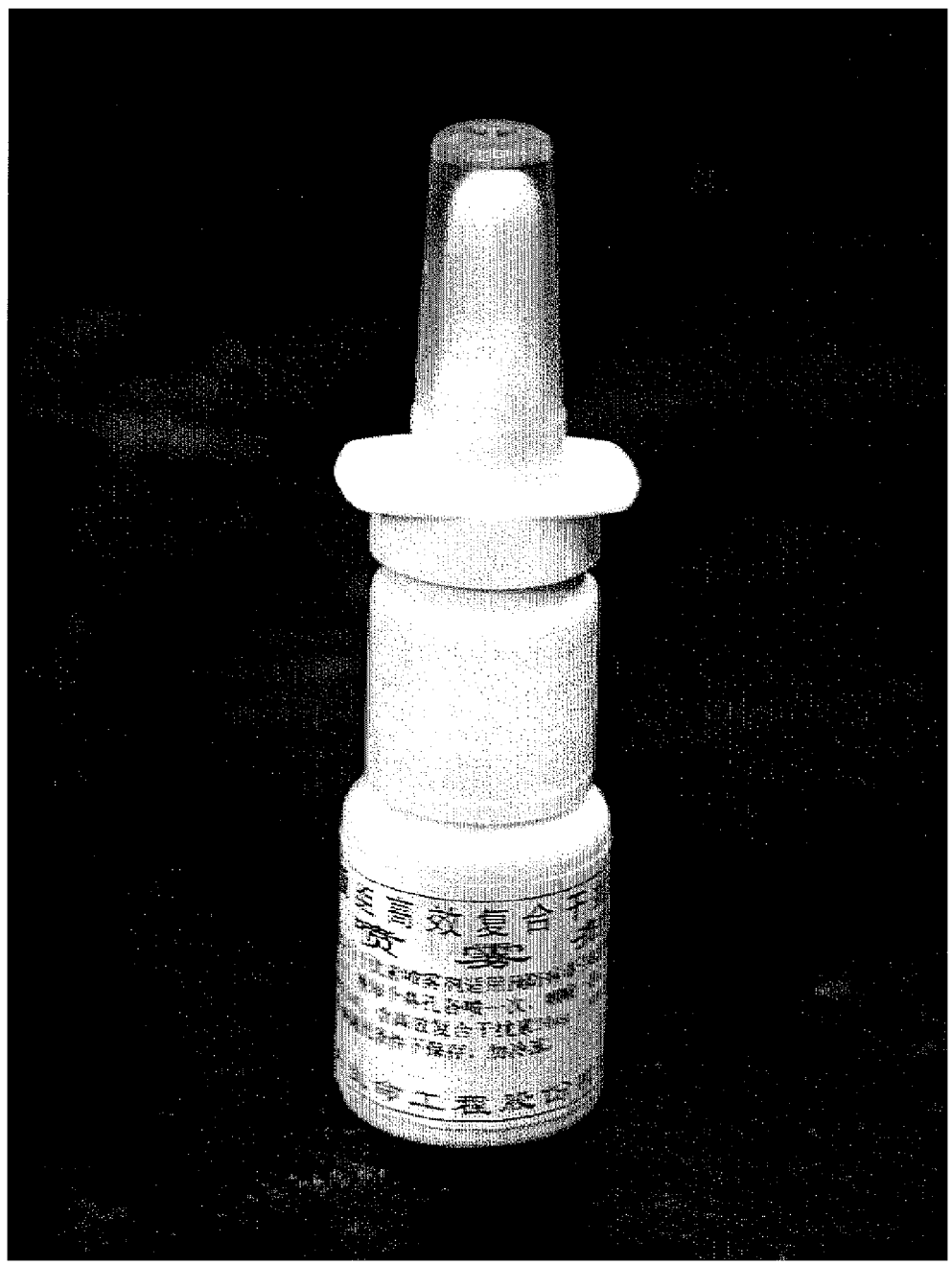

FIG. 10. Comparison of Inhibition Effects of Different Interferons on HBV Gene Expression FIG. 11A-C. Recombinant Super-Compound Interferon Spray
Height: 90 mm
Width: 25 mm (bottom), 6 mm (top)
Weight: 9 g
Volume delivery: 0.1 ml FIG. 11D. Recombinant Super-Compound Interferon Spray
When using the spray for the first time, take off the cap and discharge in the air several times until some liquid squirts out. Do not need to test spray for subsequent uses. To use, follow the illustrations shown in the figure, i.e.: (1) Pre-spray and (2) Press down on the nozzle to release the medication.

Figure 12:
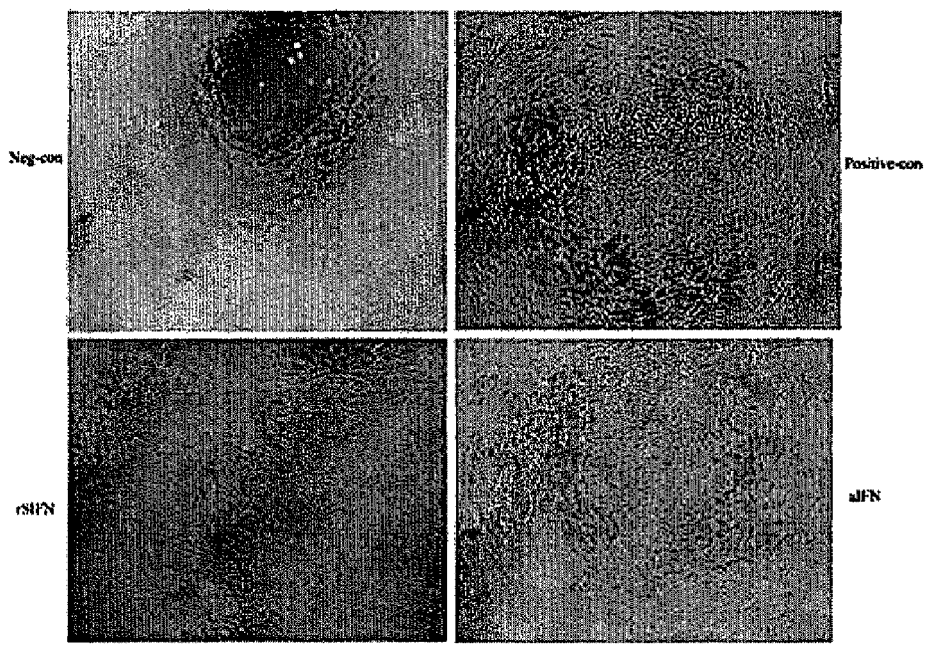

FIG. 12. Comparison of Anti-SARS Activity of Interferons: Left top panel is negative control i.e. no virus added. Right top panel is positive control i.e. virus is added, but no rSIFN-co added. Left bottom panel is rSIFN-co with SARS Virus. Right bottom panel is αIFN.

FIGS. 13A-1. Curves of Changes of Body Temperature in Group A (5 Patients)
This figure is the record of body temperature changes of 5 patients in Group A.

Figures 2, 13A:
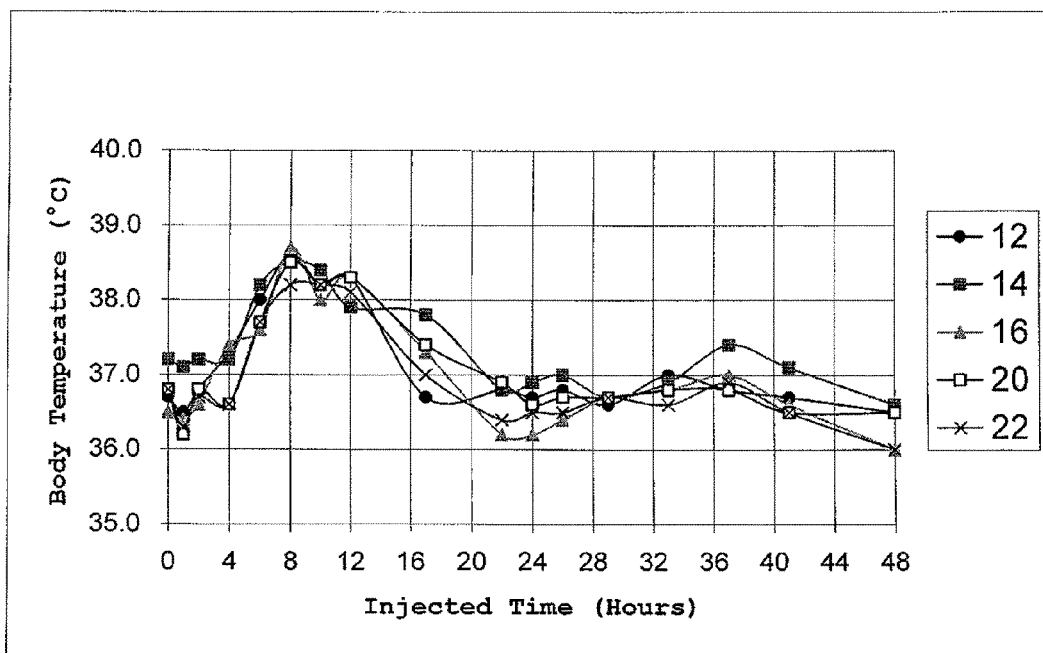

FIGS. 13A-2. Curves of Changes of Body Temperature in Group A (5 Patients)
This figure is the record of body temperature changes of the other 5 patients in Group A.

Figures 1, 13B:
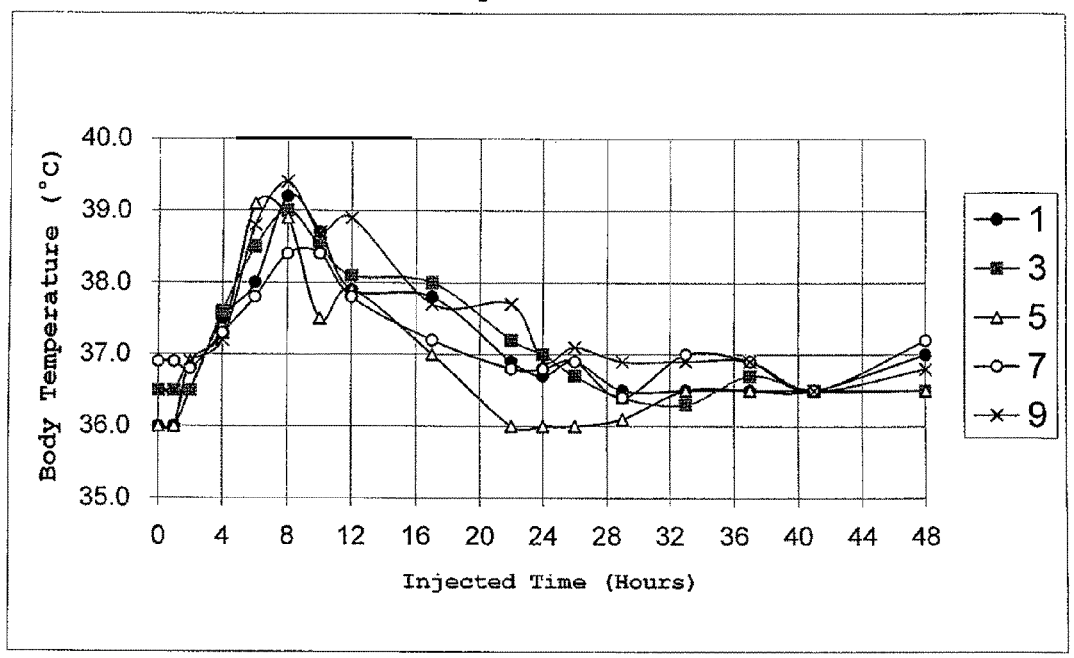
Figures 2, 13B:
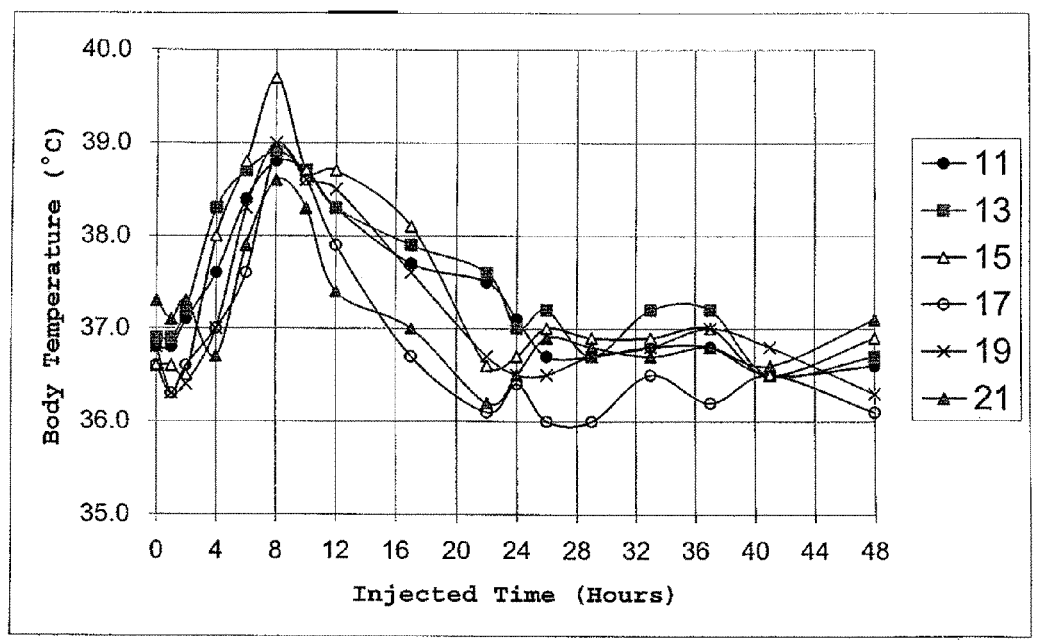

FIGS. 13B-1. Curves of Changes of Body Temperature in Group B (5 Patients)
This figure is the record of body temperature changes of 5 patients in Group B.

FIGS. 13B-2. Curves of Changes of Body Temperature in Group B (6 Patients)
This figure is the record of body temperature changes of the other 6 patients in Group B.

Figure 14:
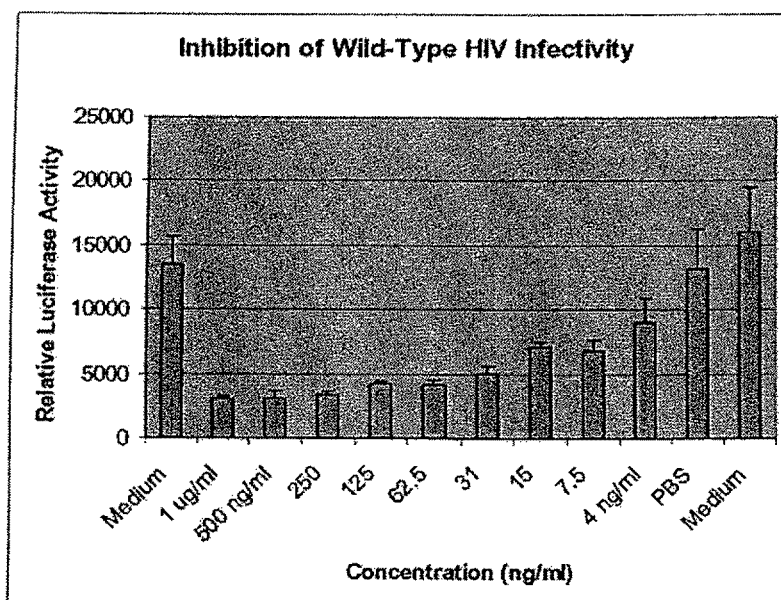

FIG. 14. Graph of Inhibition of Wild-Type HIV by rSIFN-co using EXCEL and Luciferase as Y axis and concentration of rSIFN-co as X axis. A clear inverse dose-dependent response has been shown.

Figure 15:
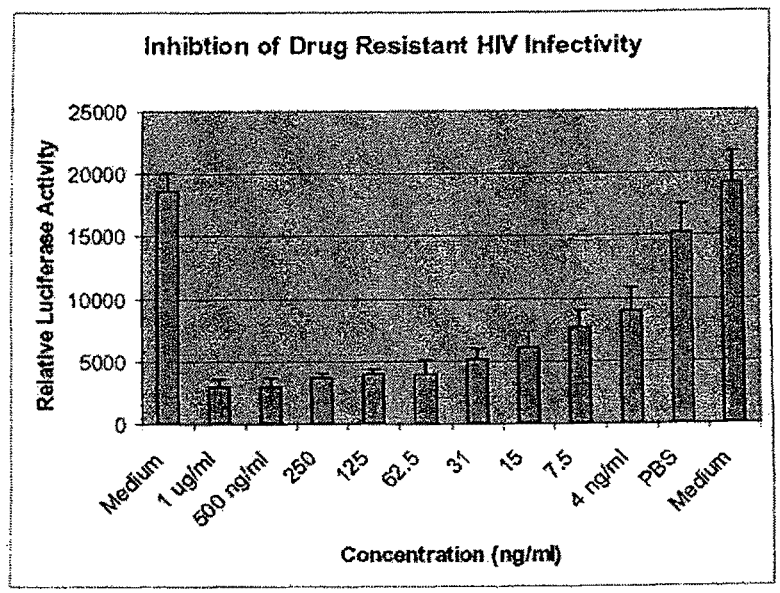

FIG. 15. Graph of Inhibition of Drug Resistant HIV by rSIFN-co using EXCEL and Luciferase as Y axis and concentration of rSIFN-co as X axis. A clear inverse dose-dependent response has been shown.

FIG. 16. rSIFN-co Inhibition of Influenza Virus: on the left, the control well is shown with Influenza virus added and without interferon, the cells had obvious CPE, such as rounding of cells, cell necroses, decrease in reflective light and sloughing off.

On the right, the experimental wells is shown containing Influenza virus and rSIFN-co at concentration 10 nanogram per milliliter (ng/ml) had morphology comparable to normal cells.

FIGS. 17A-H. Clinical Report of a patient with mammary and ovarian cancers. These figures show an obvious anti-cancer effect of rSIFN-co on this patient.

DETAILED DESCRIPTION OF THE INVENTION

Recombinant Super-Compound Interferon rSIFN-co

This invention provides a recombinant super-compound interferon (rSIFN-co) or an equivalent thereof with changed spatial configuration. This invention reveals that proteins with the same primary sequence might have different biological activities. As illustrated in this application, proteins with identical amino acid sequences may have different activities. The efficacy of these proteins may sometimes be improved and, sometimes, proteins with changed spatial configuration would reveal new function.

As defined herein, equivalents are molecules which are similar in function to the compound interferon. An equivalent could be a deletion, substitution, or replacement mutant of the original sequence. Alternatively, it is also the intention of this invention to cover mimics of the recombinant super-compound interferon (rSIFN-co). Mimics could be a peptide, polypeptide or a small chemical entity.

The recombinant super-compound interferon (rSIFN-co) described herein includes but is not limited to interferon α, β, γ or ω. In an embodiment, it is IFN-1α, IFN-2β or other mutants.

In another embodiment, the recombinant super-compound interferon (rSIFN-co) disclosed has higher efficacy than α, β, γ, ω or a combination thereof and as compared to the interferons disclosed in U.S. Pat. Nos. 4,695,623 and 4,897,471. This recombinant super-compound interferon (rSIFN-co) is believed to have unique secondary or tertiary structure, wherein the 3-dimensional change is the result of changes in its production process. (See e.g. FIG. 6).

The recombinant super-compound interferon (rSIFN-co) described herein has spatial structure change(s) resulting from the changes of its production process.

Lower Side Effects

The recombinant super-compound interferon (rSIFN-co) possesses lower side effects when compared with other interferons. These lower side effects allow for higher dosages to be used on patients in need of interferon treatments. These lower side effects open the possibility of using rSIFN-co for prevention and/or treatment of other diseases. Accordingly, this invention provides the recombinant super-compound interferon (rSIFN-co) with less side effects when administered to a subject.

This invention provides recombinant super-compound interferon (rSIFN-co) with less side effects as compared to all currently available interferons.

This invention further provides a method for treating or preventing viral diseases or tumors in a subject comprising administering to the subject an effective amount of the rSIFN-co with less side effects as compared to all currently available interferons. Therefore, high dose of rSIFN-co may be used. In an embodiment, the effective amount of recombinant super-compound interferon is in nanogram level.

Process to Produce rSIFN-co

Artificial Gene

This invention also provides artificial gene encoding for the super-compound interferon or its equivalent. It is within the ordinary skill to design an artificial gene. Many methods for generating nucleotide sequence and other molecular biology techniques have been described previously. See for example, Joseph Sambrook and David W. Russell, Molecular Cloning: A laboratory Manual, December 2000, published by Cold Spring Harbor Laboratory Press.

The recombinant super-compound interferon (rSIFN-co) may also be produced with its gene as artificially synthesized cDNA with adjustment of its sequence from the wild-type according to codon preference of E. Coli. Extensive discussion of said codon usage (preference) may be found in U.S. Pat. No. 4,695,623. See e.g. column 6, line 41-column 7, line 35.

Vector

This invention provides a vector comprising the gene which codes for the super-compound interferon or its equivalent.

This invention provides an expression system comprising the vector comprising the gene which codes for the super-compound interferon or its equivalent. The cells include, but are not limited to, prokaryotic or eukaryotic cells.

This invention also provides a host cell comprising the vector comprising the gene which codes for the recombinant super-compound interferon (rSIFN-co) or its equivalent.

This invention provides a method for producing a recombinant super-compound interferon (rSIFN-co) with changed spatial configuration and enhanced antiviral activity comprising steps of:
(a) Introducing nucleic acid molecule which codes for said interferon with preferred codons for expression to an appropriate host; and
(c) Placing the introduced host in conditions allowing expression of said interferon.

This invention provides the method for producing recombinant super-compound interferon (rSIFN-co), further comprising recovery of the expressed interferon.

Expression System

The above-described recombinant super-compound interferon (rSIFN-co) may be produced by a high-efficiency expression system which uses a special promoter, enhancer or other regulatory element. In an embodiment the promoter is inducible. Said inducible promoter includes but is not limited to $P_{BAD}$, heat shock promoters or heavy metal inducible promoters. Heat shock promoters are activated by physical means, while other promoters are activated by chemical means, for example IPTG or Tetracyclin. IPTG is added to the cells to activate the downstream gene or removed to inactivate the gene. Tetracyclin is used to induce promoters or to regulate the strength of promoters. See http://www.bio.davidson.edu/courses/genomics/method/plasmid inducible.html.

In an embodiment the promoter is $P_{BAD}$. Since early nineties, the properties of the mechanism of expression and repression of $P_{BAD}$ by AraC have been studied extensively, and their interactions have been dissected at the molecular level. See Schleif, R. S. 1992 DNA looping. *Annu. Rev. Biochem.* 61:199-223. The AraC protein is both a positive and negative regulator, when present, it turns on the transcription from the $P_{BAD}$ promoter, when absent, the transcription occurs at a very low rate. See Guzman, L. M. et al. (1995) *J. Bact.* 177: 4121-4130. The efficacy and mechanism of $P_{BAD}$ promoter is well known by other ordinary skilled artisans and is commercially-available. See http://www.invitrogen.com/content/sfs/brochures/710 01619 pBAD bro.pdf The commercially-available Invitrogen expression kit includes pBAD vectors' designed to provide precise control of expression levels. The araBAD promoter initiates gene expression. It's both positively and negatively regulated by the product of the araC gene, a transcriptional regulator that forms a complex with L-arabinose. In the absence of arabinose, the AraC dimer contacts the O2 and I1 half sites of the araBAD operon, forming a 210 bp DNA loop. For maximum transcriptional activation, two events are required: first, Arabinose binds to AraC. The protein releases the O2 site and binds the I2 site, which is adjacent to the I1 site. This releases the DNA loop and allows transcription to begin. Second, the cAMP activator protein (CAP)-cAMP complex binds to the DNA and stimulates binding of AraC to I1 and I2. Basal expression levels can be repressed by introducing glucose to the growth medium. Glucose acts by lowering cAMP levels, which in turn decreases the binding of CAP. As cAMP levels are lowered, transcriptional activation is decreased. Invitrogen's pBAD vectors are specifically designed for maximum expression and ease of use.

Nine pBAD vectors are currently available: pBAD102/D-TOPO®, pBAD202/D-TOPO®, pBAD-TOPO®, pBAD/Thio-TOPO®, pBAD/His, pBAD/Myc-His, pBAD-DEST49, pBAD/gIII and pBAD/Thio-E. with the following features in all pBAD vectors:
1. araBAD promoter for dose-dependent regulation
2. araC gene for tight control of the araBAD promoter
3. Optimized ribosome binding site for increased translation efficiency
4. rrnB transcription termination region for efficient transcript The inducible promoters include but are not limited to heat shock promoters or heavy metal inducible promoters.

This invention provides a process for production of recombinant super-compound interferon (rSIFN-co) comprising introducing an artificial gene with selected codon preference into an appropriate host, culturing said introduced host in an appropriate condition for the expression of said compound interferon and harvesting the expressed compound interferon.

The process may comprise extraction of super recombinant super-compound interferon (rSIFN-co) from fermentation broth, collection of inclusion bodies, denaturation and renaturation of the harvested protein.

The process may maintain the high efficacy even when the recombinant super-compound interferon (rSIFN-co) is used with an agent and in a particular concentration. The process also comprises separation and purification of the recombinant super-compound interferon (rSIFN-co). The process further comprises lyophilization of the purified recombinant super-compound interferon (rSIFN-co). The process comprises production of liquid injection of recombinant super-compound interferon (rSIFN-co).

In one embodiment, recombinant super-compound interferon (rSIFN-co) was produced with recombinant techniques. On the condition of fixed amino acid sequence, the IFN DNA was redesigned according to the *E. Coli.* codon usage and then the rSIFN-co gene was artificially synthesized. rSIFN-co cDNA was cloned into the high-expression vector of *E. Coli.* by DNA recombinant techniques, and a high expression of rSIFN-co was gained by using of induce/activate-mechanism of L-arabinose to activate the transcription of $P_{BAD}$ promoter.

Compared with usual thermo-induction, pH induction and IPTG induction systems of genetic engineering, arabinose induction/activation system has some advantages: (1) Common systems relieve promoter function by creating a "derepression" pattern. Promoters then induce downstream gene expression. Temperature and pH change and the addition of IPTG cannot activate promoters directly. In the system disclosed herein, L-arabinose not only deactivates and represses but also activates the transcription of $P_{BAD}$ promoter which induces a high expression of rSIFN-co. Therefore, the arabinose induction/activation system is a more effective expression system. (2) The relationship between Exogenous and L-arabinose dosage is linear. This means the concentration of arabinose can be changed to adjust the expression level of the exogenous gene. Therefore, it is easier to control the exogenous gene expression level in *E. Coli.* by arabinose than by changing temperature and pH value. This characteristic is significant for the formation of inclusion bodies. (3) L-arabinose is resourceful, cheap and safe, which, on the contrary, are the disadvantages of other inducers such as IPTG.

This embodiment creates an effective and resistant rSIFN-co-expressing *E. Coli.* engineering strain with an L-arabinose induction/activation system. The strain is cultivated and fermented under suitable conditions to harvest the bacterial bodies. Inclusion bodies are then purified after destroying bacteria and washing repeatedly. The end result, mass of high-purity, spatial-configuration-changed rSIFN-co protein for this invention and for clinical treatment, was gained from denaturation and renaturation of inclusion bodies and a series of purification steps. Said purification would not affect the biological activity of the purified protein.

The above-described recombinant super-compound interferon (rSIFN-co) possesses anti-viral or anti-tumor activity, and; therefore, is useful in inhibiting, preventing and treating viral diseases, inhibiting or treating tumors, or cancers.

Viral Diseases

This invention provides a method for treating or preventing viral diseases or tumors in a subject comprising administering to the subject an effective amount of the recombinant super-compound interferon (rSIFN-co) or its equivalent.

As used herein, viral diseases include, but are not limited to, hepatitis A, hepatitis B, hepatitis C, other types of hepatitis, infections caused by Epstein-Barr virus, Human Immunodeficiency Virus (HIV), Ebola virus, Severe Acute Respiratory Syndrome Virus (SARS), Influenza virus, Cytomegalovirus, herpes simplex viruses, other herpes viruses, papovaviruses, poxviruses, picornaviruses, adenoviruses, rhinoviruses, human T-cell leukemia virus I, human T-cell leukemia virus II, or human T-cell leukemia virus III.

In an embodiment, the effective amount is at nanogram level. In another embodiment, the virus is Human Immunodeficiency Virus and the effective amount is as low as 4 nanograms per milliliter. In another embodiment, the virus is Influenza and the effective amount is as low as 10 nanogram per milliliter.

Inhibition of DNA Replication and Secretion of HBsAg and HBeAg of Hepatitis B Virus.

The recombinant super-compound interferon (rSIFN-co) inhibits the DNA duplication and secretion of HBsAg and HBeAg of Hepatitis B Virus.

Severe Acute Respiratory Syndrome Virus (SARS)

This invention provides a method for preventing or treating Severe Acute Respiratory Syndrome, or virus-induced upper respiratory diseases, of a subject comprising administering to the subject an effective amount of recombinant super-compound interferon (rSIFN-co) or a functional equivalent thereof. In an embodiment of the above method, the interferon is α, β, γ, ω or a combination thereof.

The recombinant super-compound interferon (rSIFN-co) may be administered orally, via vein injection, muscle injection, peritoneal injection, subcutaneous injection, nasal or mucosal administration, or by inhalation via a spray or a respirator. In an embodiment rSIFN-co is administered subcutaneously or intramuscularly at a dose of higher than or equal to 10 Million International Unit per square meter of surface area. In another embodiment rSIFN-co is administered subcutaneously or intramuscularly at a dose of higher than or equal to 20 Million International Unit per square meter of surface area. In an embodiment, the interferon is delivered by a spray device. In a specific embodiment, the device is described in FIG. 11. In one of the embodiments, the interferon is lyophilized.

This invention provides a method for inhibiting the causative agent of Severe Acute Respiratory Syndrome, or virus-induced upper respiratory diseases, comprising contacting the agent with an effective amount of recombinant super-compound interferon (rSIFN-co) or its equivalent.

It is determined that the causative agent of SARS is a virus. See eg. Rota et al (2003), Characterization of a Novel Coronavirus Associated with Severe Acute Respiratory Syndrome. Science 1085952 www.sciencexpress.org and Marra, et al. (2003), The Genome Sequence of the SARS-Associated Coronavirus. Science 1085853 www.sciencexpress.org.

This invention also provides a method for inhibiting Severe Acute Respiratory Syndrome virus or Severe Acute Respiratory Syndrome virus-infected cells, or virus-induced upper respiratory diseases, or cells infected with viruses capable of inducing upper respiratory diseases, comprising contacting an effective amount of the recombinant super-compound interferon (rSIFN-co) with said virus or cell. This contact could be direct or indirect.

This invention provides a composition comprising an effective amount of the recombinant super-compound interferon (rSIFN-co) capable of inhibiting Severe Acute Respiratory Syndrome virus or Severe Acute Respiratory Syndrome virus-infected cells, or virus-induced upper respiratory diseases, or cells infected with viruses capable of inducing upper respiratory diseases, and a suitable carrier.

This invention provides a composition comprising an effective amount of the super-compound interferon capable of preventing or treating Severe Acute Respiratory Syndrome, or virus-induced upper respiratory diseases, of a subject and a suitable carrier.

This invention provides a pharmaceutical composition comprising an effective amount of the recombinant super-compound interferon (rSIFN-co) capable of inhibiting Severe Acute Respiratory Syndrome virus or Severe Acute Respiratory Syndrome virus-infected cells, or virus-induced upper respiratory diseases, and a pharmaceutically acceptable carrier.

This invention provides a pharmaceutical composition comprising an effective amount of the recombinant super-compound interferon (rSIFN-co) capable of preventing or treating Severe Acute Respiratory Syndrome, or virus-induced upper respiratory diseases, in a subject and a pharmaceutically acceptable carrier.

This invention provides a device to deliver the above-described pharmaceutical composition.

In a preferred embodiment, the subject is a human. As it can easily be appreciated, the super-compound interferon can be used in other animals or mammals.

This invention provides a method for preventing Severe Acute Respiratory Syndrome or virus-induced upper respiratory diseases, in humans comprising application of the super-compound interferon three times a day via a spray which contains twenty micrograms of interferon, equal to ten million units of activity in three milliliter.

Viral Upper Respiratory Infection (VURI)

Viral upper respiratory infection, alternative names common cold, colds. This is a contagious viral infection of the upper respiratory tract characterized by inflammation of the mucous membranes, sneezing, and a sore throat. It is usually caused by over 200 different viruses, known as rhinoviruses. Colds are not caused by the same viruses responsible for Influenza. Colds are spread through droplets from the coughing or sneezing of others with a cold or by hand contact with objects contaminated by someone with a cold. The incidence of colds is highest among children, and the incidence decreases with age because immunity to the virus causing the cold occurs after the illness. Gradually, immunity to a wide variety of viruses that cause colds is developed in adults. Children may have 10 colds a year, and adults may have 3 colds a year.

The U.S. Centers for Disease Control and Prevention have estimated that the average annual incidence of upper respiratory tract infections (URIs) in the United States is 429 million episodes, resulting in more than $2.5 billion in direct and indirect healthcare costs. The common cold is most often caused by one of several hundred rhinoviruses (52%), but coronaviruses (8%) or the respiratory syncytial virus (7%) may also lead to infection. Other viruses, such as influenza (6%), parainfluenza, and adenoviruses, may produce respiratory symptoms, but these are often associated with pneumonia, fever, or chills.

Colds occur in a seasonal pattern that usually begins in mid-September and concludes in late April to early May. The common cold is quite contagious and can be transmitted by either person-to-person contact or airborne droplets. Upper respiratory symptoms usually begin 1 to 2 days after exposure and generally last 1 to 2 weeks, even though viral shedding and contagion can continue for 2 to 3 more weeks. Symptoms may persist with the occurrence of complications such as sinusitis or lower respiratory involvement such as bronchitis or pneumonia.

The common cold has a variety of overt symptoms, including malaise, nasal stuffiness, rhinorrhea, nonproductive cough, mild sore throat, and, in some cases, a low-grade fever. Because of the similarity of symptoms, a cold may be mistaken for perennial allergic rhinitis, but allergies can usually be ruled out because of the differences in chronicity.

If a patient presents with a viral URI, the spectrum of remedies is extensive. Since most of these infections are self-limiting, clinicians usually recommend rest and fluids, but other treatments include environmental and nutritional therapies, over-the-counter and prescription decongestant and antihistamine products, new antihistamine and anticholinergic nasal formulations, and antibiotics. Table 1 lists commonly used cough and cold medications and their side effects.

TABLE 1

A Profile of Common Cough and Cold Medications and Their Side Effects

| Medication | Purpose | Side Effects and Special Considerations |
|---|---|---|
| Aerosolized beta2 agonists (eg, albuterol) | Reverse postinflammatory bronchospasm | Raises heart rate and may cause tremor |
| Alcohol-based liquid combination products | Treat multiple symptoms | Potential drowsiness and coordination problems |
| Alpha1 agonists (oral) (eg, pseudoephedrine, phenylpropanolamine) | Decongestion | May cause tachycardia, nervousness, transient stimulation, dizziness, drowsiness, elevation of blood pressure |
| Anticholinergic compounds: Ipratropium bromide (topical) | Drying | May cause nasal dryness and occasional epistaxis |
| Other anticholinergics (eg, methscopolamine, atropine, hyoscyamine) | Drying | May cause orthostasis, dysfunction of heat regulation, dry mouth, constipation |
| Antihistamines (oral) (eg, chlorpheniramine, diphenhydramine) | Drying | Drowsiness, dry mouth, orthostatic hypertension |
| Benzonatate capsules | Cough suppression, local anesthesia | Chewing can numb the mouth; can cause sedation, dizziness |
| Codeine, hydrocodone | Cough suppression | Drowsiness, constipation, nausea |
| Dextromethorphan | Cough suppression | Drowsiness possible, but side effects uncommon |
| Guaifenesin | Promote expectoration (mucolysis) | No side effects; must be taken with lots of water to improve efficacy |
| Topical decongestants (eg, oxymetazoline, phenylephrine) | Decongestion | Local burning; prolonged use may cause dependence |
| Zinc and vitamin C lozenges | Possible reduction in symptom severity and duration | Possible taste disturbance, increase of oxalate stones if susceptible |

Abstract from http://www.physsportsmed.com/issues/1998/02feb/swain.htm
Prevention and Treatment of Upper Respiratory Tract Infections (URI)

Nearly 70~80% URI are caused by viruses such as respiratory Syncytical virus, adenovirus, rhinovirous, cox-sackie virus, corona virus and its variant, influenza A virus and its variant, influenza B virus and its variant, parainfluenza virus and its variant, or enterovirus and its variant. A main cause of URI in adults is from rhinovirous. For children, respiratory syncytical virus and parainfluenza virus are two leading causes of URI.

Recombinant super-compound interferon (rSIFN-co) plays an important role in the fight against virus that causes URI. Super-compound interferon gains its anti-virus effects mainly via two mechanisms:
1. Attach to surface of sensitive cells and induce them to produce anti-virus protein, then block the duplication and reproduction of viruses in vivo.
2. recombinant super-compound interferon (rSIFN-co) can adjust immune response, including T-cell immune response, activity of NK cell, the phagocytosis function of monokaryon, and even formation of some antibodies in vivo.

In treatment for URI, recombinant super-compound interferon (rSIFN-co) can be directly applied to the affected area via a spray or a respiration. This method of treatment allows the interferon to reach the target cells first hand. Consequently, marketing the supply as a spray, rather than via oral or injection, would be safer and more effective for administrating the interferon.
Prevention and Treatment of SARS With the consent of the Sichuan (a province in China) working group on SARS prevention and control, the distribution of recombinant super-compound interferon (rSIFN-co) began in May of 2003. Super-compound interferon spray was allocated to doctors and nurses in hospitals, populated areas with a high risk for SARS, and to the National research group on prevention and control of SARS. Among the 3,000 users as of Dec. 19, 2003, there were no reports of any side effects connected to the use of the spray. Furthermore, none of the doctors and nurses, the people of Sichuan Province, or other organizations that have used the Super-compound interferon spray has been infected by SARS.

Therefore, this invention provides a method for inhibiting, preventing or treating virus replication or virus-infected cells by contacting said virus or infected cells with an effective amount of the recombinant super-compound interferon (rSIFN-co) or its equivalent.
Prevention and Treatment of Tumors This recombinant super-compound interferon (rSIFN-co) is useful in inhibiting, preventing or treating the following cancers or tumors:

| Cancer | Skin Cancer | Basal Cell Carcinoma |
| --- | --- | --- |
| | | Malignant Melanoma |
| | Renal cell carcinoma | |
| | Liver Cancer | |
| | Thyroid Cancer | |
| | Rhinopharyngeal Cancer | |
| | Solid Carcinoma | Prostate Cancer |
| | | Stomach/Abdominal Cancer |
| | | Esophageal Cancer |
| | | Rectal Cancer |
| | | Pancreatic Cancer |
| | | Breast Cancer |
| | Ovarian Cancer & | |
| | Superficial Bladder | |
| | Cancer | |
| | Hemangioma | |
| | Epidermoid Carcinoma | Cervical Cancer |
| | | Non-small Cell Lung Cancer |
| | | Small Cell Lung Cancer |
| | | Glioma |
| Malignant | Leucocythemia | Acute Leucocythemia |
| Hemal | | Chronic Leucocythemia |
| Disease | Chronic Myelocytic Leukemia | |
| | Hairy Cell Leukemia | |
| | Lymphadenoma | |
| | Multiple Myeloma | |
| | Polycythemia Vera | |
| Others | Kaposi's Sarcoma | |

Accordingly, this invention provides a method for inhibiting tumor or cancer cell growth by contacting the recombinant super-compound interferon (rSIFN-co) or its equivalent with said tumor or cancer cells.

Formulation and Route of Administration

This invention also provides the produced super-compound interferon by the above processes.

This invention provides a composition comprising recombinant super-compound interferon (rSIFN-co) or its equivalent and a suitable carrier.

This invention provides a pharmaceutical composition comprising the recombinant super-compound interferon (rSIFN-co) or its equivalent and a pharmaceutically acceptable carrier.

This invention provides the above-described method wherein recombinant super-compound interferon (rSIFN-co) is administered via orally via vein injection, muscle injection, peritoneal injection, subcutaneous injection, nasal or mucosal administration, or by inhalation via a spray or a respirator.

This invention provides the above-described method wherein recombinant super-compound interferon (rSIFN-co) is administered following the protocol of injections of 9 μg, 15 μg or 24 μg every two days, 3 times a week, for 24 weeks.

It was surprising to find that recombinant super-compound interferon (rSIFN-co), the spatial structure of which has been changed, is not only a preparation to inhibit the DNA duplication of hepatitis B, but to inhibit the secretion of HBsAg and HBeAg on 2.2.15 cells.

One objective of this invention is to offer a preparation of recombinant super-compound interferon (rSIFN-co) to directly inhibit the DNA duplication of hepatitis B viruses and the secretion of HBeAg and HBsAg of hepatitis B and decrease them to normal levels.

Formulation

The following are some rSIFN-co preparations: tablets, capsules, liquids for oral consumption, pastes, injections, sprays, suppositories, and solutions. Injections are recommended. It is common to subcutaneously inject or vein-inject the medicine. The medicine carrier could be any acceptable medicine carrier, including carbohydrates, cellulosum, adhesive, collapse, emollient, filling, add-dissolving agent, amortization, preservative, thickening agent, matching, etc.

This invention also provides a pharmaceutical composition comprising the above composition and a pharmaceutically acceptable carrier.

For the purposes of this invention, "pharmaceutically acceptable carriers" means any of the standard pharmaceutical carriers. Examples of suitable carriers are well known in the art and may include, but are not limited to, any of the standard pharmaceutical carriers, such as a phosphate buffered saline solution and various wetting agents. Other carriers may include additives used in tablets, granules, capsules, etc.

Typically such carriers contain excipients such as starch, milk, sugar, certain types of clay, gelatin, stearic acid or salts thereof, magnesium or calcium stearate, talc, vegetable fats or oils, gum, glycols or other known excipients. Such carriers may also include flavor and color additives or other ingredients. Compositions comprising such carriers are formulated by well-known conventional methods.

Increase of the Half-Life of rSIFN-co

Pegylation

Pegylation is the process by which polyethylene glycol chains are attached to protein and peptide drugs to increase pharmacokinetics by shielding these proteins and peptide drugs from proteolytic enzymes. See Harris and Chess, *Effect of pegylation on pharmaceuticals*. Nat Rev Drug Discov. 2003 March; 2 (3):214-21.

Pegylations is a well-established method for increasing the circulating half-life of protein and liposomal pharmaceuticals based on large hydrodynamic volume of polyethylene glycols. These polyethylene glycols shield the proteins and peptide drugs from renal clearance, enzymatic degradation and immune system recognition, thus their half-life and making them more acceptable to patients. See Molineux, *Pegylation: engineering improved pharmaceuticals for enhanced therapy*. Cancer Treat Rev. 2002 April; 28 Suppl A: 13-6. The author concludes that pegylation has beneficial effect on the quality of life of cancer patients.

Pegylation of the interferon increases the amount of time the interferon remains in the body by increasing the size of the interferon molecule by decreasing the rate of absorption, prolonging the half-life and the rate of interferon clearance. Thus, the duration of biological activity is increased with pegylated interferon over nonpegylated interferon, thus providing an advantage over nonpegylated interferons with less frequent administration and comparable tolerability. The author states that monotherapy with pegylated interferon produces a better response in some patients than monotherapy with the nonpegylated formulation. See Baker, *Pegylated Interferons*. Rev Gastroenterol Disord. 2001; 1 (2):87-99.

Sustained Release or Controlled Release

Sustained release delivery matrices and liposomes maybe used with rSIFN-co to create sustained release and controlled release formulation. See Robinson and Talmadge, *Sustained Release of Growth Factors*. In Vivo 2002 November-December; 16 (6): 535-40. The authors state that both pegylation and sustained release delivery matrices and liposomes improve the pharmacokinetic and pharmacodynamic properties of recombinant molecules, and thus by improving clinical efficacy these approaches increase patient compliance.

This invention provides recombinant super-compound interferon (rSIFN-co) comprising an agent or encapsulated by an agent, capable of affecting the half-life or delivery of said interferon. In an embodiment this agent is polyethylene glycol (PEG).

This invention further provides a method for treating or preventing viral diseases or tumors in a subject comprising administering to the subject an effective amount of the recombinant super-compound interferon (rSIFN-co) or its equivalent comprising an agent or encapsulated by an agent, capable of affecting the half-life or delivery of said interferon. In an embodiment this agent is polyethylene glycol (PEG).

This invention will be better understood from the examples which follow. However, one skilled in the art will readily appreciate that the specific methods and results discussed are merely illustrative of the invention as described more fully in the claims which follow thereafter.

EXPERIMENTAL DETAILS

IFN-con is a new interferon molecule constructed according to conservative amino acids in human IFN-α subtype using genetic engineering methods. It has been proven that IFN-con has broad-spectrum IFN activity, such as high anti-virus and tumor inhibition activity, especially for effectively treating hepatitis C.

E. Coli. codon was used to redesign rSIFN-co cDNA and then artificially synthesize cDNA of rSIFN-co from published Infergen® (interferon alfacon-1) DNA sequences and deduced amino acid sequences (FIG. 1).

In order to get pure rSIFN-co protein, rSIFN-co cDNA was cloned into E. Coli. high-expression vector, and L-arabinose, which can activate strong $P_{BAD}$ promoter in vectors, was used to induce high expression of rSIFN-co gene.

Example 1

Synthesis of E. Coli. cDNA Sequence
Redesign of rSIFN-co cDNA Sequence rSIFN-co cDNA was redesigned according to the codon usage of E. Coli. to achieve high expression in E. Coli. Deduced amino acid sequence from the redesigned cDNA sequence of rSIFN-co is completely coincidental with primitive amino acid sequence of published Infergen® (interferon alfacon-1) (FIG. 1).
rSIFN-co cDNA Sequence Synthesis
rSIFN-co cDNA 5'-Terminus and 3'-Terminus Semi-Molecular Synthesis Two semi-moleculars can be directly synthesized: rSIFN-co cDNA 5'—terminus 280 bp (fragment I) and 3'—terminus 268 bp (fragment II) by PCR. There are 41 bp overlapping among fragment II and fragment I.

(1) Chemical synthesis oligodeoxynucleotide fragment:
Oligomer A:
5'ATGTGCGACCTGCCGCAGACCCACTCCCTGGGTAACCGTCGTGCTCTG

ATCCTGCTGGCTCAGATGCGTCGTATCTCCCCGTTCTCCTGCCTGAAAGA

CCGTCACGAC3'

Oligomer B:
5'CTGAAAGACCGTCACGACTTCGGTTTCCCGCAGGAAGAATTCGACGGT

AACCAGTTCCAGAAAGCTCAGGCTATCTCCGTTCTGCACGAAATGATCCA

GCAGACCTTC3' SEQ ID NO: 11

Oligomer C:
5'GCTGCTGGTACAGTTCGGTGTAGAATTTTTCCAGCAGGGATTCGTCCC

AAGCAGCGGAGGAGTCTTTGGTGGAGAACAGGTTGAAGGTCTGCTGGATC

ATTTC3'

Oligomer D:
5'ATCCCTGCTGGAAAAATTCTACACCGAACTGTACCAGCAGCTGAACGA

CCTGGAAGCTTGCGTTATCCAGGAAGTTGGTGTTGAAGAAACCCCGCTGA

TGAAC3'

Oligomer E:
5'GAAGAAACCCCGCTGATGAACGTTGACTCCATCCTGGCTGTTAAAAAA

TACTTCCAGCGTATCACCCTGTACCTGACCGAAAAAAAATACTCCCCGTG

CGCTTGGG3'

Oligomer F:
5'TTATTCTTTACGACGCAGACGTTCCTGCAGGTTGGTGGACAGGGAGAA

GGAACGCATGATTTCAGCACGAACAACTTCCCAAGCGCACGGGGAGTATT

TTTTTTCGGTCAGG3'

PCR I for Fragment I: oligodeoxynucleotide B as template, oligodeoxynucleotide A and C as primers, synthesized 280 bp Fragment I.

| PCR I mixture | (units: μl) |
|---|---|
| sterilized distilled water | 39 |
| 10 × Pfu buffer (Stratagen American Ltd.) | 5 |
| dNTP mixture (dNTP concentration 2.5 mmol/L) | 2 |
| Oligomer A primer (25 μmol/L) | 1 |
| Oligomer C primer (25 μmol/L) | 1 |
| Oligomer B template (1 μmol/L) | 1 |
| Pfu DNA polymerase (Stratagen American Ltd.) (25 U/μl) | 1 |
| Total volume | 50 μl |

PCR cycle: 95° C. 2 m → (95° C. 45 s → 65° C. 1 m → 72° C. 1 m) × 25 cycle → 72° C. 10 m → 4° C.

PCR II for Fragment II: oligodeoxynucleotide E as template, oligodeoxynucleotide D and F as primers, synthesized 268 bp Fragment II.

| PCR II mixture | (units: μl) |
|---|---|
| sterilized distilled water | 39 |
| 10 × Pfu buffer (Stratagen American Ltd.) | 5 |
| dNTP mixture(dNTP concentration 2.5 mmol/L) | 2 |
| Oligomer D primer (25 μmol/L) | 1 |
| Oligomer F primer (25 μmol/L) | 1 |
| Oligomer E template (1 μmol/L) | 1 |
| Pfu DNA polymerase (Stratagen American Ltd.) (25 U/μl) | 1 |
| Total volume | 50 μl |

PCR cycle: the same as PCR I

Assembling of rSIFN-co cDNA

Fragment I and II were assembled together to get the complete cDNA molecular sequence of rSIFN-co using the overlapping and extending PCR method. Restriction enzyme Nde I and Pst I were introduced to clone rSIFN-co cDNA sequence into plasmid.

(1) Chemical synthesis primers
Oligomer G:
5'ATCGGCCATATGTGCGACCTGCCGCAGACCC3'

Oligomer H:
5'ACTGCCAGGCTGCAGTTATTCTTTACGACGCAGACGTTCC3'

| (2) Overlapping and extending PCR | |
|---|---|
| PCR mixture | (units: μl) |
| sterilized distilled water | 38 |
| 10 × Pfu buffer (Stratagen American Ltd.) | 5 |
| dNTP mixture (dNTP concentration 2.5 mmol/L) | 2 |
| primer G (25 μmol/L) | 1 |
| primer H (25 μmol/L) | 1 |
| *fragment I preduction (1 μmol/L) | 1 |
| *fragment II preduction (1 μmol/L) | 1 |
| Pfu DNA polymerase (Stratagen American Ltd.) (2.5 U/μl) | 1 |
| Total volume | 50μ |

*Separate and purify PCR production with StrataPrep PCR purification kit produced by Stratagen American Ltd. And dissolve into sterilized distilled water.
PCR cycle: the same as PCR I rSIFN-co Gene Clone and Sequence Analysis pLac T7 plasmid as cloning vector. pLac T7 plasmid is reconstructed with pBluescript II KS(+) plasmid produced by Stratagen (FIG. 3).

Stability of Expression Vector

Construction and Transformation of Expression Vector

Digested E. Coli. expression vector pHY-4 (see FIG. 3) with Nde I to linearize and subsequently digest with Xba I. Run 1% agarose gel electrophoresis, and purify the 4.8 kb pHY-4 Nde I-Xba I digest fragment with QIAEX II kit produced by QIAGEN Germany Ltd.

At the same time, the pHY-4 plasmid is double digested with Nde I-Xba I. Run 1% agarose gel electrophoresis and purify the 715 bp fragment. Ligate the rSIFN-co and pHY-4 fragments with T4 DNA ligase to construct the recombinant plasmid (See FIG. 4). Transform $DH_{5\alpha}$ competent cells with the recombinant plasmid. Spread the transformed cells on LB plate with Amp, 37° C. culture overnight.

Positive Cloning Strain Screening

Randomly choose E. Coli. colonies from above LB-plate, screening the positive strains containing recombinant vector by endonuclease digesting and PCR analysis. Name one of the positive recombinant plasmid pHY-5, and name the strain containing pHY-5 plasmid PVIII. Amplify and store the positive strain with glycerol in −80° C.

High Expression of rSIFN-co Gene in E. Coli.

In pHY-5 plasmid, rSIFN-co gene is under the control of strong promoter $P_{BAD}$. This promoter is positively and negatively regulated by the product of the gene araC. AraC is a transcriptional regulator that forms a complex with arabinose. In the absence of arabinose, the AraC dimer binds $O_2$ and $I_1$, forming a 210 bp loop. This conformation leads to a complete inhibition of transcription. In the presence of arabinose, the dimer is released from $O_2$ and binds $I_1$ and $I_2$ leading to transcription. Arabinose binding deactivates, represses, which even activates the transcription of $P_{BAD}$ promoter, which stimulates $P_{BAD}$, inducing high expression of rSIFN-co. rSIFN-co expression level in PVIII is more than 50% of the total E. Coli. protein.

Summary rSIFN-CO is a new interferon molecule artificially built according to the conservative amino acid of human a interferons. It has been proven as an effective anti-hepatitis drug.

In order to get enough pure rSIFN-co protein, a stable recombinant E. Coli. strain which highly expresses rSIFN-co protein was constructed.

First, according to published Infergen® (interferon alfacon-1) amino acid sequence, E. Coli. codon was used to synthesize the whole cDNA of rSIFN-co. This DNA fragment was sequenced, proving that the 501 bp codon sequence and TAA termination codon sequence are valid and identical to theocratic design. Subsequent analysis revealed that the N-terminus amino acid sequence and amino acid composed of rSIFN-co produced by the recombinant strain were both identical to the prediction.

The rSIFN-co cDNA was cloned into E. Coli. high-expression vector pHY-4 plasmid to construct the recombinant plasmid pHY-5. E. Coli. LMG194 strain was further transformed with pHY-4 plasmid to get stable rSIFN-co high-expression transformant. This transformant was cultured for 30 generations. The heredity of pHY-5 recombinant plasmid in E. Coli. LMG194 was normal and stable, and the expression of rSIFN-co was high and steady.

E. Coli. LMG194, which contains recombinant pHY-5 plasmid, is actually an ideal high-expression engineering strain.

REFERENCES

1. Blatt L M, Davis J M, Klein S B. et al. The biologic activity and molecular characterization of a novel synthetic interferon-alpha species, consensus interferon. Journal of Interferon and Cytokine Research, 1996; 16 (7):489-499.
2. Alton, K. et al: Production characterization and biological effects of recombinant DNA derived human IFN-α and IFN-γ analogs. In: De Maeger E, Schellekens H. eds. The Biology of Interferon System. 2nd ed. Amsterdam: Elsevier Science Publishers, 1983: 119-128
3. Pfeffer L M. Biologic activity of natural and synthetic type 1 interferons. Seminars in Oncology, 1997; 24 (3 suppl 9):S9-63-S9-69.
4. Ozes O N, Reiter Z, Klein S, et al. A comparison of interferon-con1 with natural recombinant interferons-α antiviral, antiproliferative, and natural killer-inducing activities. J. Interferon Res., 1992; 12:55-59.
5. Heathcote E J L, Keeffe E B, Lee S S, et al. Re-treatment of chronic hepatitis C with consensus interferon. Hepatology, 1998; 27 (4):1136-1143.
6. Klein M L, Bartley T D, Lai P H, et al. Structural characterization of recombinant consensus interferon-alpha. Journal of Chromatography, 1988; 454:205-215.
7. The Wisconsin Package, by Genetics Computer Group, Inc. Copyright 1992, Madison, Wis., USA
8. Nishimura, A et al: A rapid and highly efficient method for preparation of competent E. coli cells. Nuclei. Acids Res. 1990, 18:6169
9. All molecular cloning techniques used are from☐Sambrook, J., E. F. Fritsch and T. Maniatis. Molecular Cloning: A laboratory manual☐2nd ed. CSH Laboratory Press, Cold Spring Harbour, N Y. 1989.
10. Guzman, L. M et al: Tight regulation, modulation, and high-level express-ion by vectors containing the arabinose $P_{BAD}$ promoter. J. Bacteriol. 1995, 177☐4121~4130.

```
rSIFN-co cDNA SEQUENCE DESIGNED ACCORDING TO E. COLI. CODON
USAGE AND DEDUCED rSIFN-co AMINO ACID SEQUENCE
     5'       11        21        31        41        51
     +1  M  C  D  L  P  Q  T  H  S  L  G  N  R  R  A  L  I  L  L  A
```

```
  5'           71        81        91       101       111
+1    Q  M  R  R  I  S  P  F  S  C  L  K  D  R  H  D  F  G  F  P
  1 ATGTGCGACC TGCCGCAGAC CCACTCCCTG GGTAACCGTC GTGCTCTGAT CCTGCTGGCT
    TACACGCTGG ACGGCGTCTG GGTGAGGGAC CCATTGGCAG CACGAGACTA GGACGACCGA

5'          131       141       151       161       171
+1    Q  E  E  F  D  G  N  Q  F  Q  K  A  Q  A  I  S  V  L  H  E
 61 CAGATGCGTC GTATCTCCCC GTTCTCCTGC CTGAAAGACC GTCACGACTT CGGTTTCCCG
    GTCTACGCAG CATAGAGGGG CAAGAGGACG GACTTTCTGG CAGTGCTGAA GCCAAAGGGC

5'          191       201       211       221       231
+1    M  I  Q  Q  T  F  N  L  F  S  T  K  D  S  S  A  A  W  D  E
121 CAGGAAGAAT TCGACGGTAA CCAGTTCCAG AAAGCTCAGG CTATCTCCGT TCTGCACGAA
    GTCCTTCTTA AGCTGCCATT GGTCAAGGTC TTTCGAGTCC GATAGAGGCA AGACGTGCTT

5'          251       261       271       281       291
+1    S  L  L  E  K  F  Y  T  E  L  Y  Q  Q  L  N  D  L  E  A  C
181 ATGATCCAGC AGACCTTCAA CCTGTTCTCC ACCAAAGACT CCTCCGCTGC TTGGGACGAA
    TACTAGGTCG TCTGGAAGTT GGACAAGAGG TGGTTTCTGA GGAGGCGACG AACCCTGCTT

5'          311       321       331       341       351
+1    V  I  Q  E  V  G  V  E  E  T  P  L  M  N  V  D  S  T  L  A
241 TCCCTGCTGG AAAAATTCTA CACCGAACTG TACCAGCAGC TGAACGACCT GGAAGCTTGC
    AGGGACGACC TTTTTAAGAT GTGGCTTGAC ATGGTCGTCG ACTTGCTGGA CCTTCGAACG

5'          371       381       391       401       411
+1    V  K  K  Y  F  Q  R  I  T  L  Y  L  T  E  K  K  Y  S  P  C
301 GTTATCCAGG AAGTTGGTGT TGAAGAAACC CCGCTGATGA ACGTTGACTC CATCCTGGCT
    CAATAGGTCC TTCAACCACA ACTTCTTTGG GGCGACTACT TGCAACTGAG GTAGGACCGA

5'          431       441       451       461       471
+1    A  W  E  V  V  R  A  E  I  M  R  S  F  S  L  S  T  N  L  Q
361 GTTAAAAAAT ACTTCCAGCG TATCACCCTG TACCTGACCG AAAAAAAATA CTCCCCGTGC
    CAATTTTTTA TGAAGGTCGC ATAGTGGGAC ATGGACTGGC TTTTTTTTAT GAGGGGCACG

5'          491       501
+1    E  R  L  R  R  K  E  #
421 GCTTGGGAAG TTGTTCGTGC TGAAATCATG CGTTCCTTCT CCCTGTCCAC CAACCTGCAG
    CGAACCCTTC AACAAGCACG ACTTTAGTAC GCAAGGAAGA GGGACAGGTG GTTGGACGTC

481 GAACGTCTGC GTCGTAAAGA ATAA
    CTTGCAGACG CAGCATTTCT TATT
```

Example 2

Separation and Purification of rSIFN-co

1. Fermentation

Inoculate the recombinant strain in LB media, shaking (200 rpm) under 37° C. overnight (approximate. 18 h), then add 30% glycerol to the fermentation broth to get final concentration of 15%, allotted to 1 ml tube and kept in −20° C. as seed for production.

Add 1% of the seed to LB media, shaking (200 rpm) under 37° C. overnight to enlarge the scale of the seed, then add to RM media with a ratio of 10%, culturing under 37° C. Add arabinose (20% solution) to 0.02% as an inductor when the $OD_{600}$ reaches about 2.0. 4 hours after that, stop the culture process, collect the bacteria by centrifuge, resuspend the pellet with buffer A, and keep in −20° C. overnight. Thaw and break the bacteria by homogenizer, then centrifuge. Wash the pellet with buffer B, buffer C, and distilled water to get a relatively pure inclusion bodies.

2. Denaturation and Renaturation

Dissolve the inclusion body in Guanidine-HCl (or urea) of 6 mol/L. The solution will be a little cloudy. Centrifuge it at a speed of 10000 rpm. Determine the protein concentration of the supernatant. This supernatant is called "denaturation solution." Add the denaturation solution to renaturation buffer, and keep the final protein concentration under 0.3 mg/ml. It is better to add the totally denatured solution in three steps instead of one step. Keep the solution overnight under 4° C. Afterwards, dialyze 10 mol/L, 5 mol/L PB buffer and distilled water, then adjust its pH by 2 mol/L HAc-NaAc. Let it stand, then filtrate.

3. Purification

POROS HS/M Anion Exchange Chromatography:

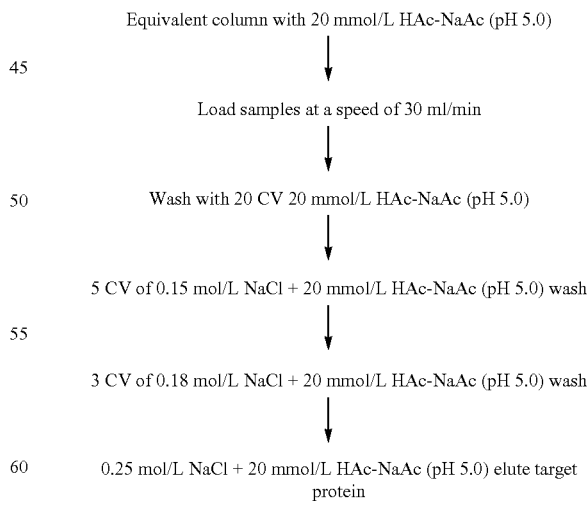

Chelating Sepharose™ fast flow: Add PB buffer of 0.2 mol/L (pH 6.6) and NaCl of 4 mol/L in the solution from HS to adjust solution pH to pH 6.0 and NaCl concentration to 1 mol/L.

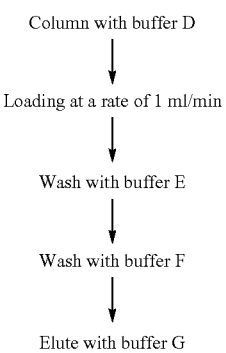

Column with buffer D
↓
Loading at a rate of 1 ml/min
↓
Wash with buffer E
↓
Wash with buffer F
↓
Elute with buffer G Condense the eluted solution by POROS HS/M. Sometimes a purification by sephacryl S-100 step can be added to meet stricter purity requirements.

Note:

Buffer A: 100 mmol/L Tris-HCl, pH 7.5-10 mmol/L EDTA-100 mmol/L NaCl

Buffer B: 50 mmol/L Tris-HCl, pH 7.5-1 mol/L Urea-10 mmol/L EDTA-0.5% Triton X-100

Buffer C: 50 mmol/L Tris-HCl, pH 7.5-2 mol/L Urea-10 mmol/L EDTA-0.5% Triton X-100

Buffer D: 1 mol/L NaCl—50 mmol/L $Na_2HPO_4$ (pH 5.5)

Buffer E: 1 mol/L NaCl—50 mmol/L $Na_2HPO_4$ (pH 5.0)

Buffer F: 1 mol/L NaCl—50 mmol/L $Na_2HPO_4$ (pH 4.0)

Buffer G: 1 mol/L NaCl—50 mmol/L $Na_2HPO_4$ (pH 3.6)

Renaturation buffer□0.5 mol/L Arginine□150 mmol/L Tris-HCl, pH 7.5-0.2 mmol/L EDTA

| LB Media: 1 L | |
|---|---|
| Tryptone | 10 g |
| Yeast extracts | 5 g |
| NaCl | 10 g |
| RM Media: 1 L | |
| Casein | 20 g |
| MgCl | 1 mmol/L (0.203 g) |
| $Na_2HPO_4$ | 4 g; |
| $KH_2PO_4$ | 3 g, |
| NaCl | 0.5 g |
| $NH_4Cl$ | 1 g |

After purification, the buffer was changed to PBS (pH 7.0) along with the step of condensing by POROS HS/M. This is called the "Protein Stock Solution." It can be directly used in the preparation of injections or sprays, or stored at 2-8° C.

Formula for Injection:

| | Solution | Lyophilized powder |
|---|---|---|
| Solution of rSIFN-co | 34.5 μg/ml | 34.5 μg/ml |
| PB (pH 7.0) | 25 mmol/L | 10 mmol/L |
| Glycine | — | 0.4 mol/L |
| NaCl | 0.1 mol/L | — |

For Spray:

| | |
|---|---|
| EDTA | 0.01% |
| Tween 80 | 0.05% |
| Trisodium citrate | 10 mmol/L |
| Glycerol | 1.26% |
| Sodium Chloride | 0.03% |
| Phenylmethanol | 0.5% |
| HSA | 0.1% |
| rSIFN-co | 10 μg/ml |

Quality Control Process

During purification, tests for protein content, protein purity, specific activity and pyrogen are conducted after each step. When the stock solution is obtained, all the tests listed in the table are done one after the other.

The quality of the product is controlled according to "Chinese Requirements for Biologics."

1. Original Protein Solution

Lowry

| Item of Test | Method |
|---|---|
| Protein Stock Solution: | |
| Test for Protein Content | Lowry |
| Test for Protein Purity | Non-reductive SDS-PAGE (sodium dodecyl sulfate polyacrylamide gel electrophoresis)<br>HPLC Analysis |
| Test for Molecular Weights | Reductive SDS-PAGE |
| Test for Specific Activity | According to Method in "Specific Activity Test of Interferon |
| Test for Leftover Exogenetic DNA | Using DNA Labeling and Detection Kit |
| Test for Activity of Leftover Antibiotics | According to Method in "Chemical and Other Test Methods for Biologics" |
| Test for Bacterial Endotoxin | According to Method in "Requirements for Bacterial Endotoxin Test of Biologics" |
| Test for Isoelectronic Point | Isoelectric Focusing Electrophoresis |
| Test for Identify Characteristics of the Protein | UV spectrum (range of wavelength: 190-380 nm)<br>Peptide Mapping (hydrolyzed by pancreatic enzyme, analyzed by C-18 column)<br>N-terminal Sequence Test<br>C-terminal Sequence Test<br>Circular Dichroism<br>Amino Acid Analysis |
| Semi-finished Product | |
| Test for Bacterial Endotoxin | According to Method in "Requirements for Bacterial Endotoxin Test of Biologics" |
| Product | |
| Appearance Check | |
| Chemical | According to Method in "Chemical and Other Test Methods for Biologics" |
| Test for Specific Activity | According to Method in "Specific Activity Test of Interferon |
| Sterility Test | According to Method in "c" |
| Abnormal Toxicity Test | Test on Mouse |

-continued

| Item of Test | Method |
|---|---|
| Pyrogen Test | According to Method in "Requirements for Pyrogen Test of Biologics" |
| Test for Stability of Product | |

Note:
"Chemical and Other Test Methods for Biologics", "Requirements for Pyrogen Test of Biologics" and "Requirements for Bacterial Endotoxin Test of Biologics" all can be found in the "Chinese Requirements for Biologics." "Chinese Requirements for Biologics," PAN Zhengan, ZHANG Xinhui, DUAN Zhibing, et al. Chinese Biologics Standardization committee. Published by Chemical Industry Publishing Company, 2000.

Example 3

Stability of Lyophilized Powder of Recombinant Super-Compound Interferon Injection The stability experiments were carried out with samples of lyophilized powder of recombinant super-compound interferon (rSIFN-co) injection in two specifications and three batches. The experiments started in April 2000.

1. Sample Source
Samples were supplied by Sichuan Huiyang Life-engineering Ltd., Sichuan Province. Lot: 990101-03, 990101-05, 990102-03, 990102-05, 990103-03, 990103-05

2. Sample Specifications
Every sample in this experiment should conform with the requirements in the table below.

TABLE 1

Standard of Samples in Experiment

| Items | Standards |
|---|---|
| 1. Appearance | white loose powder |
| 2. Dissolving time | dissolve rapidly in injection water (within 2 min) at room temperature |
| 3. Clarity | colorless liquid or with little milk-like glisten□should not be cloudy, impurity or with indiscernible deposit |
| 4. pH value | 6.5~7.5 |
| 5. Potency□IU/dose□ | 80%~150% of indicated quantity (9 μg: $4.5 \times 10^6$ IU, 15 μg: $7.5 \times 10^6$ IU) |
| 6. Moisture | no more than 3.0% (W/W) |

3. Experimental Content
Test samples at 2~8° C.: The test samples were put into a 2~8° C. refrigerator, then the above items of these samples were respectively tested in the $1^{st}$, $3^{rd}$, $6^{th}$, $9^{th}$, $12^{th}$, $18^{th}$, $24^{th}$, $30^{th}$, $36^{th}$ month. The results were recorded.

Test samples at 25° C.: The test samples were put into a thermostat at 25° C., then the above items of these samples were respectively tested in the $1^{st}$, $3^{rd}$, $6^{th}$, $9^{th}$, $12^{th}$, $18^{th}$, $24^{th}$, $30^{th}$ month. The results were recorded.

Test samples at 37° C.: The test samples were put into a thermostat at 37° C., then the above items of these samples were respectively tested in the $1^{st}$, $3^{rd}$, $6^{th}$, $9^{th}$, $12^{th}$, $18^{th}$, $24^{th}$ month. The results were recorded.

4. Results and Conclusion
1) At 37° C., according to data collected at designated points during testing and compared with data before testing, the potency began descending from the $6^{th}$ month and the changes in the three batches were similar. The appearance of other items had no changes.
2) At 25° C., according to data collected at designated points during testing and compared with data before the testing, the potency only had a little change, and the changes in the three batches were similar. The appearance of other items had no changes.
3) At 2-8° C., according to data collected at designated points during testing and compared with data before testing, the potency of the three batches all were stable. The appearance of other items also had no changes.

In conclusion, it is suggested that the lyophilized powder of recombinant super-compound interferon for injection should be better stored and transported at low temperatures. Without such conditions, the product can also be stored for short periods (i.e., 3 months) at room temperature.

Example 3.5

Production Flow Chart of rSIFN-co
1. Production
1.1 Fermentation
Use mixture of LB+M9 as culturing medium. The amount of innoculum will be 1.5%. Agitate to $OD_{600}$=0.4 (about 3.5 hours) under 32° C., then raise temperature to 42° C. Continue the agitation for another 6 hours, the expression of rSIFN-co will reach the maximum level. The examination under scanning of the gel resulting from SDS-PAGE shows that the level of expression is up to 57%, which is the highest standard in China.
1.2 Purification Centrifuge the bacteria solution to collect the bacterial pellet
↓
Physiological saline wash for two (2) times
↓
Adding buffer (50 mM Tris-HCl, 1 mM EDTA, 100 mM NaCl, 1% Triton X-100, 1-2M Urea), sonication to disrupt bacterial cells for 20-30 minutes
↓
Precipitate the buffer solution and wash a few times until the color turns into pure white
↓
Use 7M Guanidine HCl to denature
↓
Dilute the Guanidine HCl to renature, stay overnight
↓
Use Sephadex G25 to desalt
↓
Use 0.1M NaCl to apply CM-Sepharose
↓
Do stepwise elution to collect the active peak
↓
After the active peak is desalted, apply to HPLC positively charged column
↓
Use 0.1M NaCl to do stepwise elution, collect active peak which is the product of rSIFN-co
↓
Add protection carrier and lyophiling agent
↓
Separate lyophilized materials (rSIFN-co)

The purity of the product (rSIFN-co) from this production procedure is shown to 95% under the test of SDS-PAGE where molecular weight is 14.5 Kda. The reverse phase HPLC shows a single peak and the purity is up to 97%. Its specific activity is up to $1\times10^9$ IU/mg protein.

1.3 Packaging and Inspection

After HPLC purification, 2% human serum albumin, 1% sucrose and 1% glucose are added to the rSIFN-co. It is then separated and lyophilized into injection sample. When tested under the Wish-VVS inspection system, the result was $4.5\times10^8$ IU. When tested with aseptic inspection and pyrogen inspection under the standard requirement of China, the results were negative. This result complies with the requirements for IV injection.

2. Quality Control 2.1 Biological Characteristics (1) When using LB+M9 to cultivate bacteria, the characteristics should match with the typical characteristics of E-coli bacteria. No other bacteria were detected.

(2) When smeared for Gram staining and inspected under a microscope, it is bacteria-negative.

(3) Reaction to antibiotics is the same as those original bacteria.

(4) Electron microscope inspection shows typical characteristics of E-coli bacteria. No mycoplasma, virus spore or other micro pollutes was detected.

(5) Biochemical reaction test shows characteristics of E-coli bacteria.

2.2 Quality Control of Interferon Expression (1) Interferon expression (cultivated in an agitating platform) matches the amount of expression in original input bacteria.

(2) When tested with anti-interferon serum, a reaction is shown.

(3) Plasmid inspection: Restriction digest matched with the original plasmid.

2.3 Bacteria Strain Product

Bacteria strain product denotes the specimen from the original bacteria strain that was produced from the procedures shown in 1.2.

The bacteria strain product should be inspected as follows to make sure there is no derivation: Use LB to plate 2-3 pieces and cultivate. Separate and take 5-10 bacteria groups for the test of interferon expression. Repeat the test at least two (2) times. Only use the one which shows the highest % to be the bacteria strain product.

2.4 Inoculum

The inoculum denotes the chosen bacteria strain product after fermentation. The amount, cultivation time and most appropriate OD value of inoculum can be decided according to bacteria strain. An anti-polluted bacteria procedure should apply for whatever inoculum would be produced.

2.5 Growing of Bacteria Strain

Growing of bacteria strain would be done in a Bacteria Free room environment where no more than one bacterium is growing in the same room. Same culturing medium will be used for both bacteria strain and inoculum. The one used in rSIFN-co is LB.

2.6 Fermentation (1) Fermentation only takes place in a clean fermentation room with a single bacteria fermentation environment.

(2) Cleaning of fermentation container and tube is done twice, before and after the insertion of culturing medium. Then, the container should be frozen to reach the appropriate temperature for inoculum.

(3) Avoid using antibiotic which might affect cell growth in the culturing medium.

(4) Fermentation parameters like temperature, pH value, dissolved oxygen and time required could be varied according to different types of bacterial strains.

2.7 Bacteria Collection (1) Centrifuge the bacteria solution to collect bacteria or use another method. All apparatus should be cleaned before and after the operation. The waste solution should be drained after the cleaning procedure.

(2) The bacteria should be kept under 4-8° C. if they are going to be split within 24 hours. Otherwise, they should be kept under −30° C. Those are kept under such conditions can be used within 6 months.

2.8 Bacteria Cell Lysis (1) Use appropriate buffer solution to balance the bacteria strain. Cell lysis can be done by physical, chemical or biological methods. Use centrifuge to precipitate the bacteria and apply cleaning solutions.

(2) If the chemical method is used to split cells, no solutions harmful to human beings should be used.

2.9 Purification (1) Purification will get rid of most of the non-interferon contents. In the process of purification, no toxic materials should be found if extra elements are added.

(2) If using antibody affinity chromatography for purification, there should be an indication of the source and degree of purity. Also, inspection of small quality IgG should be performed.

(3) During the process of purification, clearance of pyrogen is critical. All apparatus should be checked to eliminate this interference.

(4) The highly concentrated interferon is known as "intermediate product". After inspection and tests, add albumin to raise the concentration to 2% which is now known as "albumin intermediate product". After examination and tests, it should be kept at −30° C. and never thawed before use. This product should be used within 6 months.

(5) The albumin that is used in this process should also fulfill tests and requirements such as: negativity under RBSAG inspection and an indication of the ratio among monomer, dimer and polymer.

2.10 Production into Tube Product (1) Filtration: Use 0.22μ membrane to filter the bacteria. The product should be handled with aseptic techniques. Samples should be taken to test the value of the interferon.

(2) Dilution: Dilute the albumin intermediate product with 2% diluent. No preservative should be added. The product can be lyophilized after the aseptic inspection and pyrogen inspection.

2.11 Lyophilization

The lyophilization should not affect the activity of interferon, and the water content of said lyophilite will be maintained.

2.12 Inspection

There are two types of rSIFN-co made. One is for injection and the other for topical use. The specifications for the two are different. There are intermediate products and final products for each type. In the injection type, intermediate products include purified interferon, albumin intermediate product, and bacteria free albumin intermediate product. Final product from the injection type will denote only lyophilized product. The intermediate product in the topical type denotes only purified interferon. The final product from the topical type denotes only separated packed liquid formed lyophilized products.

2.13 Packaging

There is different packaging for the injection type and the topical type.

2.14 Storage

The product should be kept at 4° C. The purification solution should not be stored in a frozen state.

2.15 Expiration

The expiration period is two (2) years after the lyophilization procedure for lyophilized products. The expiration period is 6 months after individual packing for liquidated products.

Example 4

Preparation of rSIFN-co

| Preparation of lyophilized injection | |
|---|---|
|  | Lyophilized powder |
| Stock Solution of rSIFN-co | 34.5 µg/ml |
| PB (pH 7.0) | 10 mmol/L |
| Glycine | 0.4 mol/L |

Preparation technique: Weigh materials according to recipe. Dissolve with sterile and pyrogen-free water. Filter through 0.22 µm membrane to de-bacterialize, preserve at 6-10° C. Fill in vials after affirming they are sterile and pyrogen-free, 0.3 ml/vial or 0.5 ml/vial, and lyophilize in freeze dryer.

| Preparation of liquid injection | |
|---|---|
|  | Solution |
| Stock Solution of rSIFN-co | 34.5 µg/ml |
| PB (pH 7.0) | 25 mmol/L |
| NaCl | 0.1 mol/L |

Preparation: Weigh materials according to recipe. Add to desired level with sterile and pyrogen-free water. Filter through 0.22 µm membrane to de-bacterialize, preserve at 6-10° C. Fill in airtight vial after affirming it is sterile and non-pyrogen at 0.3 ml/vial or 0.5 ml/vial. Store at 2-10° C., and protect from light.

Example 4.5

Acute Toxicity of rSIFN-co

Treat mice with large dose (150 µg/kg, equal to 1000 times of the normal dose per kilo used in treatment of adult patients) of rSIFN-co at one time by intramuscular injection. Then observe and record their deaths and toxic reactions. Results show that: 24 hours after injection, no abnormal reaction had been recorded. The organs of the animals which had been selected to be killed also had no signs of abnormal changes. Those remaining mice were all kept alive and were normal after two weeks. The weights of mice in the experimental group and control group all increased, and the ratio of increase showed no obvious difference between the two groups ($P>0.05$) according to their weights on the fourteenth day. No abnormal changes were seen from the main organs of those mice after two weeks.

1. Experimental Material 1.1 Animals 40 healthy adult mice, weighing 18-22 g, half male and half female, qualified by Sichuan experiment animal control center.

1.2 Medicines rSIFN-co (Provided by Sichuan Huiyang Life-engineering Ltd.) sterilized solution, 0.15 mg/ml, Lot: 981201 rSIFN-co was administered i.m. in saline.

2. Method

Separate the 40 mice into two groups randomly, one for experimental medicine, another for control. Inject medicines or saline at the same ratio (0.1 ml/10 g) through muscle to each mouse according to which group they belong. (150 µg/kg of rSIFN-co for experimental group; and saline for control group). After injection, observe and record acute toxicity shown in mice. Kill half of the mice (male and female each half) to check whether there were any abnormal pathologic changes in their main organs, such as heart, spleen, liver, lung, kidney, adrenal gland, stomach, duodenum, etc. after 24 hours. Those that remain are kept and observed until the fourteenth day. Weigh all mice, kill them, and then observe the appearance of the organs listed above to see if there are any abnormalities. Take pathological tissue and examine it, using the examination to assess the difference in weight increases in the two groups.

3. Results

Results show that there was no acute toxicity seen after all mice were treated with i.m. rSIFN-co with 150 µg/kg at a time, equal to 1000 times the normal dose per kilo used in treatment of adult patients. In the 14 days after injection, all mice lived well. They ate, drank, exercised, and excreted normally and showed normal hair conditions. None of them died. The observation of the main organs of the randomly selected mice shows no abnormal changes 24 hours after injection. 14 days after injection, all remaining mice were killed. Autopsies also showed no changes. The weights of mice in the two groups all increased, but no obvious difference was shown when accessed with statistic method ($p>0.05$). See Table 6.1:

TABLE 6.1

| Influence to weights of mice after injection of rSIFN-co | | | | | |
|---|---|---|---|---|---|
| Group | Dose | Animal | Weights before injection (g) | Weights after injection (g) | Increased value of weights (g) |
| Control | 0 | 20 | 19.8 ± 1.7 | 30.8 ± 2.8 | 11.0 ± 2.9 |
| rSIFN-co | 150 | 20 | 19.4 ± 1.7 | 32.1 ± 3.3 | 12.7 ± 4.3 |

4. Conclusion

Under conditions of this experiment, there were no toxic reactions in all mice after injection of rSIFN-co with 150 µg/kg. The conclusion can be reached that the maximum tolerable dose of i.m. in mice is 150 µg/kg, which is equal to 1000 times the normal dose per kilo used in treatment of adult patients.

2002 rSIFN-co Drug Inspection Report: Nov. 14, 2002 rSIFN-co Drug Inspection Report by China Drugs & Biological Products Inspection Laboratory.

On Nov. 14, 2000, 80 vials of rSIFN-co each containing 9 µg (micrograms) provided by Sichuan Biotechnology Research Center were tested. rSIFN-co Drug was white in color with produced no precipitation when water was added.

The pH value was 6.9 while the standard was between 6.5 to 7.5. The water content of rSIFN-co was 2.3% while the standard was smaller than 3.0%. Test for bacteria showed no bacterial grown. rSIFN-co passed pyrogen test. The toxicity test on mice showed no harm. Mice were alive and gained weight. The specific activity test was $6.0 \times 10^6$ IU/vial while the standard was between $3.6 \times 10^6$ IU/vial to $6.8 \times 10^6$ IU/vial. The identification test was positive.

Example 5

Crystal Growth of rSIFN-co and Test of Crystallography Parameter

Crystal of rSIFN-co. Two types of crystal were found after systematically trial and experiment. (See FIGS. 7-9)

1. Crystal Growth

Dissolve rSIFN-co protein with pure water ($H_2O$) to 3 mg/ml in density. Search of crystallization by using Hampton Research Crystal Screen I and II which was made by Hampton Company. By using Drop Suspension Diffusion Method, liquid 500 μl, drop 1 μl protein+1 μl liquid, in 293K temperature. First 2 different types of small crystals were found as listed in Table 12.1.

TABLE 12.1

Screen of rSIFN-co Crystallin

| | Condition | |
|---|---|---|
| | I | II |
| Diluent | 0.1M Tris-HCl PH = 8.75 | 0.1M HEPES PH = 7.13 |
| Precipitant | 17.5% (w/v) PEG550 MME | 10% (w/v) PEG6K |
| Additives | 0.1M NaCl | 3% (w/v) MPD |
| Temperature | 293 K | 293 K |
| Crystal Size (mm) | 0.2 × 0.2 × 0.1 | 0.6 × 0.02 × 0.02 |
| Crystallogram | FIG. 7 | FIG. 8 |

2. Data Collection and Processing

Crystal I was used to collect X-Ray diffraction data and preliminary analysis of crystallography. Parameters were also tested. The diffraction data was collected under room temperature. Crystal I (Condition I) was inserted into a thin siliconized wall tube. Using Bruker-AXS Smart CCD detector, the light source is CuKα (λ=1.5418 Å) generated by Nonius FR591 X-ray generator. Light power 2000 KW (40 kv×50 mA), wave length 1.00 Å, under explosion 60 second, Δφ=2°, the distance between crystal and detector was 50 mm. Data was processed for using Proteum Procedure Package by Bruker Company. See FIG. 9 for crystal diffraction pattern (partially). See Table 12.2 for the result of the process.

TABLE 12.2

Results of Crystallography Parameters

| Parameters | |
|---|---|
| a (Å) | 82.67 |
| b (Å) | 108.04 |
| c (Å) | 135.01 |
| α (Å) | 90.00 |
| β (Å) | 90.00 |
| γ (Å) | 98.35 |
| Space Group | P2 or P2$_1$ |
| Sharpness of separation | 5 Å |

TABLE 12.2-continued

Results of Crystallography Parameters

| Parameters | |
|---|---|
| Asymmetric molecule # | 10 |
| Dissolution | 57.6% |

Besides, there was no crystal growth of rSIFN-co based on previous publications. The closest result to the rSIFN-co was huIFN-α2b but the screen was very complicated. After seeding 3 times, crystal grew to 0.5×0.5×0.3 mm, sharpness of separation was 2.9 Å, space group was P2$_1$. The crystals were also big, asymmetric molecule number was 6, and dissolution was about 60%.

Clinical Report 1: Evidence of effectiveness of rSIFN-co in healing cancer. See FIGS. 17A-H.

The ultra sound inspection showed an enlarged right ovary and abdominal fluid. The patient was suspected of having ovarian cancer.

Western China No. 2 Hospital reported a patient with ovarian cancer and breast gland cancer diagnosed on Jul. 14, 2004. Her serum contained CA-125>600 U/ml and CA-153>250 U/ml. Also 2000 ml abdominal water was found. On Jul. 16, 2004, malignant cancer cells and low differential gland cancer cells (likely a low graded differential Adenocarcinoma) were found from the abdominal water and cancer cells and death materials were found from the mammary gland check up. On Aug. 4, 2004, it was concluded diagnosis as ovary cancer.

The patient was treated with rSFIN-co starting Jul. 14, 2004. She was injected with 15 μg of rSFIN-co on Jul. 14, 2004, Jul. 16, 2004, Jul. 18, 2004, Jul. 20, 2004 and Jul. 22, 2004 respectively. She began chemotherapy on Jul. 22, 2004. On Aug. 3, 2004 abdominal surgery was performed. It was expected that her abdominal water would be more than 2000 ml. However, only 200 ml were recorded. On Aug. 4, 2004 the examination results showed she had mammary gland cancer, ovarian cancer of right and left ovary and lymphoma. She was treated with rSIFN-co and chemotherapy at the same time. She did not have operation on mammary glands.

On Dec. 27, 2004 the examination report showed her CA-125 dropped to 5 U/ml and CA-153 dropped to 13 U/ml. On Feb. 25, 2005, her PET examination report from Daping Hospital, Third Military Medical University of PRC showed there was no obvious abnormal difference on metabolic reactions on her body and brain. The symptoms of her mammary gland cancer disappeared. No traces of cancer were found.

PET imaging: On Feb. 25, 2005 PET imaging report on Feb. 25, 2005 of this 43 years old patient diagnosis with left side ovary cancer and was treated with rSIFN-co since Jul. 14, 2004; PET imaging was done at PET Center of the Daping Hospital, Third Military Medical University of PRC.

Fasting patient was intravenously injected with $^{18}$F-FDG14.8 mCi. Brain images were taken 50 minutes after injection. The images were clear, no obvious abnormal increase or decrease of radiation were observed on cerebral epidermis, both sides of cerebellum, bothسides of hypothalamus and basal.

Whole body imaging was done 60 minutes after injection. The images were clear. No obvious abnormal increase or decrease of radiation on neck, lungs, mediastinum, liver, both sides of adrenals, abdominal lymph gland, pelvic cavity, bones.

The image of heart was clear.

Result: The FDG-PET images of the whole body and brain did not show abnormal FDG metabolic increase or decrease after five-and-half (5.5) months of rSIFN-co treatment of ovarian ovary cancer.

Conclusion: Comparison of CA-153 and CA-125 levels before and after rSFIN-co treatment evidenced that rSFIN-co is effective against breast and ovarian cancer.

Clinical Report 2: A kidney cancer patient was treated in the following manner. In a half-month period, the patient was given 3 injections of 9 µg of rSIFN-co and 3 injections of 15 µg of rSIFN-co. In the one and a half months following these injections, he received 24 µg injections of rSIFN-co every day. A kidney biopsy showed no metastasis after this course of treatment. The patient showed a full recovery. Every half year after recovery, the patient received 15 µg injections of rSIFN-co 15 times over a one-month period.

Example 6 rSIFN-co Inhibits HBV-DNA Duplication and Secretion of HBsAg and HBeAg

Materials

Solvent and Dispensing Method: Add 1 ml saline into each vial, dissolve, and mix with MEM culture medium at different concentrations. Mix on the spot.

Control drugs: IFN-α2b (Intron A) as lyophilized powder, purchased from Schering Plough. $3 \times 10^6$ IU each, mix to $3 \times 10^6$ IU/ml with culture medium; Infergen® (liquid solution), purchased from AMGEN, 9 µg, 0.3 ml each, equal to $9 \times 10^6$ IU, and mix to $9 \times 10^6$ IU/ml with culture medium, preserve at 4° C.; 2.2.15 cell: 2.2.15 cell line of hepatoma (Hep G2) cloned and transfected by HBV DNA, constructed by Mount Sinai Medical Center.

Reagent: MEM powder, Gibco American Ltd. cattle fetal blood serum, HycloneLab American Ltd. G-418 (Geneticin); MEM dispensing, Gibco American Ltd.; L-Glutamyl, imported and packaged by JING KE Chemical Ltd.; HBsAg and HBeAg solid-phase radioimmunoassay box, Northward Reagent Institute of Chinese Isotope Ltd.; Biograncetina, Northern China Medicine; And Lipofectin, Gibco American Ltd.

Experimental goods and equipment: culture bottle, Denmark Tunclon™; 24-well and 96-well culture board, Corning American Ltd.; Carbon Dioxide hatching box, Shel-Lab American Ltd.; MEM culture medium 100 ml: 10% cattle fetal blood serum, 3% Glutamyl 1%, G418 380 µg/ml, biograncetina 50 U/ml.

Method:

2.2.15 cell culture: Added 0.25% pancreatic enzyme into culture box with full of 2.2.15 cell, digest at 37° C. for 3 minutes, and add culture medium to stop digest and disturb it to disperse the cells, reproduce with ratio of 1:3. They will reach full growth in 10 days.

Toxicity test: Set groups of different concentrations and a control group in which cells are not acted on with medicine. Digest cells, and dispense to a 100,000 cell/ml solution. Inoculate to 96-well culture board, 200 µl each well, culture at 37° C. for 24 h with 5% $CO_2$. Test when simple cell layer grows.

Dispense rSIFN-co to $1.8 \times 10^7$ IU/ml solution, then prepare a series of solutions diluted at two-fold gradients. Add into 96-well culture board, 3 wells per concentration. Change the solution every 4 days. Test cytopathic effect by microscope after 8 days. Fully destroy as 4, 75% as 3, 50% as 2, 25% as 1, zero as 0. Calculate average cell lesion and inhibition rate of different concentrations. Calculate $TC_{50}$ and $TC_0$ according to the Reed Muench method.

$$TC_{50} = \text{Antilog}\left(B + \frac{50-B}{A-B} \times C\right)$$

A=log>50% medicine concentration, B=log<50% medicine concentration, C=log dilution power Inhibition test for HBeAg and HBsAg: Separate into positive and negative HBeAg and HBsAg contrast groups, cell contrast group and medicine concentration groups. Inoculate 700,000 cells/ml of 2.2.15 cell into 6-well culture board, 3 ml each well, culture at 37° C. for 24 h with 5% $CO_2$, then prepare 5 gradiently diluted solutions with 3-fold as the grade (Prepare 5 solutions, each with a different protein concentration. The concentration of Solution 2 is 3 times lower than that of Solution 1, the concentration of Solution 3 is 3 times lower than that of Solution 2, etc.) $4.5 \times 10^6$ IU/ml, $1.5 \times 10^6$ IU/ml, $0.5 \times 10^6$ IU/ml, $0.17 \times 10^6 1$ U/ml, and $0.056 \times 10^6 1$ U/ml, 1 well per concentration, culture at 37° C. for 24 h with 5% $CO_2$. Change solutions every 4 days using the same solution. Collect all culture medium on the $8^{th}$ day. Preserve at −20° C. Repeat test 3 times to estimate HBsAg and HBeAg with solid-phase radioimmunoassay box (Northward Reagent Institute of Chinese Isotope Ltd.). Estimate cpm value of each well with a γ-accounting machine.

Effects calculation: Calculate cpm mean value of contrast groups and different-concentration groups and their standard deviation, P/N value such as inhibition rate, IC50 and SI.

$$\text{Antigen inhibition rate (\%)} = \frac{A-B}{A} \times 100 \qquad 1)$$

A=cpm of control group; B=cpm of test group;
2) Counting the half-efficiency concentration of the medicine $$\text{Antigen inhibition } IC_{50} = \text{Antilog}\left(B + \frac{50-B}{A-B} \times C\right)$$

A=log>50% medicine concentration, B=log<50% medicine concentration, C=log dilution power
3) SI of interspace-conformation changed rSIFN-co effect on HBsAg and HBeAg in 2.2.15 cell culture $$SI = \frac{TC_{50}}{TC_{50}}$$

4) Estimate the differences in cpm of each dilution degree from the control group using student t test Southern blot: (1) HBV-DNA extract in 2.2.15 cell: Culture cell 8 days. Exsuction culture medium (Separate cells from culture medium by means of draining the culture medium). Add lysis buffer to break cells, then extract 2 times with a mixture of phenol, chloroform and isoamyl alcohol (1:1:1), 10,000 g centrifuge. Collect the supernatant adding anhydrous alcohol to deposit nucleic acid. Vacuum draw, re-dissolve into 20 µlTE buffer. (2) Electrophoresis: Add 6×DNA loading buffer, electrophoresis on 1.5% agarose gel, IV/cm, at fixed pressure for 14-18 h. (3) Denaturation and hybridization: respectively dip gel into HCl, denaturation buffer and neutralization buffer. (4) Transmembrane: Make an orderly transfer of DNA to Hybond-N membrane. Bake, hybridize and expose with dot blot hybridization. Scan and analyze relative density with gel-pro software. Calculate inhibition rate and $IC_{50}$.

Results

Results from Tables 4.1, 4.2 and 4.3 show: After maximum innocuous concentration exponent culturing for 8 days with 2.2.15 cell, the maxima is $9.0 \pm 0 \times 10^6$ IU/ml average inhibition rate of maximum innocuous concentration rSIFN-co to HBeAg is 46.0±5.25% (P<0.001), $IC_{50}$ is $4.54 \pm 1.32 \times 10^6$ IU/ml, SI is 3.96; rate to HBsAg is 44.8±6.6%, $IC_{50}$ is $6.49 \pm 0.42 \times 10^6$ IU/ml, SI is 2.77. This shows that rSIFN-co can significantly inhibit the activity of HBeAg and HBsAg, but that the IFN of the contrast group and Infergen® cannot. It has also been proven in clinic that rSIFN-co can decrease HBeAg and HBsAg or return them to normal levels.

TABLE 4.1

Results of inhibition rate of rSIFN-co to HBsAg and HBeAg

First batch: (rSIFN-co)

| Concentration (×10⁴ IU/ml) | First well | Second well | Third well | Inhibition rate First well | Inhibition rate Second well | Inhibition rate Third well | Average inhibition rate | Accumulation | 1-Accumulation | Accumulated inhibition rate |
|---|---|---|---|---|---|---|---|---|---|---|
| \multicolumn{11}{c}{Inhibition effect to HBeAg} |
| 900 | 9026 | 8976 | 10476 | 0.436227 | 0.43935 | 0.345659 | 0.407079 | 0.945909 | 0.592921 | 0.614693546 |
| 300 | 9616 | 12082 | 10098 | 0.3993754 | 0.245347 | 0.369269 | 0.337997 | 0.5388299 | 1.254924 | 0.300392321 |
| 100 | 9822 | 16002 | 12800 | 0.386508 | 0.0005 | 0.2005 | 0.195836 | 0.200833 | 2.059088 | 0.08867188 |
| 33.33333 | 15770 | 19306 | 16824 | 0.014991 | 0 | 0 | 0.004997 | 0.0049969 | 3.054091 | 0.001633453 |
| 11.11111 | 19172 | 22270 | 18934 | 0 | 0 | 0 | 0 | 0 | 4.054091 | 0 |
| Control | Cell | 16010 | | Blank | 0 | | Dilution | 3 | IC50 | 602.74446016 |
| \multicolumn{11}{c}{Inhibition effect to HBsAg} |
| 900 | 7706 | 7240 | 7114 | 0.342155 | 0.381936 | 0.392693 | 0.372261 | 0.922258 | 0.627739 | 0.595006426 |
| 300 | 8856 | 7778 | 9476 | 0.2439816 | 0.336008 | 0.191053 | 0.257014 | 0.5499972 | 1.370724 | 0.286349225 |
| 100 | 10818 | 10720 | 10330 | 0.07649 | 0.084856 | 0.118149 | 0.093165 | 0.292983 | 2.27756 | 0.113977019 |
| 33.33333 | 10744 | 11114 | 10570 | 0.082807 | 0.051221 | 0.097661 | 0.07723 | 0.1998179 | 3.20033 | 0.058767408 |
| 11.11111 | 10672 | 9352 | 10810 | 0.088953 | 0.201639 | 0.077173 | 0.122588 | 0.122588 | 4.077742 | 0.02918541 |
| Control | Cell | 11714 | | Blank | 0 | | Dilution | 3 | IC50 | 641.7736749 |

| Concentration (×10⁴ IU/ml) | First well | Second well | Third well | Inhibition rate First well | Inhibition rate Second well | Inhibition rate Third well | Average inhibition rate | Accumulation | 1-Accumulation | Accumulated inhibition rate |
|---|---|---|---|---|---|---|---|---|---|---|
| \multicolumn{11}{c}{Second batch: (rSIFN-co)} |
| \multicolumn{11}{c}{Inhibition effect to HBeAg} |
| 900 | 7818 | 8516 | 9350 | 0.554378 | 0.514592 | 0.467054 | 0.512008 | 1.371181 | 0.487992 | 0.737521972 |
| 300 | 10344 | 10628 | 9160 | 0.4103967 | 0.394209 | 0.477884 | 0.427497 | 0.8591731 | 1.060496 | 0.447563245 |
| 100 | 12296 | 14228 | 13262 | 0.299134 | 0.18901 | 0.244072 | 0.244072 | 0.4316522 | 1.816423 | 0.19201839 |
| 33.33333 | 15364 | 17414 | 16188 | 0.124259 | 0.00741 | 0.77291 | 0.069653 | 0.1876045 | 2.74677 | 0.063933386 |
| 11.11111 | 17386 | 13632 | 15406 | 0.009006 | 0.222982 | 0.121865 | 0.117951 | 0.117951 | 3.628819 | 0.03148073 |
| Control | Cell | 16962 | | Blank | 0 | | Dilution | 3 | IC50 | 365.9357846 |
| \multicolumn{11}{c}{Inhibition effect to HBsAg} |
| 900 | 5784 | 6198 | 5792 | 0.498265 | 0.462353 | 0.497571 | 0.486063 | 0.893477 | 0.513937 | 0.634835847 |
| 300 | 7150 | 8534 | 8318 | 0.379771 | 0.259715 | 0.278452 | 0.30598 | 0.4074138 | 1.207957 | 0.252210647 |
| 100 | 9830 | 11212 | 10210 | 0.147294 | 0.027412 | 0.11433 | 0.096345 | 0.101434 | 2.111612 | 0.04583464 |
| 33.33333 | 13942 | 12368 | 13478 | 0 | 0 | 0 | 0 | 0.0050891 | 3.111612 | 0.001632835 |
| 11.11111 | 12418 | 11634 | 11352 | 0 | 0 | 0.015267 | 0.005089 | 0.005089 | 4.106523 | 0.001237728 |
| Control | Cell | | | Blank | 0 | | Dilution | 3 | IC50 | 611.0919568 |
| \multicolumn{11}{c}{Third batch: (rSIFN-co)} |
| \multicolumn{11}{c}{Inhibition effect to HBeAg} |
| 900 | 9702 | 9614 | 8110 | 0.428016 | 0.433204 | 0.521872 | 0.461031 | 1.316983 | 0.538969 | 0.709599543 |
| 300 | 8914 | 10032 | 8870 | 0.4744723 | 0.40856 | 0.477066 | 0.453366 | 0.8559525 | 1.085603 | 0.440859127 |
| 100 | 16312 | 12688 | 13934 | 0.038321 | 0.251975 | 0.178517 | 0.156271 | 0.402586 | 1.929332 | 0.172641621 |
| 33.33333 | 15080 | 12814 | 13288 | 0.110954 | 0.244547 | 0.216602 | 0.190701 | 0.2463153 | 2.738631 | 0.082519158 |
| 11.11111 | 21928 | 15366 | 15728 | 0 | 0.094093 | 0.072751 | 0.0055615 | 0.055615 | 3.683017 | 0.014875633 |
| Control | Cell | 17544 | | Blank | 0 | | Dilution | 3 | IC50 | 382.0496935 |
| \multicolumn{11}{c}{Inhibition effect to HBsAg} |
| 900 | 5616 | 6228 | 5346 | 0.496864 | 0.442035 | 0.521054 | 0.486651 | 0.763125 | 0.513349 | 0.597838293 |
| 300 | 8542 | 8590 | 7096 | 0.234725 | 0.230425 | 0.364272 | 0.276474 | 0.2764738 | 1.236875 | 0.182690031 |
| 100 | 11420 | 11360 | 11394 | 0 | 0 | 0 | 0 | 0 | 2.236875 | 0 |
| 33.33333 | 12656 | 11582 | 13110 | 0 | 0 | 0 | 0 | 0 | | 0 |
| 11.11111 | 13142 | 12336 | 13342 | 0 | 0 | 0 | 0 | 0 | 4.236875 | 0 |
| Control | Cell | 11528 | | Blank | 0 | | Dilution | 3 | IC50 | 694.7027149 |

HBeAg: Average IC50: 450.2434 SD: 132.315479

HBsAg: Average IC50: 649.1894 SD: 42.29580

TABLE 4.2

Results of inhibition rate of Intron A(IFN-α2b) to HBsAg and HBeAg

| Concentration (×10⁴ IU/ml) | First well | Second well | Third well | Inhibition rate First well | Inhibition rate Second well | Inhibition rate Third well | Average inhibition rate | Accumulation | 1-Accumulation | Accumulated inhibition rate |
|---|---|---|---|---|---|---|---|---|---|---|
| Inhibition effect to HBeAg | | | | | | | | | | |
| 300 | 14918 | 11724 | 9950 | 0 | 0.029711 | 0.176529 | 0.068747 | 0.068747 | 0.931253 | 0.068746724 |
| 100 | 14868 | 16890 | 15182 | 0 | 0 | 0 | 0 | 0 | 1.931253 | 0 |
| 33.33333 | 16760 | 21716 | 16400 | 0 | 0 | 0 | 0 | 0 | 2.931253 | 0 |
| 11.11111 | 20854 | 15042 | 16168 | 0 | 0 | 0 | 0 | 0 | 3.931253 | 0 |
| 3.703704 | 12083 | 12083 | 12083 | 0 | 0 | 0 | 0 | 0 | 4.931253 | 0 |
| Control | Cell | 17544 | | Blank | 0 | | Dilution | 3 | IC50 | FALSE |
| Inhibition effect to HBsAg | | | | | | | | | | |
| 300 | 9226 | 8196 | 9658 | 0.152489 | 0.247106 | 0.521054 | 0.1708 | 0.189295 | 0.8292 | 0.185857736 |
| 100 | 10946 | 10340 | 10828 | 0 | 0.050156 | 0.364272 | 0.018495 | 0.0184947 | 1.810705 | 0.010110817 |
| 33.33333 | 12250 | 12980 | 13934 | 0 | 0 | 0 | 0 | 0 | 2.810705 | 0 |
| 11.11111 | 12634 | 12342 | 12000 | 0 | 0 | 0 | 0 | 0 | 3.810705 | 0 |
| 3.703704 | 10886 | 10886 | 10886 | 0 | 0 | 0 | 0 | 0 | 4.810705 | 0 |
| Control | Cell | 10886 | | Blank | 0 | | Dilution | 3 | IC50 | FALSE |

TABLE 4.3

Results of inhibition rate of Infergen ® to HBsAg and HBeAg

| Concentration (×10⁴ IU/ml) | First well | Second well | Third well | Inhibition rate First well | Inhibition rate Second well | Inhibition rate Third well | Average inhibition rate | Accumulation | 1-Accumulation | Accumulated inhibition rate |
|---|---|---|---|---|---|---|---|---|---|---|
| First batch: (Infergen ®) | | | | | | | | | | |
| Inhibition effect to HBeAg | | | | | | | | | | |
| 900 | 14172 | 12156 | 17306 | 0.091655 | 0.220869 | 0 | 0.104175 | 0.306157 | 0.895825 | 0.254710274 |
| 300 | 13390 | 12288 | 16252 | 0.1417767 | 0.212409 | 0 | 0.118062 | 0.2019827 | 1.777764 | 0.102024519 |
| 100 | 14364 | 18834 | 14194 | 0.079349 | 0 | 0.090245 | 0.056531 | 0.083921 | 2.721232 | 0.029916678 |
| 33.33333 | 15722 | 16034 | 16340 | 0 | 0 | 0 | 0 | 0.0273897 | 3.721232 | 0.007306592 |
| 11.11111 | 17504 | 17652 | 14320 | 0 | 0 | 0.082169 | 0.02739 | 0.02739 | 4.693843 | 0.005801377 |
| Control | Cell | 15602 | | Blank | 0 | | Dilution | 3 | IC50 | FALSE |
| Inhibition effect to HBsAg | | | | | | | | | | |
| 900 | 12080 | 11692 | 12234 | 0 | 0.01275 | 0 | 0.00425 | 0.025163 | 0.99575 | 0.024647111 |
| 300 | 12840 | 11484 | 12350 | 0 | 0.030313 | 0 | 0.010104 | 0.0209125 | 1.985646 | 0.010422073 |
| 100 | 12894 | 14696 | 15086 | 0 | 0 | 0 | 0 | 0.010808 | 2.985646 | 0.003606955 |
| 33.33333 | 15032 | 12928 | 13020 | 0 | 0 | 0 | 0 | 0.0108081 | 3.985646 | 0.002704416 |
| 11.11111 | 11794 | 11984 | 11508 | 0.004137 | 0 | 0.028287 | 0.010808 | 0.010808 | 4.974837 | 0.002167838 |
| Control | Cell | 11843 | | Blank | 0 | | Dilution | 3 | IC50 | FALSE |
| Second batch: (Infergen ®) | | | | | | | | | | |
| Inhibition effect to HBeAg | | | | | | | | | | |
| 900 | 6278 | 6376 | 6408 | 0.200051 | 0.187564 | 0.183486 | 0.190367 | 0.274635 | 0.809633 | 0.253290505 |
| 300 | 7692 | 9092 | 6394 | 0.0198777 | 0 | 0.18527 | 0.068383 | 0.0842678 | 1.74125 | 0.046161005 |
| 100 | 8960 | 7474 | 8190 | 0 | 0.047655 | 0 | 0.015885 | 0.015885 | 2.725365 | 0.005794856 |
| 33.33333 | 8530 | 8144 | 9682 | 0 | 0 | 0 | 0 | 0 | 3.725365 | 0 |
| 11.11111 | 7848 | 7848 | 7848 | 0 | 0 | 0 | 0 | 0 | 4.725365 | 0 |
| Control | Cell | 7848 | | Blank | 0 | | Dilution | 3 | IC50 | FALSE |
| Inhibition effect to HBsAg | | | | | | | | | | |
| 900 | 12364 | 12268 | 12274 | 0.036171 | 0.043655 | 0.043187 | 0.041004 | 0.140162 | 0.958996 | 0.12751773 |
| 300 | 11590 | 12708 | 13716 | 0.0965076 | 0.009355 | 0 | 0.035287 | 0.0991581 | 1.923709 | 0.0490186 |
| 100 | 12448 | 13468 | 13982 | 0.029623 | 0 | 0 | 0.009874 | 0.063871 | 2.913834 | 0.02144964 |
| 33.33333 | 12616 | 11346 | 12444 | 0.016526 | 0.115529 | 0.029935 | 0.053996 | 0.0539965 | 3.859838 | 0.013796309 |
| 11.11111 | 12828 | 12828 | 12828 | 0 | 0 | 0 | 0 | 0 | 4.859838 | 0 |
| Control | Cell | 12828 | | Blank | 0 | | Dilution | 3 | IC50 | FALSE |

TABLE 4.3-continued

Results of inhibition rate of Infergen ® to HBsAg and HBeAg

| Concentration (×10⁴ IU/ml) | First well | Second well | Third well | Inhibition rate First well | Inhibition rate Second well | Inhibition rate Third well | Average inhibition rate | Accumulation | 1-Accumulation | Accumulated inhibition rate |
|---|---|---|---|---|---|---|---|---|---|---|
| | | | | | | Third batch: (Infergen ®) | | | | |
| | | | | | | Inhibition effect to HBeAg | | | | |
| 900 | 7240 | 6642 | 6158 | 0.064599 | 0.14186 | 0.204393 | 0.136951 | 0.217399 | 0.863049 | 0.201211735 |
| 300 | 11072 | 8786 | 6902 | 0 | 0 | 0.108269 | 0.03609 | 0.0804479 | 1.82696 | 0.042176564 |
| 100 | 7016 | 9726 | 7552 | 0.09354 | 0 | 0.024289 | 0.039276 | 0.044358 | 2.787683 | 0.015663017 |
| 33.33333 | 7622 | 8866 | 8676 | 0.015245 | 0 | 0 | 0.005082 | 0.0050818 | 3.782601 | 0.001341671 |
| 11.11111 | 7740 | 7740 | 7740 | 0 | 0 | 0 | 0 | 0 | 4.782601 | 0 |
| Control | Cell | 7740 | | Blank | 0 | | Dilution | 3 | IC50 | FALSE |
| | | | | | | Inhibition effect to HBsAg | | | | |
| 900 | 11048 | 11856 | 11902 | 0.04775 | 0 | 0 | 0.015917 | 0.015917 | 0.984083 | 0.015916796 |
| 300 | 13454 | 12896 | 11798 | 0 | 0 | 0 | 0 | 0 | 1.984083 | 0 |
| 100 | 12846 | 13160 | 12546 | 0 | 0 | 0 | 0 | 0 | 2.984083 | 0 |
| 33.33333 | 12680 | 12458 | 12360 | 0 | 0 | 0 | 0 | 0 | 3.984083 | 0 |
| 11.11111 | 11602 | 11602 | 11602 | 0 | 0 | 0 | 0 | 0 | 4.984083 | 0 |
| Control | Cell | 11602 | | Blank | 0 | | Dilution | 3 | IC50 | FALSE |

HBeAg: Average IC50: 0 SD: 0
HBsAg: Average IC50: 0 SD: 0

Example 7

The Clinic Effects of Recombinant Super-Compound Interferon rSIFN-co

The recombinant super-compound interferon (rSIFN-co) is an invention for viral disease therapy, especially for hepatitis. Meanwhile, it can inhibit the activity of EB viruses, VSV, Herpes simplex viruses, cornaviruses, measles viruses, et al. Using Wish cells/VSV system as the assay for anti-virus activity, the results showed that: the other rIFN, was $0.9 \times 10^8$ IU/mg, Intron A was $2.0 \times 10^8$ IU/mg and rSIFN-co was $9 \times 10^8$ IU/mg. The anti-viral activity of rSIFN-co is much higher than those of the former two.

Under the permission of the State Food and Drug Administration (SFDA), People's Republic of China, the clinical trials have taken place in West China Hospital, Sichuan University, the Second Hospital of Chongqing Medical University, the First Hospital of School of Medical, Zhejiang University since the February 2003. The clinical treatment which focuses on hepatitis B is conducted under the guidance of the multicenter, double-blind random test. IFN-α1b was used as control, and the primary results showed the following:
The Effect of rSIFN-co Compared with IFN-α1b in the Treatment of Chronic Active Hepatitis B
1. Standard of patients selection: Standards 1-4 are effective for both treatment with rSIFN-co (9 μg) and IFN-α1b (5 MU, 50 μg), and Standard 1-5 are for rSIFN-co (15 μg) treatment.

1). Age: 18-65
2). HBsAg-test positive over last six months, HBeAg-test positive, PCR assay, HBV-DNA copies $\geq 10^5$/ml
3). ALT≥two times the normal value
4). Never received IFN treatment; or received the Lamividine treatment but failed or relapsed
5) Once received other IFNs (3 MU or 5 MU) treatment six months ago following the standard of SFDA, but failed or relapsed 2. Evaluation of the Effects:

In reference to the recommendations from the Tenth China National Committee of Virus Hepatitis and Hepatopathy, the effects were divided into three degrees according to the ALT level, HBV-DNA and HBeAg tests.
Response: ALT normal level, HBV-DNA negative, HBeAg negative
Partial response: ALT normal level, HBV-DNA or HBeAg negative
Non response: ALT, HBV-DNA and HBeAg unchanged
The response and partial response groups were considered effective cases.
3. Results of Clinic Trial:
Group A: treatment with rSIFN-co (9 μg)
Group B: treatment with IFN-α1b (5 MU, 50 μg)

| Period | group | Medicine | cases | Effective Rate | HBsAg Transfer to negative rate | HBeAg Transfer to negative rate | HBV-DNA Transfer to negative rate | Heptal function Recovery rate |
|---|---|---|---|---|---|---|---|---|
| 8-12 week | A | rSIFN-co(9 μg) | 32 | 46.88 (15) | 9.38 (3) | 28.13 (9) | 37.50 (12) | 84.38 (27) |
| | B | IFN-α1b (5MU, 50 μg) | 32 | 21.88 (7) | 0.00 (0) | 9.38 (3) | 15.63 (5) | 56.25 (18) |
| 16-24 week | A | rSIFN-co(9 μg) | 64 | 54.69 (35) | 7.81 (5) | 25.00 (16) | 34.38 (22) | 90.63 (58) |
| | B | IFN-α1b (5MU, 50 μg) | 64 | 25.00 (16) | 0.00 (0) | 9.38 (6) | 18.75 (12) | 78.13 (50) |

In Group C, the cases were prior treatment of chronic active hepatitis B with other IFNs (3 MU or 5 MU) that failed or relapsed and then were treated with rSIFN-co (15 µg), subcutaneous injection, every one day, for 24 weeks. The total cases were 13. After 12 weeks treatment, 7 of 13 (53.85%) were effective. 3 of 13 (23.08%) HBeAg transferred to negative; 7 of 13 (53.85%) HBV-DNA transferred to negative; 11 of 13 (84.62%) heptal functions recovered to normal.

4. The Side Effects of rSIFN-co Compared with IFN-α1b in the Treatment

The side effects of IFN include fever, nausea, myalgia, anorexia, hair loss, leucopenia and thrombocytopenia, etc. The maximum dose of IFN-α1b is 5 MIU per time; the routine dose is 3 MIU. When taken the routine dose, 90% patients have I-II degree (WHO standard) side effects. They had fever lower than 38° C., nausea, myalgia, anorexia, etc. When taken at maximum dose, the rate of side effects did not rise obviously, but were more serious. The maximum dose of rSIFN-co is 24 µg, subcutaneous injection, every one day for 3 months. The routine dose is 9 µg. When routine doses were used, less than 50% of patients had I-II degree (WHO standard) side effects, including fever below 38° C., nausea, myalgia, anorexia, leucopenia and slight thrombocytopenia. With maximum dosage, about 50% patients suffered from leucopenia and thrombocytopenia after using rSIFN-co one month, but those side effects disappeared after stopping treatment for one week. It is safe for continued use.

The Observations of rSIFN-co Treat Hepatitis C

1. Standard of Patients Selection
1) age: 18-65
2) HCV antibody positive
3) ALT≥1.5 times of the normal value, last more than 6 months 2. Evaluation of the Effects:

Referring to the standard of Infergen® for treatment of hepatitis C and according to the ALT level and HCV-RNA test, divided the effects into three degree:
Response: ALT normal level, HCV-RNA negative
Partial response: ALT normal level, HCV-RNA unchanged
Non response: ALT and HCV-RNA unchanged 3. Effects in Clinic The clinical trial was done at the same time with hepatitis B treatment. 46 cases received the treatment, 9 µg each time, subcutaneous injection, every day for 24 weeks. After treatment, 26 of 46 (56.52%) have obvious effects, 12 of 46 (26.09%) HCV-RNA transferred to negative, 26 of 46 (56.52%) heptal functions recovered to normal.

Example 8

Comparison of Inhibitory Effects of Different Interferons on HBV Gene Expression Hepatitis B virus (HBV) DNA contains consensus elements for transactivating proteins whose binding activity is regulated by interferons. Treatment of HBV-infected hepatocytes with interferons leads to inhibition of HBV gene expression. The aim of the present study was to characterize the effects of different interferons on HBV regulated transcription. Using transient transfection of human hepatoma cells with reporter plasmids containing the firefly luciferase gene under the control of HBV-Enhancer EnH I, Enh II and core promoter, Applicant studied the biological activities of three different interferons on transcription.

Materials and Methods
1. Interferons: IFN-con1 (Infergen®), IFN-Hui-Yang (rSIFN-co) and IFNα-2b (Intron A).
2. Reporter plasmid: The DNA fragments containing HBV-Enhancer EnH I, Enh II and core promoter were prepared using PCR and blunt-end cloned into the SmaI I site of the promoter- and enhancer-less firefly luciferase reporter plasmid pGL3-Basic (Promega, Wis., USA). The resulting reporter plasmid was named as pGL3-HBV-Luc.
3. Cell Culture and DNA transfection: HepG2 cells were cultured in DMEM medium supplemented with 10% FBS and 100 U/ml penicillin and 100 ug/ml streptomycin. The cells were kept in 30° C., 5% CO2 incubator. The cells were transfected with pGL3-HBV-Luc reporter plasmid using Boehringer's Lipofectin transfection kit. After 18 hours, the medium containing transfection reagents was removed and fresh medium was added with or without interferons. The cells were kept in culture for another 48 hours.
4. Luciferase Assay: Forty-eight hours after addition of interferon, the cells were harvested and cell lysis were prepared. The protein concentration of cell lysates were measured using Bio-Rad Protein Assay kit. The luciferase activity was measured using Promega's Luciferase Reporter Assay Systems according to the instructions of manufacturer.

Results

Expression of Luciferase Activity in Different Interferon-Treated Cell Lysates

| No treatment | IFN-con1 | rSIFN-co | TFNα-2b |
|---|---|---|---|
| 100 | 65 | 32 | 73 |

This result shows that rSIFN-co inhibits most effectively on the expression of HBV gene expression of HB core Antigen. This data shows inhibitory effect of rSIFN-co is twice better than Infergen® and Intron A. See FIG. 10.

Example 9

Recombinant Super-Compound Interferon Spray

Major component: Recombinant Super Compound Interferon

Characteristic: Liquid, no insoluble material

Pharmacology: Recombinant Super-Compound Interferon has a wide spectrum of anti-virus activity. Its effects are 5-20 times higher than those interferons (IFNs) which are available on the market. It can inhibit coronavirus growth in cell culture. In vitro test shows that rSIFN-co has an obvious anti-SARS virus activity. rSIFN-co effect to 10,000 and 1000 $TCID_{50}$. The Inhibitory Indexes are 0.92 µg/ml and 0.18 µg/ml respectively. The Treatment Indexes (TI) are 151.28, 773.22 respectively. The mechanism is interruption of the combination reaction between the IFN and the correspondent receptor, and inducement of the expression of 2'5'-A synthesizenzyme, protein kinase R in the target cell, therefore inhibiting expression of the viral protein. IFN can induce expression of various anti-virus proteins to inhibit the reproduce of viral proteins, enhance the function of Natural Killer (NK) cell and other Immune regulative functions, and inhibit the invasion of viruses.

Acute toxicity: All mice are alive after the maximum dose (1000 times to human dose) subcutaneous injection, did not observe LD50.

Indication: Prevention of Severe Acute Respiratory Syndrome

Dosage and Administration: Spray to both nasal cavity and throat, three times a day.

Adverse reactions: There was no report of adverse reactions from the rSIFN-co spray. It did not induce allergy. If the stimulation is occasional, adverse gastrointestinal reaction is small, and no other obvious adverse reaction was noted during treatment, it is safe to continue use. All reactions will resolve themselves.

Warning: Patients allergic to IFN and productions of E. Coli. cannot use this product.

Precautions: Before first use, spray twice to expel the air. If there is any cloudy precipitation material, if the product is expired, or there is material on the vial, do not use it.

Pediatric Use: It is unclear.

Geriatric Use: It is unclear.

Nursing mothers and pregnant women: Use with care or under physician's supervision.

Drug Interactions: It is unclear.

Overdose: One-time dose of over 27 million of International Units have not produced any adverse effects.

Supplied: 1 spray/pack, 20 ug ($1 \times 10^7$ IU)/3 ml. See FIGS. 11A-11D.

Storage: Store at 4-8° C. Do not freeze, protect from light.

Effective period: Approximately one year

Manufacture: Manufactured by Sichuan Huiyang life-engineering Ltd.

Address: 8 Yusa Road, Room 902, Building A
Chengdu, 610017
Sichuan, P.R. China

Example 9-A

In Vitro Effect of a New-Style Recombinant Compound Interferon on SARS-Associated Coronavirus Sample supplied by: Huiyang Life Engineering Lt Company, SiChuan Province Experimenter: Molecular Biology Department, microorganism and epidemiology Institute, Academy of Military Medical Science Original data: Preserved in archive of Molecular Biology Department, microorganism and epidemiology Institute, Academy of Military Medical Science 1. Materials Medicine: New-type recombinant compound interferon, 9 μg each, supplied by Huiyang Life Engineering Lt Company, SiChuan Province, Lot number: 20020501.

Cells: Vero $E_6$, supplied by Molecular Biology Department of Microorganism and Epidemiology Institute, Academy of Military Medical Science.

Virus: SARS-associated coronavirus, BJ-01, supplied by Molecular Biology Department of Microorganism and Epidemiology Institute, Academy of Military Medical Science.

Cell medium: DMEM supplemented with 10% FBS.

2. Condition Virus was measured in grade $3^{rd}$ laboratory of biosafety

3. Method

CPE (cytopathic effect) assay of $TCID_{50}$: 100 μl of Vero $E_6$ cells were plated in 96-well plates at $2 \times 10^4$ cells per well. After 24 hr incubation at 37° C., Vero E6 monolayer cells were treated with 9 levels of SARS-associated coronavirus dilution by 10-fold dilution, 4 wells per dilution. The cells were incubated at 37° C. and 5% $CO_2$. CPE (cytopathic effect) was examined daily by microscopy. CPE less than 25% was determined as +, 26-50% as ++, 51-75% as +++, 76-100% as ++++. CPE was recorded. Then $TCID_{50}$ was calculated by Reed-Muench method.

Cytotoxicity of medicine: Vero $E_6$ cells were inoculated into 96-well plates at $2 \times 10^4$ cells (100 ul) per well. After 24-hr incubation at 37° C., cells grew up to monolayer. The medicine was diluted into 36, 18, 9, 4.5, 2.259 μg/ml (final concentration) and added into wells each for 4 wells. The normal cells as control group were set. CPE of medicine group was daily observed during 5-day period, and then the concentration of medicine exhibiting no toxicity was determined.

CPE assay of the activity of the medicine against SARS-associated coronavirus: 100 μl of Vero $E_6$ cells were plated in 96-well plates at $2 \times 10^4$ cells per well. After 24 hr incubation at 37° C., cells grew up to monolayer. The medicine at the maximal concentration exhibiting no cytotoxicity was diluted into 5 levels by 2-fold dilution and added into wells (100 μl per well). By incubation with 5% $CO_2$ at 37° C. for 24-hour, different concentration of virus ($10^{-3}$, $10^{-4}$, $10^{-5}$) were added. After treatment with virus for 48-72 hours, CPE was examined (CPE less than 25% was determined as +, 26-50% as ++, 51-75% as +++, 76-100% as ++++, normal cell as –). The cells were divided into the normal group, the medicine control group, and the different dilution of virus control group, 4 wells per group. CPE was examined daily. Till cytopathic effect was obviously exhibited in the virus control group, the anti-virus activity of interferon was evaluated. The experiment was repeated. $IC_{50}$ of the medicine was calculated by Reed-Muench method.

4. Results

Toxicity of virus: $TCID_{50}$ of virus was $10^{-8}$.

Cytotoxicity of medicine: the concentration of Recombinant compound interferon exhibiting no cytotoxicity was 18 μg/ml, the cells shape was similar with the control group, and no cytopathic effect was exhibited.

The anti-virus effect of the medicine: Shown in Table 9-A.1 and Table 9-A.2

TABLE 9-A.1 the anti-virus effect of new-type recombinant compound interferon (first experiment)

| Concentration of IFN | CPE at different concentration of virus | | |
|---|---|---|---|
| (μg/ml) | $10^{-3}$ | $10^{-4}$ | $10^{-5}$ |
| 18 | – | – | – |
| 9 | – | – | – |
| 4.5 | ++ | – | – |
| 2.25 | +++ | ++ | – |
| 1.125 | ++++ | ++++ | ++ |
| Virus control group | ++++ | ++++ | +++ |
| Normal group | – | – | – |
| Medicine control group | – | – | – |

TABLE 9-A.2 the anti-virus effect of new-type recombinant compound interferon (second experiment)

| Concentration of IFN | CPE at different concentration of virus | | |
|---|---|---|---|
| (μg/ml) | $10^{-3}$ | $10^{-4}$ | $10^{-5}$ |
| 18 | – | – | – |
| 9 | – | – | – |
| 4.5 | + | – | – |
| 2.25 | +++ | ++ | – |
| 1.125 | ++++ | ++++ | ++ |
| Virus control group | ++++ | ++++ | ++++ |
| Normal group | – | – | – |
| Medicine control group | – | – | – |

5. Conclusion

The concentration of the new-type recombinant compound interferon exhibiting no cytotoxicity at 18 μg/ml. Its $IC_{50}$ were 1.27, 2.25, and 4.04 μg/ml respectively according to the concentration of $10^{-5}$ (1000 $TCID_{50}$), $10^{-4}$ (1000 $TCID_{50}$), $10^{-3}$ (100000 $TCID_{50}$) of SARS-associated coronavirus (Table 9-A.3).

TABLE 9-A.3

IC50 of IFN at different concentrations of virus

| Dilution of virus | IC50 of IFN(ug/ml) |
|---|---|
| $10^{-3}$ | 4.04 |
| $10^{-4}$ | 2.25 |
| $10^{-5}$ | 1.27 |

Principal: Jin-yan Wang
Laboratory assistant: Yan-hong Zhao, Xiao-guang Ji, Xiao-yu Li.
Original data: Preserved in archives of Molecular Biology Department, microorganism and epidemiology Institute, Academy of Military Medical Science
Date: From May 12th to 30th, 2003

Example 9-B

In Vitro Effect of a New-Type Recombinant Compound Interferon and Recombinant Interferon α-2b Injection on SARS-Associated Coronavirus
Sample (rSIFN-co) supplied by: Huiyang Life Engineering Ltd., Sichuan province
Experimenter: Molecular Biology Department, Institute of microbiology and epidemiology, Academy of Military Medical Science
Original data: Preserved in monument room of Molecular Biology Department, Institute of microbiology and epidemiology, Academy of Military Medical Science 1. Materials Medicine: New-type recombinant compound interferon (rSIFN-co), 618 μg/ml, supplied by Huiyang Life Engineering Ltd., SiChuan Province; Alfaron (recombinant interferon α-2b injection), supplied by Tianjin Hualida Biotechnology Co., Ltd. 30 ug/vial (300,0000 IU/vial), Lot Number: 20030105.
Cells: Vero $E_6$, supplied by Molecular Biology Department of Institute of microbiology and epidemiology, Academy of Military Medical Science.
Virus: SARS-associated coronavirus, BJ-01, supplied by Molecular Biology Department of Institute of microbiology and epidemiology, Academy of Military Medical Science.
Condition: Viruses were measured in grade $3^{rd}$ laboratory of biosafety 2. Method $TCID_{50}$ was measured with CPE assay: Vero $E_6$ cells were inoculated in 96-well plates at $2\times10^4$ cells (100 μl) per well. After a 24-hr incubation at 37° C., Vero E6 monolayers were treated with 9 levels of SARS-associated coronavirus dilution by 10 times decreasing, each dilution per 4 wells. The cells were incubated at 37° C. and 5% carbon dioxide. CPE was examined daily by phase-contrast microscopy. CPE less than 25% was determined as +, 26-50% as ++, 51-75% as +++, 76-100% as ++++. CPE was recorded. Then $TCID_{50}$ was calculated by Reed-Muench method.

$TC_{50}$ of IFNs were measured by MTT assay: Vero $E_6$ cells were inoculated in 96-well plates at $2\times10^4$ cells per well (100 μl). After 24-hr incubation at 37° C., the supernatant liquid was removed when cells grew up to monolayer, then Vero $E_6$ was treated with different concentration of IFNs, each dilution per 4 wells. Normal group was set. After 5-day observation, the cells were mixed with MTT for 4 hours. After that, remove the liquid, and then thereafter DMSO were added into cells for 0.5 hour. The $OD_{570nm}$ was measured by microplate reader. Finally, $TC_{50}$ was calculated by Reed-Muench method.

The activity of the INFs against SARS-associated coronavirus was measured with MTT assay: 100 μl of Vero $E_6$ cells were inoculated in 96-well plates at $2\times10^4$ cells per well. After 24-hr incubation 37° C., cells became monolayer. The medicine dilution at the concentration of exhibiting no cytotoxicity was 5 times decreasing and there were 5 levels of dilution. Then each dilution was added to 4 wells, 100 ul per well. After 24-hour incubation at 37° C. and 5% $CO_2$, IFN solution was removed, then different concentrations of virus dilution (10000, 1000, 100 $TCID_{50}$) were added into dishes, 4 wells per dilution. The cells were divided into the normal group, the medicine control group, and the different dilution of virus control group (10000, 1000, 100 $TCID_{50}$). The cells were incubated at 37° C. and 5% $CO_2$ for 48-72 hr, until cytopathic effect was exhibited in the virus control group, CPE was recorded (CPE less than 25% was determined as +, 26-50% as ++, 51-75% as +++, 76-100% as ++++, normal cell as −). The growth ability of cells was measured with MTT assay, and then the antivirus effect of the INFs was evaluated. The experiment was repeated 3 times. $IC_{50}$ of the medicine was calculated by Reed-Muench method.

3. Results $TCID_{50}$ of virus: $TCID_{50}$ of virus was $10^{-7}$.

$TC_{50}$ of IFNs: The concentration of new-type recombinant compound interferon (rSIFN-co) exhibiting no cytotoxicity was 100 μg/ml, and that of recombinant IFNα-2b was 12.5 μg/ml, the cells shape was identical with the normal group at that concentration. TC50 of new-type recombinant compound interferon (rSIFN-co) was 139.18 μg/ml, that of recombinant IFNα-2b was 17.18 μg/ml.

TABLE 9-B.1

| IFN | $TC_{50}$ of IFNs | | | |
|---|---|---|---|---|
| | $TC_{50}$ (μg/ml) | | | Mean value |
| | $1^{st}$ experiment | $2^{nd}$ experiment | $3^{rd}$ experiment | ($\bar{X} \pm SD$, n = 3) |
| new-type recombinant compound interferon | 141.42 | 125.96 | 150.08 | 139.18 ± 12.22 |
| IFNα-2b | 17.68 | 15.75 | 18.10 | 17.18 ± 1.25 |

The anti-virus effect of the medicine: The anti-virus effects of two IFNs were observed in vitro. The results of the experiments are shown on the Table 9-B.2, and the results of TI are shown on the Table 9-B.3.

TABLE 9-B.2

The anti-virus activity of IFNs

| IFNs | Concentration of virus ($TCID_{50}$) | $IC_{50}(\mu g/ml)$ 1st experiment | 2nd experiment | 3rd experiment | Mean value - (X ± SD, n = 3) |
|---|---|---|---|---|---|
| new-type recombinant compound interferon | 10000 | 0.79 | 1.04 | 0.93 | 0.92 ± 0.12 |
| IFNα-2b | | 5.04 | 4.56 | 4.65 | 4.75 ± 0.25 |
| new-type recombinant compound interferon | 1000 | 0.19 | 0.18 | 0.18 | 0.18 ± 0.01 |
| IFNα-2b | | 1.18 | 1.19 | 1.12 | 1.16 ± 0.04 |
| new-type recombinant compound interferon | 100 | 0.08 | 0.10 | 0.11 | 0.10 ± 0.02 |
| IFNα-2b | | 0.33 | 0.21 | 0.30 | 0.28 ± 0.06 |

TABLE 9-B.3

The anti-virus activity of IFNs

| IFNs | Concentration of virus ($TCID_{50}$) | $TC_{50}$ ($\mu g/ml$) | $IC_{50}$ ($\mu g/ml$) | TI ($TC_{50}/IC_{50}$) |
|---|---|---|---|---|
| new-type recombinant compound interferon | 10000 | 139.18 | 0.92 | 151.28 |
| IFNα-2b | | 17.18 | 4.75 | 3.62 |
| new-type recombinant compound interferon | 1000 | 139.18 | 0.18 | 773.22 |
| IFNα-2b | | 17.18 | 1.16 | 14.78 |
| new-type recombinant compound interferon | 100 | 139.18 | 0.10 | 1391.80 |
| IFNα-2b | | 17.18 | 0.28 | 61.36 |

4. Conclusion

The protection effect of new-type recombinant compound interferon (rSIFN-co) and IFNα-2b on Vero $E_6$ was observed in vitro, and the anti-virus ability of IFNs was manifested. $IC_{50}$ of new-type recombinant compound interferon on SARS-associated coronavirus at the concentration of 10000, 1000, and 100 was 0.92, 0.18, and 0.10 µg/ml in three experiments, TI of that was 151.28, 773.22, and 1391.80 respectively. $IC_{50}$ of IFNα-2b was 4.75, 1.16, and 0.28 µg/ml, TI (treatment index) of that was 3.62, 14.78, 61.36 respectively.

Most importantly, the two tests (See the above Examples 9A & 9B) of in vitro anti-SARS virus effect of rSIFN-co all testified that even the effective dose of rSIFN-co to inhibit SARS virus is ⅕ of that of Interferon α-2b which was used clinically in China at present, the Treatment Index (TI) of rSIFN-co is nearly 50 times of that of Interferon a-2b. (SEE: In vitro effect of a new-type recombinant compound interferon and recombinant interferon-α-2b injection on SARS-associated coronavirus. By The Institute of Microbiology & Epidemiology, Academy of Military Medical Science) Also, see FIG. 12.

Thirty thousand sprays of rSIFN-co had been used among front-line nurses and doctors, and people at high risk in Sichuan province. The result shows that none of the nurses and doctors infected SARS in Sichuan Province.
Principal: Jin-yan Wang
Laboratory assistant: Yan-hong Zhao, Xiao-guang Ji, Min Zhang, Jing-hua, Zhao.
Date: From Jul. 1st to 30th, 2003

Example 10

Side Effects and Changes in Body Temperature when Using rSIFN-co

There are usually more side effects to using interferon. The side effects includes: nausea, muscle soreness, loss of appetite, hair loss, hypoleucocytosis (hypoleukmia; hypoleukocytosis; hypoleukia), and decrease in blood platelet, etc.
Method Sample patients are divided into two groups. 10 patients in Group A were injected with 9 µg rSIFN-co. 11 patients in Group B were injected with 9 µg Infergen®. Both groups were monitored for 48 hours after injections. First monitoring was recorded 1 hour after injection. After that, records were taken every 2 hours.

Table 11.1 is the comparison of side effects between patients being injected with 9 µg of rSIFN-co and 9 µg of Infergen®.

TABLE 11.1

Side Effects

| Body Systems | Reactions | rSIFN-co 9 µg (Group A) Person: n = 10 Headcount | Infergen ® 9 µg (Group B) Person: n = 11 Headcount |
|---|---|---|---|
| In General | Feeble | 3 | 3 |
| | Fever | 3 | 6 |
| | Sole heat | 1 | |
| | frigolabile | 3 | 4 |
| | Leg strengthless | | 3 |
| | Mild lumbago | 2 | 1 |
| | Body soreness | 4 | 5 |
| Central Nervous System/ Peripheral Nervous System | Headache | 3 | 6 |
| | Dizziness | 2 | 11 |
| | Drowsiness | | 3 |
| Gastroenterostomy | Apoclesis | 1 | |
| | Celiodynia | 1 | |
| | Diarrhea | 1 | |
| Musculoskeletal system | Myalgia | 1 | 2 |
| | Arthralgia | 2 | |
| Respiratory system | Stuffy nose | 1 | |
| *Paropsia* | Swollen Eyes | | 1 |

Results

For those patients who were injected with rSIFN-co, the side effects were minor. They had some common symptoms similar to flu, such as: headache, feebleness, frigolability, muscle soreness, hidrosis, arthralgia (arthrodynia; arthronalgia). The side effects of those patients whom were injected with Infergen® were worse than those injected with rSIFN-co.

From FIGS. 13A-1, 13A-2, 13B-1, and 13B-2, it was obvious that the body temperatures of sample patients in Group B were higher than the patients in Group A. It also reflected that the endurance of rSIFN-co was much better than Infergen®.

Example 11

Effects of Recombinant Super-Compound Interferon (rSIFN-co) on Ebola Virus

Background: Ebola virus is a notoriously deadly virus that causes fearsome symptoms, the most prominent being high fever and massive internal bleeding. Ebola virus kills as many as 90% of the people it infects. It is one of the viruses capable of causing hemorrhagic (bloody) fever. There is no specific treatment for the disease. Currently, patients receive supportive therapy. This consists of balancing the patient's fluids and electrolytes, maintaining their oxygen level and blood pressure, and treating them for any complicating infections. Death can occur within 10 days of the onset of symptoms.

1. Materials
   1.1 Drugs: rSIFN-co, provided by Sichuan Biotechnology Research Center.
   1.2 Virus: Ebola, supplied by The Academy of Military Medical Science, Institute of Microbiology Epidemiology.
   1.3 Safety level of experiment: Viral experiments were carried under Biological Laboratory Safety System level 3.
   1.4 Animals: 60 BALB/c mice
2 Method
   2.1 60 mice were randomly separated into 6 groups, each group consisting of 10 mice. Group 1 was treated with 1 μg/ of rSIFN-co on the day of inoculation with Ebola virus. Group 2 was treated with 1 μg/ of rSIFN-co day one (1) after inoculation with Ebola virus. Group 3 was treated with 1 μg/ of rSIFN-co on the day two (2) after inoculation with Ebola virus. Group 4 was treated with 1 μg/ of rSIFN-co on day three (3) after inoculation with Ebola virus. Group 5 was treated with 1 μg/ of rSIFN-co on day four (4) after inoculation with Ebola virus. Group 6 was not treated with rSIFN-co and this is designated as the control group.
   2.2 Administration of the medication: 1 μg/ of rSIFN-co was administered once a day for six (6) consecutive days.
3 Results All ten (10) mice in group 6 (control group) died. All mice in groups one (1), two (2) and three (3) survived with no observable toxic effect. In groups four (4) and five (5), showed some effects.

4 Conclusion

Clearly these result show effectiveness of rSIFN-co against Ebola virus.

Example 12

Anti-HIV Effects of Recombinant Super-Compound Interferon (rSIFN-co).

1. Materials
   1.1 Wild-Type HIV
   1.2 Drug Resistant HIV
   1.3 293-CD4-CCR5 cells
   1.4 DMEM, Gibco
   1.5 Fetal Bovine Seru, Gibco
   1.6 rSIFN-co provided by Sichuan Biotechnology Research Center
   1.7 96-well plate, NUNC
   1.8 $CO_2$ incubator
   1.9 Laminar Flow Hood
   1.10 Fluorometer
   1.11 UV Absorbance Meter
   1.12 Others
2. Method
   2.1 293-CD4-CCR5 cells in exponential (log) phase were obtained, digested with 0.25% pancreatin, stained with Trypan blue stain to determine cell number and diluted with DMEM to concentration of $2.0\times10^5$ cells per milliliter (cell/ml).
   2.2 Each well of 96-well plate was filled with 100 μl (microliters) of 293-CD4-CCR5-DMEM suspension solution. The plate was placed into 5% carbon dioxide incubator at 37 degrees Celsius and observed the next day seventy percent (70%) of basal area of the well were recovered.
   2.3 After supernatant was removed, 100 μl (microliters) of different concentrations of rSIFN-co were added to each well. Two controls were used: Phosphate Buffered Saline (PBS) and Growth Media.
   2.4 The plate was placed into carbon dioxide incubator at 37 degrees Celsius for approximately 18 to 20 hours.
   2.5 Experimental wells: Different concentrations of the Wild-Type HIV and Drug Resistant HIV viruses were placed into each well at 100 μl (microliters) per well.
      Control wells: No virus was added, only 100 μl (microliters) of DMEM per well.
   2.6 The plate was placed into carbon dioxide incubator at 37 degrees Celsius for approximately 24 hours.
   2.7 Routine Luciferase assay was performed and protein concentrations of the supernatants were measured. Luciferase was measured in RLU/mg units.
3 Results rSIFN-co can inhibit HIV at level of ≥4 nanograms per milliliter (ng/ml). See Table 4 and FIGS. 14-15. When using Luciferase as Y axis and concentration of rSIFN-co as X axis, using EXCEL, it is clear that at level of rSIFN-co ≥4 nanograms per milliliter (ng/ml), the level of Luciferase activities are obviously lower than in PBS and Medium controls. A clear inverse dose-dependent response has been shown.

TABLE 4

Comparison of Inhibition of Wild-Type HIV and Drug Resistant HIV by rSIFN-co

| Concentration | Luciferase Assay | |
| --- | --- | --- |
| of rSIFN-co | Wild-Type HIV | Drug Resistant HIV |
| Medium | 13500 + 2000 | 18000 + 2000 |
| 1 μg/ml | 3000 + 200 | 2800 + 800 |
| 500 ng/ml | 3000 + 600 | 2800 + 900 |
| 250 ng/ml | 3400 + 400 | 4000 + 600 |
| 125 ng/ml | 4300 + 200 | 4100 + 600 |
| 62.5 ng/ml | 4300 + 400 | 4100 + 1000 |
| 31 ng/ml | 5000 + 800 | 5100 + 800 |
| 15 ng/ml | 7200 + 400 | 6000 + 1500 |
| 7.5 ng/ml | 7000 + 800 | 7700 + 1300 |
| 4 ng/ml | 9000 + 2000 | 8900 + 2000 |
| PBS | 13000 + 3000 | 15100 + 2300 |
| Medium | 16000 + 3600 | 19000 + 2500 |

4 Conclusion: rSIFN-co is Effective Against Both: Wild-Type HIV and Drug Resistant HIV.

Example 13

Anti-Influenza Effects of Recombinant Super-Compound Interferon (rSIFN-co).

1. Materials
   1.1. 10-day old chick embryonic membrane cells
   1.2. SIFN-co provided by Sichuan Biotechnology Research Center
   1.3. Influenza virus provided by Molecular Biology Department of Institute of microbiology and epidemiology, Academy of Military Medical Science.
   1.4. DMEM, Gibco
   1.5. Newborn Calf Serum
   1.6. 96-well plate, NUNC
   1.7. $CO_2$ incubator
   1.8. Laminar Flow Hood
   1.9. Inverted Microscope
   1.10. Others
2. Method
   2.1 10-day old chick embryonic membrane cell in exponential (log) phase were obtained, digested with 0.25% pancreatin, stained with Trypan blue stain to determine cell number and diluted with DMEM to concentration of $2.0 \times 10^5$ cells per milliliter (cell/ml).
   2.2 Each well of 96-well plate was filled with 100 μl (microliters) of 293-CD4-CCR5-DMEM suspension solution. The plate was placed into carbon dioxide incubator at 37 degrees Celsius. The next day cells grew to a monolayer.
   2.3 After supernatant was removed, 100 μl (microliters) of different concentrations of rSIFN-co were added to each well. Two control wells: No rSIFN-co was added
   2.4 The plate was placed into carbon dioxide incubator at 37 degrees Celsius for approximately 18 to 20 hours.
   2.5 Experimental wells: Different concentrations of the Influenza virus were placed into each well at 100 microliters (μl) per well.
      Control wells: No Influenza virus was added, only 100 μl (microliters) of DMEM per well.
   2.6 The plate was placed into carbon dioxide incubator at 37 degrees Celsius for approximately 24 hours.
   2.7 Cells were observed under inverted microscope.
3. Results
   3.1 Under inverted microscope, the cells in the control well with Influenza virus added and without interferon had obvious CPE, such as rounding of cells, cell necroses, decrease in reflective light and sloughing off.
   3.2 Cells from the experimental wells containing rSIFN-co at concentration ≥10 nanogram per milliliter (ng/ml) had no CPE and morphology comparable to normal cells. See FIG. 16.
   3.3 Control Wells without Influenza virus added and without interferon did not have any CPE.
4 Conclusion
   At concentration ≥10 nanogram per milliliter (ng/ml) rSIFN-co is effective against Influenza virus.

---

What is claimed is:

1. A method for treating viral diseases in a subject, comprising administering to the subject an effective amount of a recombinant interferon, wherein the interferon has the amino acid sequence of SEQ ID NO:2 and is encoded by the nucleotide sequence SEQ ID NO:1.

2. The method of claim 1, wherein the viral diseases is hepatitis A, hepatitis B, hepatitis C, other types of hepatitis, infections of viruses caused by Epstein-Barr virus, Human Immunodeficiency Virus (HIV), Ebola Virus, Severe Acute Respiratory Syndrome Virus (SARS), Influenza Virus, Cytomegalovirus, herpes simplex viruses, or other type of herpes viruses, papovaviruses, poxviruses, picornaviruses, adenoviruses, rhinoviruses, human T-cell leukemia viruses I, or human T-cell leukemia viruses II, or human T-cell leukemia virus III.

3. The method of claim 1, wherein the interferon is administered at a dose ranging from nanograms to micrograms.

4. The method of claim 1, wherein the interferon is administered orally, via vein injection, muscle injection, peritoneal injection, subcutaneous injection, nasal or mucosal administration, or by inhalation via a respirator.

5. The method of claim 1, wherein the interferon is administered subcutaneously or intramuscularly at a dose of higher than or equal to 10 Million International Units per square meter of surface area.

6. The method of claim 1, wherein the interferon is administered subcutaneously or intramuscularly at a dose of higher than or equal to 20 Million International Units per square meter of surface area.

7. The method of claim 1, wherein the interferon is lyophilized.

8. The method of claim 1, wherein the interferon is administered following a protocol of 9 µg, 15 µg or 24 µg injection per day, 3 times a week, for a total of 24 weeks.

9. A method for treating tumors in a subject, comprising administering to the subject an effective amount of a recombinant interferon, wherein the interferon has the amino acid sequence of SEQ ID NO:2 and is encoded by the nucleotide sequence SEQ ID NO:1, wherein the tumors are selected from the group consisting of melanoma, carcinoid tumors, renal cell carcinoma, stomach/abdominal cancer, rectal cancer, breast cancer, ovarian cancer, chronic myelocytic leukemia, hairy cell leukemia, myeloma, and Kaposi's sarcoma.

10. The method of claim 9, wherein the interferon is administered at a dose ranging from nanograms to micrograms.

11. The method of claim 9, wherein the interferon is administered orally, via vein injection, muscle injection, peritoneal injection, subcutaneous injection, nasal or mucosal administration, or by inhalation via a respirator.

12. The method of claim 9, wherein the interferon is administered subcutaneously or intramuscularly at a dose of higher than or equal to 10 Million International Units per square meter of surface area.

13. The method of claim 9, wherein the interferon is administered subcutaneously or intramuscularly at a dose of higher than or equal to 20 Million International Units per square meter of surface area.

14. The method of claim 9, wherein the interferon is lyophilized.

15. The method of claim 9, wherein the interferon is administered following a protocol of 9 µg, 15 µg or 24 µg injection per day, 3 times a week, for a total of 24 weeks.

* * * * *